United States Patent [19]

Berger et al.

[11] Patent Number: 5,258,401

[45] Date of Patent: Nov. 2, 1993

[54] CHOLESTEROL LOWERING COMPOUNDS

[75] Inventors: Gregory D. Berger, Belle Mead; Robert W. Marquis, Jr., Iselin; Albert J. Robichaud, Stirling, all of N.J.; Edward M. Scolnick, Wynnewood, Pa.

[73] Assignee: Merck & Co., Inc., Rahway, N.J.

[21] Appl. No.: 938,981

[22] Filed: Sep. 10, 1992

Related U.S. Application Data

[63] Continuation-in-part of Ser. No. 911,441, Jul. 10, 1992, abandoned.

[51] Int. Cl.$^5$ ............... A61K 31/335; A61K 31/365; A61K 31/38; A61K 31/34; C07D 319/04; C07D 405/06; C07D 405/08; C07D 407/06

[52] U.S. Cl. ................ 514/452; 514/422; 514/414; 514/406; 514/397; 514/382; 514/374; 514/365; 514/338; 514/333; 514/321; 514/256; 514/253; 514/233.8; 514/228.2; 546/256; 546/270; 546/197; 546/187; 548/518; 548/517; 548/455; 548/454; 548/364.4; 548/253; 548/311.7; 548/236; 548/204; 549/363; 549/310; 549/229; 549/60; 549/58; 549/28; 549/23; 549/13

[58] Field of Search .............. 549/363, 60, 58, 28, 549/13, 229, 310, 23; 514/452, 422, 414, 406, 397, 382, 374, 365, 338, 333, 321, 256, 253, 233.8, 228; 548/454, 455, 517, 518, 374, 336, 253, 236, 204; 546/256, 270, 197, 187

[56] References Cited

U.S. PATENT DOCUMENTS

| | | | |
|---|---|---|---|
| 5,026,554 | 6/1992 | Bergstrom et al. | 549/363 |
| 5,055,487 | 10/1992 | Bergstrom et al. | 514/452 |
| 5,096,923 | 3/1992 | Bergstrom et al. | 514/452 |
| 5,102,907 | 4/1992 | Bergstrom et al. | 549/363 |
| 5,132,320 | 7/1992 | Bergstrom et al. | 514/452 |

FOREIGN PATENT DOCUMENTS

| | | |
|---|---|---|
| 494622 | 7/1992 | European Pat. Off. |
| WO92/12156 | 7/1992 | PCT Int'l Appl. |
| WO92/12159 | 7/1992 | PCT Int'l Appl. |
| WO92/12160 | 7/1992 | PCT Int'l Appl. |
| WO92/16530 | 10/1992 | PCT Int'l Appl. |

OTHER PUBLICATIONS

Baxter et al., *J. Biol. Chem.* vol. 267, 11705-11708 (1992).
Dawson et al., *J. Antibiotics*, 639-647 (May 1992).
Sidebottom et al., *J. Antibiotics*, 45, 648-657 (May 1992).

*Primary Examiner*—Nicky Chan
*Attorney, Agent, or Firm*—Charles M. Caruso; Melvin Winokur; Carol S. Quagliato

[57] ABSTRACT

Disclosed herein are compounds of structural formula (I)

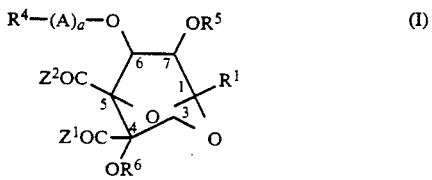

which are useful as cholesterol lowering agents. These compounds are also useful as inhibitors of squalene synthase, inhibitors of fungal growth, inhibitors of farnesyl-protein transferase and farnesylation of the oncogene protein Ras. These compounds are also useful in the treatment of cancer.

10 Claims, No Drawings

CHOLESTEROL LOWERING COMPOUNDS

RELATED APPLICATION

The present application is a continuation-in-part of copending application Ser. No. 911,441, filed Jul. 10, 1992 now abandoned.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR® (lovastatin) and ZOCOR® (simvastatin), now commercially available, are members of a group of very active antihypercholesterolemic agents that function by limiting cholesterol biosynthesis by inhibiting the enzyme, HMG-CoA reductase.

Squalene synthase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthase have employed pyrophosphate or pyrophosphate analogs containing compounds such as those described in P. Ortiz de Montellano et al, J. Med Chem. 20, 243 (1977) and E. J. Corey and R. Volante, J. Am. Chem. Soc., 98, 1291 (1976). S. Biller (U.S. Pat. No. 4,871,721) describes isoprenoid (phosphinylmethyl)phosphonates as inhibitors of squalene synthase.

Recently certain nonphosphorous containing inhibitors of squalene synthase have been isolated as natural products. These natural product inhibitors are described in U.S. Pat. Nos. 5,102,907; 5,096,923; 5,055,487 and 5,026,554. A need still remains for a more effective squalene synthase inhibitor, i.e. one that provides a greater antihypercholesterolemic effect and exhibits a good safety profile.

The present invention is directed to semi-synthetic analogs of the above-noted natural products.

DETAILED DESCRIPTION OF THE INVENTION

This invention relates to compounds of structural formula (I) which are useful as cholesterol lowering agents:

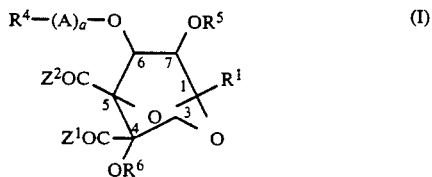

wherein
a is 0 or 1;
A is $-C(O)-$, $-NR^3-C(O)-$, or $-OC(O)-$;
$R^1$ is selected from the group consisting of:
(1) $C_{1-20}$alkyl,
(2) substituted $C_{1-20}$alkyl in which one or more substituents is selected from:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3N-C(O)-O-$, and
  (t) $R^2O-C(O)-NR^3-$;
(3) $C_{1-20}$alkyl wherein one or more of the carbons is replaced by $-NR^3-$, $-O-$, or $-S(O)_n-$;
(4) substituted $C_{1-20}$alkyl wherein one or more of the carbons is replaced by $-NR^3-$, $-O-$ or $-S(O)_n-$ and wherein one or more carbon substituents is selected from:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl-,
  (i) aryl substituted with X and Y,
  (j) heteroaryl substituted with X and Y,
  (k) heterocycloalkyl,
  (l) arylS(O)$_n-$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3N-C(O)-O-$, and
  (t) $R^2O-C(O)-NR^3-$;
(5) aryl substituted with X and Y;
(6) heteroaryl substituted with X and Y;
(7) $C_{2-20}$alkenyl wherein alkenyl contains one or more double bonds;
(8) substituted $C_{2-20}$alkenyl wherein alkenyl contains one or more double bonds and wherein one or more of the carbons is substituted with:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl, (l) arylS(O)$_n$—, wherein aryl is substituted with X and Y,
(m) R$^3$C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(9) C$_{2-20}$alkenyl wherein alkenyl contains one or more double bonds and one or more of the nonolefinic carbons is replaced by —NR$^3$—, —O— or —S(O)$_n$—;
(10) substituted C$_{2-20}$alkenyl wherein alkenyl contains one or more double bonds and one or more of the nonolefinic carbons is replaced by —NR$^3$—, —O— or —S(O)$_n$— and wherein one or more carbon substituents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl-,
(i) aryl substituted with X and Y,
(j) heteroaryl substituted with X and Y,
(k) heterocycloalkyl,
(l) arylS(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(11) C$_{3-10}$cycloalkyl;
(12) substituted C$_{3-10}$cycloalkyl in which one or more of the substituents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) R$^3$—C(O)—NR$^3$—,
(n) R$^3$R$^3$N—C(O)—,
(o) C$_{1-10}$alkylS(O)$_n$—,
(p) C$_{1-10}$alkyl,
(q) —CO$_2$H,
(r) -vinylidene,
(s) R$^3$—C(O)—,
(t) R$^2$O—C(O)—O—,
(u) R$^3$R$^3$N—C(O)—O—, and
(v) R$^2$O—C(O)—NR$^3$—;
each R$^2$ is independently selected from:
(1) C$_{1-10}$alkyl;
(2) aryl substituted with X and Y;
(3) arylC$_{1-4}$alkyl wherein aryl is substituted with X and Y;
(4) heteroaryl wherein heteroaryl is substituted with X and Y;
(5) heteroarylC$_{1-4}$alkyl- wherein heteroaryl is substituted with X and Y;
(6) heterocycloalkylC$_{1-4}$alkyl-;
(7) C$_{2-10}$alkenyl;
(8) arylC$_{2-10}$alkenyl wherein aryl is substituted with X and Y; and
(9) C$_{3-10}$alkynyl;
each R$^3$ is independently selected from:
(1) C$_{1-10}$alkyl;
(2) aryl substituted with X and Y;
(3) arylC$_{1-4}$alkyl wherein aryl is substituted with X and Y;
(4) heteroaryl wherein heteroaryl is substituted with X and Y;
(5) heteroarylC$_{1-4}$alkyl- wherein heteroaryl is substituted with X and Y;
(6) heterocycloalkylC$_{1-4}$alkyl-;
(7) C$_{2-10}$alkenyl;
(8) arylC$_{2-10}$alkenyl wherein aryl is substituted with X and Y;
(9) C$_{3-10}$alkynyl;
(10) hydrogen; and
(11) C$_{1-5}$alkyl substituted with X$^1$;
R$^4$ is selected from the group consisting of:
(1) C$_{1-20}$alkyl;
(2) substituted C$_{1-20}$alkyl in which one or more substituents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(3) C$_{1-20}$alkyl wherein one or more of the carbons is replaced by —NR$_3$—, —O—, or —S(O)$_n$—;
(4) substituted C$_{1-20}$alkyl wherein one or more of the carbons is replaced by —NR$^3$—, —O— or —S(O)$_n$— and wherein one or more carbon substituents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl-,
(i) aryl substituted with X and Y, (j) heteroaryl substituted with X and Y,
(k) heterocycloalkyl,
(l) arylS(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(5) aryl substituted with X and Y;
(6) heteroaryl substituted with X and Y;
(7) C$_{2-20}$alkenyl wherein alkenyl contains one or more double bonds;
(8) substituted C$_{2-20}$alkenyl wherein alkenyl contains one or more double bonds and wherein one or more of the carbons is substituted with:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(9) C$_{2-20}$alkenyl wherein alkenyl contains one or more double bonds and one or more of the nonolefinic carbons is replaced by —NR$^3$—, —O— or —S(O)$_n$—;
(10) substituted C$_{2-20}$alkenyl wherein alkenyl contains one or more double bonds and one or more of the nonolefinic carbons is replaced by —NR$^3$—, —O— or —S(O)$_n$— and wherein one or more carbon substitutents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl-,
(i) aryl substituted with X and Y,
(j) heteroaryl substituted with X and Y,
(k) heterocycloalkyl,
(l) arylS(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(11) C$_{3-10}$cycloalkyl;
(12) substituted C$_{3-10}$cycloalkyl in which one or more of the substituents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—; and
(13) hydrogen;
R$^5$ is selected from the group consisting of:
(1) hydrogen;
(2) C$_{1-10}$alkyl;
(3) aryl substituted with X and Y;
(4) arylC$_{1-4}$alkyl, wherein aryl is substituted with X and Y;
(5) R$^2$O—C(O)—;
(6) C$_{3-10}$cycloalkyl;
(7) R$^3$—C(O)—; and
(8) R$^3$R$^3$N—C(O)—;
R$^6$ and R$^{6a}$ are each independently selected from the group consisting of:
(1) C$_{1-20}$alkyl;
(2) substituted C$_{1-20}$alkyl in which one or more substituents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) aryl S(O)$_n$, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$NOC(O)—O—, and
(t) R$^2$O—C(O)—NR$^3$—;
(3) C$_{1-20}$alkyl wherein one or more of the carbons is replaced by —NR$^3$—, —O—, or —S(O)$_n$—;
(4) substituted C$_{1-20}$alkyl wherein one or more of the carbons is replaced by —NR$^3$—, —O— or —S(O)$_n$— and wherein one or more carbon substituents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) aryl S(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;

(5) C$_{2-20}$alkenyl wherein alkenyl contains one or more double bonds;

(6) substituted C$_{2-20}$alkenyl wherein alkenyl contains one or more double bonds and wherein one or more of the carbons is substituted with:
(a) halogen
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) aryl S(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(u) OC(O)O, which forms a five membered ring:

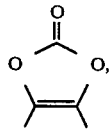

with adjacent olefinic carbons;
(7) C$_{2-20}$alkenyl wherein alkenyl contains one or more double bonds and one or more of the nonolefinic carbons is replaced by —NR$^3$—, —O— or —S(O)$_n$—;
(8) substituted C$_{2-20}$alkenyl wherein alkenyl contains one or more double bonds and one or more of the nonolefinic carbons is replaced by —NR$^3$—, —O— or —S(O)$_n$— and wherein one or more carbon substituents is selected from:
(a) halogen
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) aryl S(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(u) OC(O)O, which forms a five membered ring:

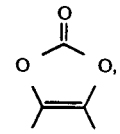

with adjacent olefinic carbons;
(9) C$_{2-20}$alkynyl wherein alkynyl contains one or more triple bonds;
(10) substituted C$_{2-20}$alkynyl wherein alkynyl contains one or more triple bonds and wherein one or more of the carbons is substituted with:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$—, wherein aryl is substituted with X and Y,
(m) R$^3$—C(O)—NR$^3$—,
(n) R$^3$R$^3$N—C(O)—,
(o) —CO$_2$H,
(p) —vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(11) C$_{2-20}$alkynyl wherein alkynyl contains one or more triple bonds and one or more of the saturated carbons is replaced by —NR$^3$—, —O— or —S(O)$_n$—;
(12) substituted C$_{2-20}$alkynyl wherein alkynyl contains one or more double bonds and one or more of the saturated carbons is replaced by —NR$^3$—, —O— or —S(O)$_n$— and wherein one or more carbon substitutents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl—,
(i) aryl substituted with X and Y,
(j) heteroaryl substituted with X and Y,
(k) heterocycloalkyl,
(l) arylS(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(13) aryl substituted with X and Y;
(14) Heteroaryl substituted with X and Y;
(15) C$_{3-5}$ cycloalkyl;
(16) substituted C$_{3-5}$ cycloalkyl in which one or more of the substituents is selected from:
(a) R$^3$O—, and
(b) R$^3$R$^3$N—; and
(17) hydrogen;
aryl including X, Y substitution is:

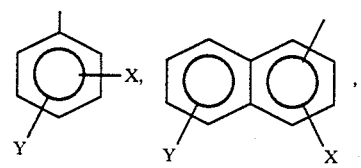

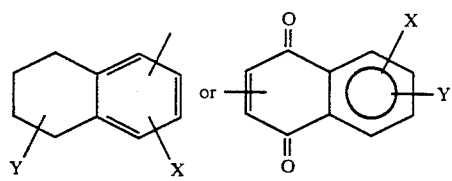

heteroaryl including X, Y substitution is selected from

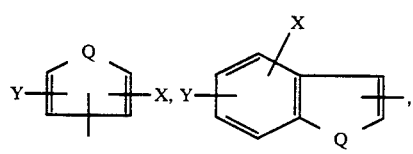

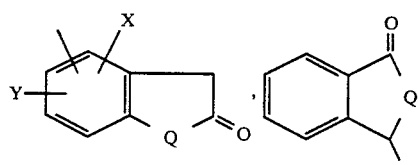

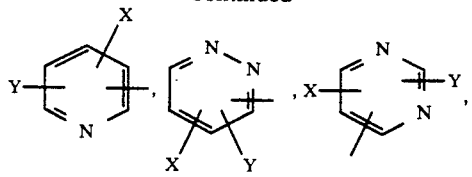

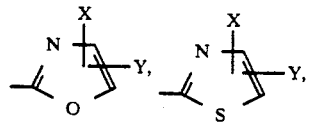

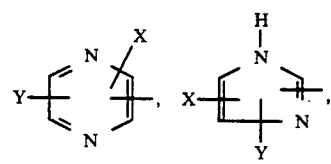

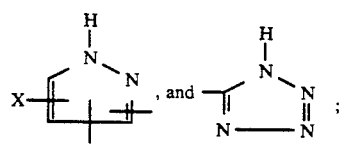

wherein: Q is —NR$^3$, —O— or —S—;
heterocycloalkyl is selected from:

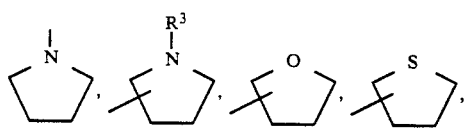

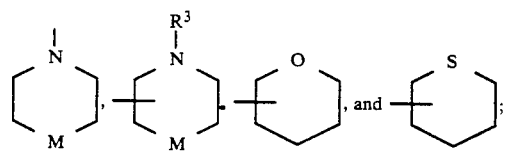

wherein: M is —NR$^3$, —O—, —S— or —CH$_2$—
X and Y are each independently selected from:
(1) hydrogen;
(2) hydroxy;
(3) halogen;
(4) trifluoromethyl;
(5) C$_{1-10}$alkyl;
(6) aryl substituted with X$^1$ and Y$^1$;
(7) R$^2$O—;
(8) arylcarbonyloxy—, wherein aryl is substituted with X$^1$ and Y$^1$;
(9) R$^3$—C(O)—O—;
(10) —CO$_2$R$^2$;
(11) —CO$_2$H; and
(12) nitro;
X$^1$ and Y$^1$ are each independently selected from:
(1) hydrogen;
(2) hydroxy;
(3) halogen;
(4) trifluoromethyl;
(5) C$_{1-4}$alkyl;
(6) R$^2$O—;
(7) R$^3$—C(O)—O—;
(8) —CO$_2$R$^2$;
(9) —CO$_2$H; and

(10) nitro;

n is 0, 1 or 2;

$Z^1$ and $Z^2$ are each independently selected from:
(1) —$OR^{6a}$;
(2) —$SR^{6a}$; and
(3) —$NR^{6a}R^{6a}$;

or a pharmaceutically acceptable salt of formula (I).

One embodiment of this invention is the compounds of formula (I) wherein:

$R^1$ is selected from the group consisting of:
(1) $C_{1-20}$alkyl;
(2) substituted $C_{1-20}$alkyl in which one or more substituents is selected from:
  (a) halogen,
  (b) hydroxy,
  (c) $R^3R^3N$—,
  (d) $R^2O$—,
  (e) $R^2O$—C(O)—,
  (f) $R^3$—C(O)—O—,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3$—C(O)—$NR^3$—,
  (n) $R^3R^3N$—C(O)—,
  (o) —$CO_2H$,
  (p) -vinylidene,
  (q) $R^3$—C(O)—,
  (r) $R^2O$—C(O)—O—,
  (s) $R^3R^3N$—C(O)—O—, and
  (t) $R^2O$—C(O)—$NR^3$—;
(3) $C_{1-20}$alkyl wherein one or more of the carbons is replaced by —$NR^3$—, —O—, or —S(O)$_n$—;
(4) substituted $C_{1-20}$alkyl wherein one or more of the carbons is replaced by —$NR^3$—, —O— or —S(O)$_n$— and wherein one or more carbon substituents is selected from:
  (a) halogen,
  (b) hydroxy,
  (c) $R^3R^3N$—,
  (d) $R^2O$—,
  (e) $R^2O$—C(O)—,
  (f) $R^3$—C(O)—O—,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3$—C(O)—$NR^3$—,
  (n) $R^3R^3N$—C(O)—,
  (o) —$CO_2H$,
  (p) -vinylidene,
  (q) $R^3$—C(O)—,
  (r) $R^2O$—C(O)—O—,
  (s) $R^3R^3N$—C(O)—O—, and
  (t) $R^2O$—C(O)—$NR^3$—;
(5) aryl substituted with X and Y;
(6) heteroaryl substituted with X and Y;
(7) $C_{2-20}$alkenyl wherein alkenyl contains one, two or three double bonds;
(8) substituted $C_{2-20}$alkenyl wherein alkenyl contains one, two or three double bonds and wherein one or more of the carbons is substituted with:
  (a) halogen,
  (b) hydroxy,
  (c) $R^3R^3N$—,
  (d) $R^2O$—,
  (e) $R^2O$—C(O)—,
  (f) $R^3$—C(O)—O—,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3$—C(O)—$NR^3$—,
  (n) $R^3R^3N$—C(O)—,
  (o) —$CO_2H$,
  (p) -vinylidene,
  (q) $R^3$—C(O)—,
  (r) $R^2O$—C(O)—O—,
  (s) $R^3R^3N$—C(O)—O—, and
  (t) $R^2O$—C(O)—$NR^3$—;
(9) $C_{2-20}$alkenyl wherein alkenyl contains one, two or three double bonds and one or more of the nonolefinic carbons is replaced by —$NR^3$—, —O— or —S(O)$_n$—; and
(10) substituted $C_{2-20}$alkenyl wherein alkenyl contains one, two or three double bonds and one or more of the nonolefinic carbons is replaced by —$NR^3$—, —O— or —S(O)$_n$— and wherein one or more carbons substituents is selected from:
  (a) halogen,
  (b) hydroxy,
  (c) $R^3R^3N$—,
  (d) $R^2O$—,
  (e) $R^2O$—C(O)—,
  (f) $R^3$—C(O)—O—,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3$—C(O)—$NR^3$—,
  (n) $R^3R^3N$—C(O)—,
  (o) —$CO_2H$,
  (p) -vinylidene,
  (q) $R^3$—C(O)—,
  (r) $R^2O$—C(O)—O—,
  (s) $R^3R^3N$—C(O)—O—, and
  (t) $R^2O$—C(O)—$NR^3$—;

each $R^2$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y; and
(9) $C_{3-10}$alkynyl;

each $R^3$ is independently selected from:

(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y;
(9) $C_{3-10}$alkynyl;
(10) hydrogen; and
(11) $C_{1-5}$alkyl substituted with $X^1$;

$R^4$ is selected from the group consisting of:
(1) $C_{1-20}$alkyl;
(2) substituted $C_{1-20}$alkyl in which one or more substituents is selected from:
 (a) halogen,
 (b) hydroxy,
 (c) $R^3R^3N-$,
 (d) $R^2O-$,
 (e) $R^2O-C(O)-$,
 (f) $R^3-C(O)-O-$,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$, wherein aryl is substituted with X and Y,
 (m) $R^3-C(O)-NR^3-$,
 (n) $R^3R^3N-C(O)-$,
 (o) $-CO_2H$,
 (p) -vinylidene,
 (q) $R^3-C(O)-$,
 (r) $R^2O-C(O)-O-$,
 (s) $R^3R^3N-C(O)-O-$, and
 (t) $R^2O-C(O)-NR^3-$;
(3) $C_{1-20}$alkyl wherein one or more of the carbons is replaced by $-NR^3-$, $-O-$, or $-S(O)n-$;
(4) substituted $C_{1-20}$alkyl wherein one or more of the carbons is replaced by $-NR^3-$, $-O-$ or $-S(O)_n-$ and wherein one or more carbon substituents is selected from:
 (a) halogen,
 (b) hydroxy,
 (c) $R^3R^3N-$,
 (d) $R^2O-$,
 (e) $R^2O-C(O)-$,
 (f) $R^3-C(O)-O-$,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$, wherein aryl is substituted with X and Y,
 (m) $R^3-C(O)-NR^3-$,
 (n) $R^3R^3N-C(O)-$,
 (o) $-CO_2H$,
 (p) -vinylidene,
 (q) $R^3-C(O)-$,
 (r) $R^2O-C(O)-O-$,
 (s) $R^3R^3N-C(O)-O-$, and
 (t) $R^2O-C(O)-NR^3-$;
(5) aryl substituted with X and Y;
(6) heteroaryl substituted with X and Y;
(7) $C_{2-20}$alkenyl wherein alkenyl contains one, two or three double bonds;
(8) substituted $C_{2-20}$alkenyl wherein alkenyl contains one, two or three double bonds and wherein one or more of the carbons is substituted with:
 (a) halogen,
 (b) hydroxy,
 (c) $R^3R^3N-$,
 (d) $R^2O-$,
 (e) $R^2O-C(O)-$,
 (f) $R^3-C(O)-O-$,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$, wherein aryl is substituted with X and Y,
 (m) $R^3-C(O)-NR^3-$,
 (n) $R^3R^3N-C(O)-$,
 (o) $-CO_2H$,
 (p) -vinylidene,
 (q) $R^3-C(O)-$,
 (r) $R^2O-C(O)-O-$,
 (s) $R^3R^3N-C(O)-O-$, and
 (t) $R^2O-C(O)-NR^3-$;
(9) $C_{2-20}$alkenyl wherein alkenyl contains one, two or three double bonds and one or more of the nonolefinic carbons is replaced by $-NR^3-$, $-O-$, or $-S(O)_n-$;
(10) substituted $C_{2-20}$alkenyl wherein alkenyl contains one, two or three double bonds and one or more of the nonolefinic carbons is replaced by $-NR^3-$, $-O-$ or $-S(O)_n-$ and wherein one or more carbon substitutents is selected from:
 (a) halogen,
 (b) hydroxy,
 (c) $R^3R^3N-$,
 (d) $R^2O-$,
 (e) $R^2O-C(O)-$,
 (f) $R^3-C(O)-O-$,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$, wherein aryl is substituted with X and Y,
 (m) $R^3-C(O)-NR^3-$,
 (n) $R^3R^3N-C(O)-$,
 (o) $-CO_2H$,
 (p) -vinylidene,
 (q) $R^3-C(O)-$,
 (r) $R^2O-C(O)-O-$,
 (s) $R^3R^3N-C(O)-O-$, and
 (t) $R^2O-C(O)-NR^3-$; and
(11) hydrogen;

$R^5$ is selected from the group consisting of:
(1) hydrogen;
(2) $C_{1-10}$alkyl;
(3) aryl substituted with X and Y;
(4) aryl$C_{1-4}$alkyl, wherein aryl is substituted with X and Y;
(5) $R^2O-C(O)-$;
(6) $C_{3-10}$cycloalkyl;
(7) $R^2-C(O)-$; and (8) R³R³N—C(O)—;

R⁶ and R⁶ᵃ are each independently selected from the group consisting of:
(1) $C_{1-20}$alkyl;
(2) substituted $C_{1-20}$alkyl in which one or more substituents is selected from:
   (a) halogen,
   (b) hydroxy,
   (c) R³R³N—,
   (d) R²O—,
   (e) R²O—C(O)—,
   (f) R³—C(O)—O—,
   (g) oxo,
   (h) $C_{3-10}$cycloalkyl,
   (i) aryl substituted with X and Y,
   (j) heteroaryl substituted with X and Y,
   (k) heterocycloalkyl,
   (l) aryl S(O)n, wherein aryl is substituted with X and Y,
   (m) R³—C(O)—NR³—,
   (n) R³R³N—C(O)—,
   (o) —CO₂H,
   (p) -vinylidene,
   (q) R³—C(O)—,
   (r) R²O—C(O)—O—,
   (s) R³R³NC(O)—O—, and
   (t) R²O—C(O)—NR³—;
(3) $C_{1-20}$alkyl wherein one or more of the carbons is replaced by —NR³—, —O—, or —S(O)$_n$—;
(4) substituted $C_{1-20}$alkyl wherein one or more of the carbons is replaced by —NR³—, —O— or —S(O)$_n$— and wherein one or more carbon substituents is selected from:
   (a) halogen,
   (b) hydroxy,
   (c) R³R³N—,
   (d) R²O—,
   (e) R²O—C(O)—,
   (f) R³—C(O)—O—,
   (g) oxo,
   (h) $C_{3-10}$cycloalkyl,
   (i) aryl substituted with X and Y,
   (j) heteroaryl substituted with X and Y,
   (k) heterocycloalkyl,
   (l) aryl S(O)$_n$—, wherein aryl is substituted with X and Y,
   (m) R³—C(O)—NR³—,
   (n) R³R³N—C(O)—,
   (o) —CO₂H,
   (p) -vinylidene,
   (q) R³—C(O)—,
   (r) R²O—C(O)—O—,
   (s) R³R³N—C(O)—O—, and
   (t) R²O—C(O)—NR³—;
(5) $C_{2-20}$alkenyl wherein alkenyl contains one, two or three double bonds;
(6) substituted $C_{2-20}$alkenyl wherein alkenyl contains one, two or three double bonds and wherein one or more of the carbons is substituted with:
   (a) halogen
   (b) hydroxy,
   (c) R³R³N—,
   (d) R²O—,
   (e) R²O—C(O)—,
   (f) R³—C(O)—O—,
   (g) oxo,
   (h) $C_{3-10}$cycloalkyl,
   (i) aryl substituted with X and Y,
   (j) heteroaryl substituted with X and Y,
   (k) heterocycloalkyl,
   (l) aryl S(O)$_n$—, wherein aryl is substituted with X and Y,
   (m) R³—C(O)—NR³—,
   (n) R³R³N—C(O)—,
   (o) —CO₂H,
   (p) -vinylidene,
   (q) R³—C(O)—,
   (r) R²O—C(O)—O—,
   (s) R³R³N—C(O)—O—, and
   (t) R²O—C(O)—NR³—;
(u) OC(O)O, which forms a five membered ring:

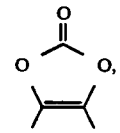

with adjacent olefinic carbons;
(7) $C_{2-20}$alkenyl wherein alkenyl contains one, two or three double bonds and one or more of the nonolefinic carbons is replaced by —NR³—, —O— or —S(O)$_n$—;
(8) substituted $C_{2-20}$alkenyl wherein alkenyl contains one, two or three double bonds and one or more of the nonolefinic carbons is replaced by —NR³—, —O— or —S(O)$_n$— and wherein one or more carbon substituents is selected from:
   (a) halogen (b) hydroxy,
   (c) R³R³N—,
   (d) R²O—,
   (e) R²O—C(O)—,
   (f) R³—C(O)—O—,
   (g) oxo,
   (h) $C_{3-10}$cycloalkyl,
   (i) aryl substituted with X and Y,
   (j) heteroaryl substituted with X and Y,
   (k) heterocycloalkyl,
   (l) aryl S(O)$_n$—, wherein aryl is substituted with X and Y,
   (m) R³—C(O)—NR³—,
   (n) R³R³N—C(O)—,
   (o) —CO₂H,
   (p) -vinylidene,
   (q) R³—C(O)—,
   (r) R²O—C(O)—O—,
   (s) R³R³N—C(O)—O—, and
   (t) R²O—C(O)—NR³—;
(u) OC(O)O, which forms a five membered ring:

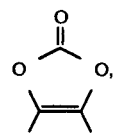

with adjacent olefinic carbons;
(9) $C_{2-20}$alkynyl wherein alkynyl contains one or more triple bonds;
(10) substituted $C_{2-20}$alkynyl wherein alkynyl contains one or more triple bonds and wherein one or more of the carbons is substituted with:

(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;

(11) $C_{2-20}$alkynyl wherein alkynyl contains one or more triple bonds and one or more of the saturated carbons is replaced by $-NR^3-$, $-O-$ or $-S(O)_n-$;

(12) substituted $C_{2-20}$alkynyl wherein alkynyl contains one or more triple bonds and one or more of the saturated carbons is replaced by $-NR^3-$, $-O-$ or $-S(O)_n-$ and wherein one or more carbon substitutents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl-,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;

(13) aryl substituted with X and Y;
(14) heteroaryl substituted with X and Y;
(15) $C_{3-5}$ cycloalkyl;
(16) substituted $C_{3-5}$ cycloalkyl in which one or more of the substituents is selected from:
(a) $R^3O-$, and
(b) $R^3R^3N-$; and
(17) hydrogen;

aryl including X, Y substitution is

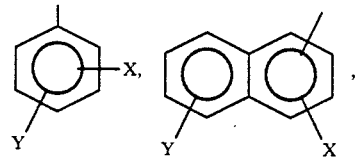

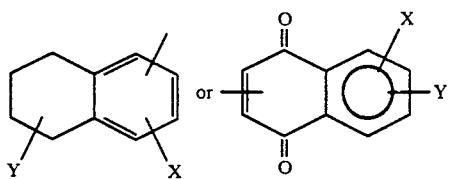

heteroaryl including X, Y substitution is selected from

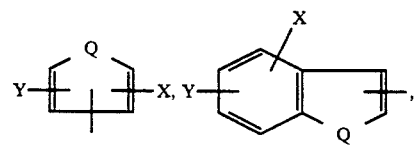

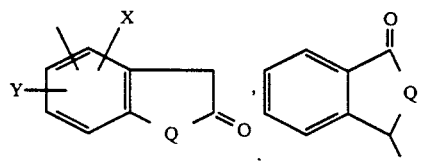

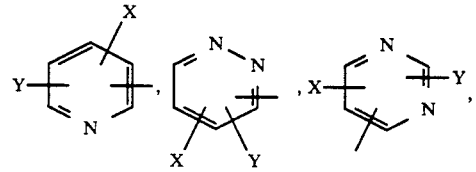

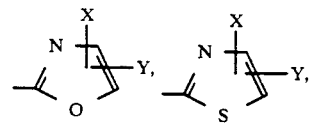

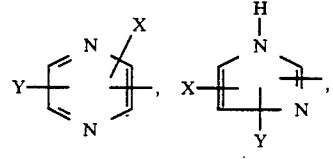

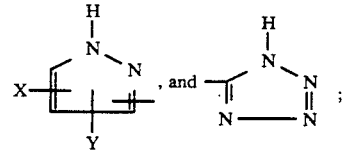

wherein: Q is $-NR^3$, $-O-$ or $-S-$;
heterocycloalkyl is selected from:

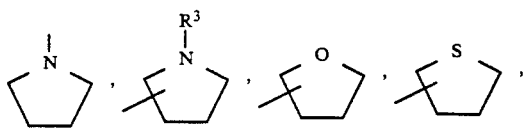

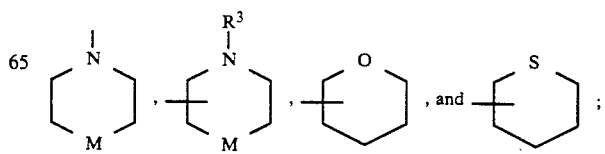

-continued wherein: M is —NR³—, —O—, —S— or —CH₂—
X and Y are each independently selected from:
(1) hydrogen;
(2) hydroxy;
(3) halogen;
(4) trifluoromethyl;
(5) $C_{1-10}$alkyl;
(6) aryl substituted with $X^1$ and $Y^1$;
(7) $R^2O$—;
(8) arylcarbonyloxy-, wherein aryl is substituted with $X^1$ and $Y^1$;
(9) $R^3$—C(O)—O—;
(10) —$CO_2R^2$;
(11) —$CO_2H$; and
(12) nitro;
$X^1$ and $Y^1$ are each independently selected from:
(1) hydrogen;
(2) hydroxy;
(3) halogen;
(4) trifluoromethyl;
(5) $C_{1-4}$alkyl;
(6) $R^2O$—;
(7) $R^3$—C(O)—O—;
(8) —$CO_2R^2$;
(10) —$CO_2H$; and
(11) nitro;
n is 0, 1 or 2;
$Z^1$ and $Z^2$ are each independently selected from:
(1) —$OR^{6a}$;
(2) —$SR^{6a}$; and
(3) —$NR^{6a}R^{6a}$;
provided that when $R^5$ and $R^6$ are H, and $R^1$ and $R^4$—(A)$_a$— are both respectively

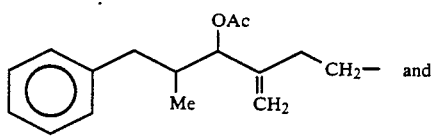 and

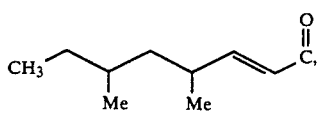

then $Z^1$ and $Z^2$ are not OH or $OCH_3$; and further provided that when $R^5$ and $R^6$ are H, and $R^1$ and $R^4$—(A)$_a$— are both respectively

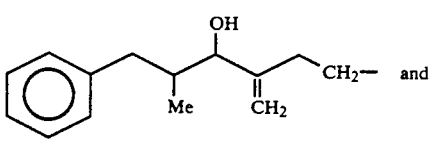 and

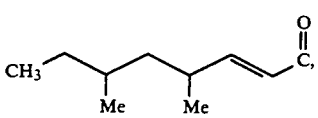

then $Z^1$ and $Z^2$ are not OH;
or a pharmaceutically acceptable salt of formula (I).
One class of this embodiment is the compound of formula (I) wherein:

$R^1$ is selected from the group consisting of:
(1) $C_{1-20}$alkyl;
(2) substituted $C_{1-20}$alkyl in which one or more substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(3) $C_{1-20}$alkyl wherein one or more of the carbons is replaced by —$NR^3$—, —O—, or —$S(O)_n$—;
(4) substituted $C_{1-20}$alkyl wherein one or more of the carbons is replaced by —$NR^3$—, —O— or —$S(O)_n$— and wherein one or more carbon substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(5) aryl substituted with X and Y;
(6) heteroaryl substituted with X and Y;
(7) $C_{2-20}$alkenyl wherein alkenyl contains one, two or three double bonds;
(8) substituted $C_{2-20}$alkenyl wherein alkenyl contains one, two or three double bonds and wherein one or more of the carbons is substituted with:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl, (i) aryl substituted with X and Y,
(j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(9) $C_{2-20}$alkenyl wherein alkenyl contains one, two or three double bonds and one or more of the nonolefinic carbons is replaced by —$NR^3$—, —O— or —S(O)$_n$—;
(10) substituted $C_{2-20}$alkenyl wherein alkenyl contains one, two or three double bonds and one or more of the nonolefinic carbons is replaced by —$NR^3$, —O— or —S(O)$_n$— and wherein one or more carbons substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;

each $R^2$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y; and
(9) $C_{3-10}$alkynyl;

each $R^3$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y;
(9) $C_{3-10}$alkynyl;
(10) hydrogen; and
(11) $C_{1-5}$alkyl substituted with $X^1$;

$R^4$ is selected from the group consisting of:
(1) $C_{1-20}$alkyl;
(2) substituted $C_{1-20}$alkyl in which one or more substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(3) $C_{1-20}$alkyl wherein one or more of the carbons is replaced by —$NR^3$—, —O—, or —S(O)$_n$—;
(4) substituted $C_{1-20}$alkyl wherein one or more of the carbons is replaced by —$NR^3$—, —O— or —S(O)$_n$— and wherein one or more carbon substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(5) aryl substituted with X and Y;
(6) heteroaryl substituted with X and Y;
(7) $C_{2-20}$ alkenyl wherein alkenyl contains one, two or three double bonds;
(8) substituted $C_{2-20}$ alkenyl wherein alkenyl contains one, two or three double bonds and wherein one or more of the carbons is substituted with:
(a) halogen,
(b) hydroxy,
(c) $R^3R^3N$—, (d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;

(9) $C_{2-20}$alkenyl wherein alkenyl contains one, two or three double bonds and one or more of the nonolefinic carbons is replaced by $-NR^3-$, $-O-$ or $-S(O)_n-$;

(10) substituted $C_{2-20}$alkenyl wherein alkenyl contains one, two or three double bonds and one or more of the nonolefinic carbons is replaced by $-NR^3-$, $-O-$ or $-S(O)_n-$ and wherein one or more carbon substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$; and

(11) hydrogen;

$R^5$ is selected from the group consisting of:
(1) hydrogen;
(2) $C_{1-10}$alkyl;
(3) aryl substituted with X and Y;
(4) aryl $C_{1-4}$alkyl, wherein aryl is substituted with X and Y;
(5) $R^2O-C(O)-$;
(6) $C_{3-10}$cycloalkyl;
(7) $R^2-C(O)-$; and
(8) $R^3R^3N-C(O)-$;

$R^6$ and $R^{6a}$ are each independently selected from the group consisting of:
(1) $C_{1-20}$alkyl;
(2) substituted $C_{1-20}$alkyl in which one or more substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) aryl S(O)n, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3NOC(O)-O-$, and
(t) $R^2O-C(O)-NR^3-$;

(3) $C_{1-20}$alkyl wherein one or more of the carbons is replaced by $-NR^3-$, $-O-$, or $-S(O)_n-$;

(4) substituted $C_{1-20}$alkyl wherein one or more of the carbons is replaced by $-NR^3-$, $-O-$ or $-S(O)_n-$ and wherein one or more carbon substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;

(5) $C_{2-20}$alkenyl wherein alkenyl contains one, two or three double bonds;

(6) substituted $C_{2-20}$alkenyl wherein alkenyl contains one, two or three double bonds and wherein or more of the carbons is substituted with:
(a) halogen
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$, (r) $R^2O-C(O)-O-$,
(s) $R^3R^3N-C(O)-O-$, and
(t) $R^2O-C(O)-NR^3-$;
(u) $OC(O)O$, which forms a five membered ring:

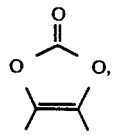

with adjacent olefinic carbons;
(7) $C_{2-20}$alkenyl wherein alkenyl contains one, two or three double bonds and one or more of the nonolefinic carbons is replaced by $-NR^3-$, $-O-$ or $-S(O)_n-$;
(8) substituted $C_{2-20}$alkenyl wherein alkenyl contains one, two or three double bonds and one or more of the nonolefinic carbons is replaced by $-NR^3-$, $-O-$ or $-S(O)_n-$ and wherein one or more carbon substituents is selected from:
(a) halogen
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(u) $OC(O)O$, which forms a five membered ring:

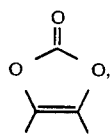

with adjacent olefinic carbons;
(9) $C_{2-20}$alkynyl wherein alkynyl contains one, two or three triple bonds;
(10) substituted $C_{2-20}$alkynyl wherein alkynyl contains one, two or three triple bonds and wherein one or more of the carbons is substituted with:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(11) $C_{2-20}$alkynyl wherein alkynyl contains one, two or three triple bonds and one or more of the saturated carbons is replaced by $-NR^3-$, $-O-$ or $-S(O)_n-$;
(12) substituted $C_{2-20}$alkynyl wherein alkynyl contains one, two or three triple bonds and one or more of the saturated carbons is replaced by $-NR^3-$, $-O-$ or $-S(O)_n-$ and wherein one or more carbon substitutents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl-,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(13) aryl substituted with X and Y;
(14) Heteroaryl substituted with X and Y;
(15) $C_{3-5}$ cycloalkyl;
(16) substituted $C_{3-5}$ cycloalkyl in which one or more of the substituents is selected from:
(a) $R^3O-$, and
(b) $R^3R^3N-$; and
(17) hydrogen;
aryl is phenyl with X and Y substitution or

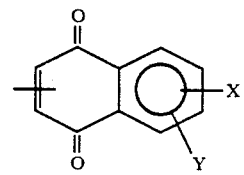

heteroaryl including X, Y substitution is selected from:

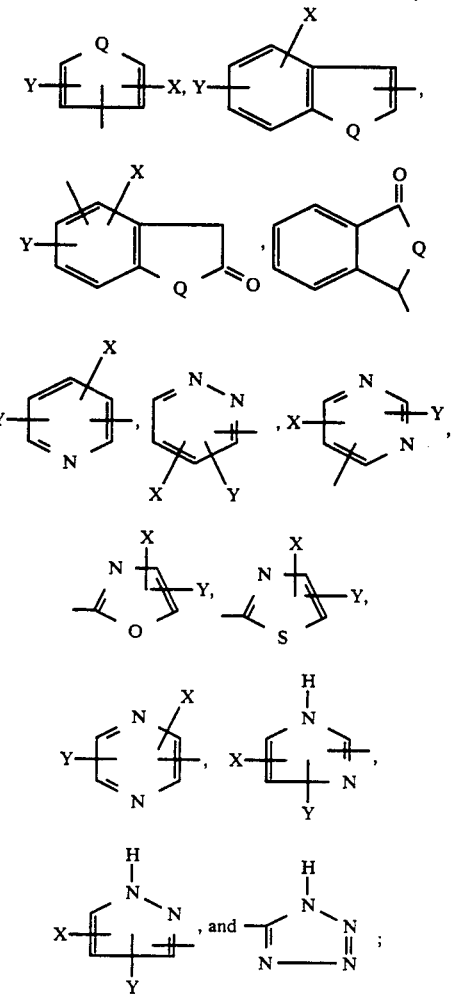

wherein: Q is —NR³, —O— or —S—;
heterocycloalkyl is selected from:

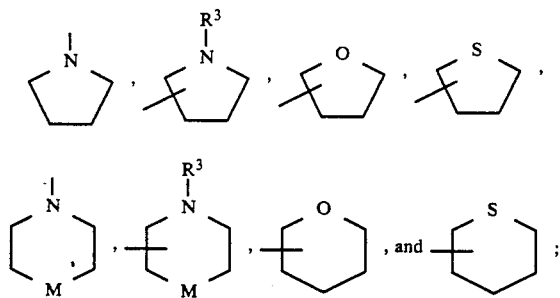

wherein: M is —NR³, —O—, —S— or —CH₂—
X and Y are each independently selected from:
(1) hydrogen;
(2) hydroxy;
(3) halogen;
(4) trifluoromethyl;
(5) $C_{1-10}$alkyl;
(6) aryl substituted with $X^1$ and $Y^1$;
(7) $R^2O$—;
(8) arylcarbonyloxy-, wherein aryl is substituted with $X^1$ and $Y^1$;
(9) $R^3$—C(O)—O—;
(10) —$CO_2R^2$;
(11) —$CO_2H$; and
(12) nitro;

$X^1$ and $Y^1$ are each independently selected from:
(1) hydrogen;
(2) hydroxy;
(3) halogen;
(4) trifluoromethyl;
(5) $C_{1-4}$alkyl;
(6) $R^2O$—;
(7) $R^3$—C(O)—O—;
(8) —$CO_2R^2$;
(9) —$CO_2H$; and
(10) nitro;

n is 0, 1 or 2;

$Z^1$ and $Z^2$ are each independently selected from:
(1) —$OR^{6a}$;
(2) —$SR^{6a}$; and
(3) —$NR^{6a}R^{6a}$;

provided that when $R^5$ and $R^6$ are H, and $R^1$ and $R^4$—(A)$_a$— are both respectively

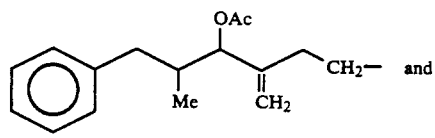

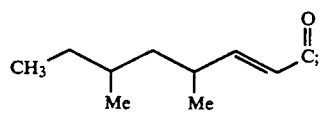

then $Z^1$ and $Z^2$ are not OH or $OCH_3$; and further provided that when $R^5$ and $R^6$ are H, and $R^1$ and $R^4$—(A)$_a$— are both respectively

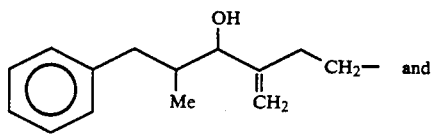

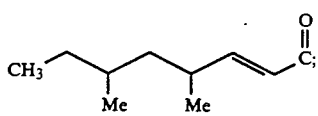

then $Z^1$ and $Z^2$ are not OH;
or a pharmaceutically acceptable salt of formula (I).

In a further class of this embodiment are those compounds of formula (I) wherein:

$R^1$ is selected from the group consisting of:
(1) $C_{2-16}$alkyl;
(2) substituted $C_{2-16}$alkyl in which one or more substituents is selected from:
(a) hydroxy,
(b) $R^2O$—,
(c) $R^2O$—C(O)—,
(d) $R^3$—C(O)—O—,
(e) oxo,
(f) $C_{3-10}$cycloalkyl,
(g) aryl substituted with X and Y,
(h) $R^3R^3N$—C(O)—,
(i) —$CO_2H$,
(j) -vinylidene, (k) $R^3$—C(O)—,
(l) $R^2O$—C(O)—O—, and
(m) $R^3R^3N$—C(O)—O—;
(3) $C_{2-16}$alkyl wherein one of the carbons is replaced by —$NR^3$—, —O—, or —S(O)$_n$—;
(4) substituted $C_{2-16}$alkyl wherein one of the carbons is replaced by —$NR^3$—, —O— or —S(O)$_n$— and wherein one or more carbon substituents is selected from:
(a) hydroxy,
(b) $R^2O$—,
(c) $R^2O$—C(O)—,
(d) $R^3$—C(O)—O—,
(e) oxo,
(f) $C_{3-10}$cycloalkyl,
(g) aryl substituted with X and Y,
(h) $R^3R^3N$—C(O)—,
(i) —$CO_2H$,
(j) -vinylidene,
(k) $R^3$—C(O)—,
(l) $R^2O$—C(O)—O—, and
(m) $R^3R^3N$—C(O)—O—;
(5) $C_{2-16}$alkenyl wherein alkenyl contains one, two or three double bonds;
(6) substituted $C_{2-16}$alkenyl wherein alkenyl contains one, two or three double bonds and wherein one or more of the carbons is substituted with:
(a) hydroxy,
(b) $R^2O$—,
(c) $R^2O$—C(O)—,
(d) $R^3$—C(O)—O—,
(e) oxo,
(f) $C_{3-10}$cycloalkyl,
(g) aryl substituted with X and Y,
(h) $R^3R^3N$—C(O)—,
(i) —$CO_2H$,
(j) -vinylidene,
(k) $R^3$—C(O)—,
(l) $R^2O$—C(O)—O—, and
(m) $R^3R^3N$—C(O)—O—;
(7) $C_{2-16}$alkenyl wherein alkenyl contains one, two or three double bonds and one or more of the nonolefinic carbons is replaced by —$NR^3$—, —O— or —S(O)$_n$—; and
(8) substituted $C_{2-16}$alkenyl wherein alkenyl contains one, two or three double bonds and one or more of the nonolefinic carbons is replaced by —$NR^3$, —O— or —S(O)$_n$— and wherein one or more carbons substituents is selected from:
(a) hydroxy,
(b) $R^2O$—,
(c) $R^2O$—C(O)—,
(d) $R^3$—C(O)—O—,
(e) oxo,
(f) $C_{3-10}$cycloalkyl,
(g) aryl substituted with X and Y,
(h) $R^3R^3N$—C(O)—,
(i) —$CO_2H$,
(j) -vinylidene,
(k) $R^3$—C(O)—,
(l) $R^2O$—C(O)—O—, and
(m) $R^3R^3N$—C(O)—O—;
each $R^2$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl; and
(8) aryl$C_{2-10}$alkenyl wherein aryl is substituted with X and Y;
each $R^3$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y; and
(9) hydrogen;
$R^4$ is selected from the group consisting of:
(1) $C_{1-20}$alkyl;
(2) substituted $C_{1-20}$alkyl in which one or more substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,.
(r) $R^2O$—C(O)—O—,
(s) $R^3R^3N$—C(O)—O—, and
(t) $R^2O$—C(O)—$NR^3$—;
(3) $C_{1-20}$alkyl wherein one or more of the carbons is replaced by —$NR^3$—, —O—, or —S(O)$_n$—;
(4) substituted $C_{1-20}$alkyl wherein one or more of the carbons is replaced by —$NR^3$—, —O— or —S(O)$_n$— and wherein one or more carbon substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—;

(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(5) aryl substituted with X and Y;
(6) C$_{2-20}$ alkenyl wherein alkenyl contains one, two or three double bonds;
(7) substituted C$_{2-20}$ alkenyl wherein alkenyl contains one, two or three double bonds and wherein one or more of the carbons is substituted with:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—; and
(8) hydrogen;
R$^5$ is selected from the group consisting of:
(1) hydrogen;
(2) C$_{1-3}$alkyl; and
(3) R$^2$—C(O)—;
R$^6$ is selected from the group consisting of:
(1) C$_{1-20}$alkyl;
(2) substituted C$_{1-20}$alkyl in which one or more substituents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) R$^3$—C(O)—NR$^3$—,
(m) R$^3$R$^3$N—C(O)—,
(n) —CO$_2$H, and
(o) R$^2$O—C(O)—NR$^3$—;
(3) C$_{1-20}$alkyl wherein one or more of the carbons is replaced by —NR$^3$—, —O—, or —S(O)$_n$—;
(4) substituted C$_{1-20}$alkyl wherein one or more of the carbons is replaced by —NR$^3$—, —O—, or —S(O)$_n$— and wherein one or more carbon substituents is selected from:
(a) halogen,
(b) hydroxy,
(c) R$^3$R$^3$N—,
(d) R$^2$O—, (e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) R$^3$—C(O)—NR$^3$—,
(m) R$^3$R$^3$N—C(O)—,
(n) —CO$_2$H, and
(o) R$^2$O—C(O)—NR$^3$—;
(5) C$_{2-20}$alkenyl wherein alkenyl contains one or more double bonds;
(6) substituted C$_{2-20}$alkenyl wherein alkenyl contains one or more double bonds and wherein one or more of the carbons is substituted with:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) R$^3$—C(O)—NR$^3$—,
(m) R$^3$R$^3$N—C(O)—,
(n) —CO$_2$H, and
(o) R$^2$O—C(O)—NR$^3$—;
(p) OC(O)O, which forms a five membered ring:

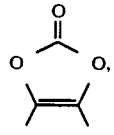

with adjacent olefinic carbons;
(7) C$_{2-20}$alkynyl wherein alkynyl contains one or more triple bonds;
(8) substituted C$_{2-20}$alkynyl wherein alkynyl contains one or more triple bonds and wherein one or more of the carbons is substituted with:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) R$^3$—C(O)—NR$^3$—,
(m) R$^3$R$^3$N—C(O)—;
(n) —CO$_2$H, and
(o) R$^2$O—C(O)—NR$^3$—;
(9) aryl substituted with X and Y;
(10) heteroaryl substituted with X and Y;
(11) C$_{3-5}$ cycloalkyl;
(12) substituted C$_{3-5}$ cycloalkyl in which one or more of the substituents is selected from:
(a) R$^3$O—, and (b) R³R³N—; and
(13) hydrogen;
aryl is phenyl with X and Y substitution or

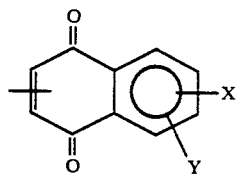

heteroaryl including X, Y substitution is:

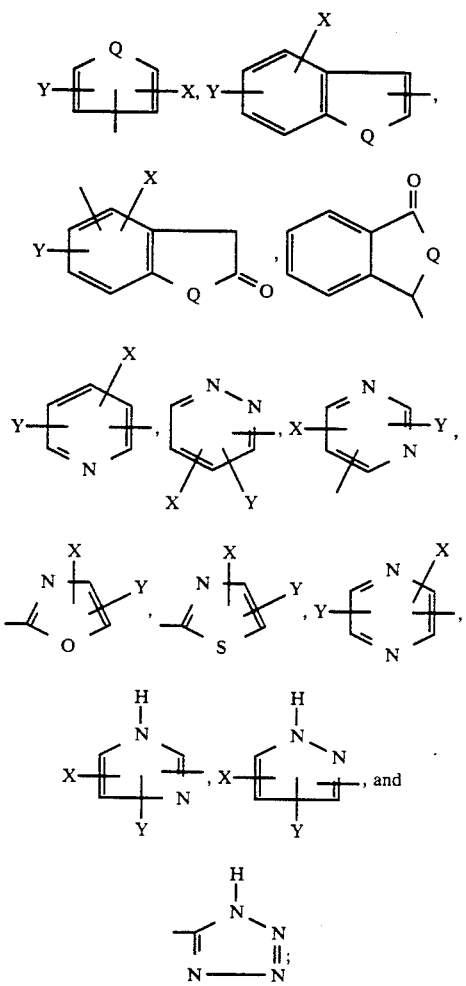

wherein: Q is —NR³, —O— or —S—;
heterocycloalkyl is:

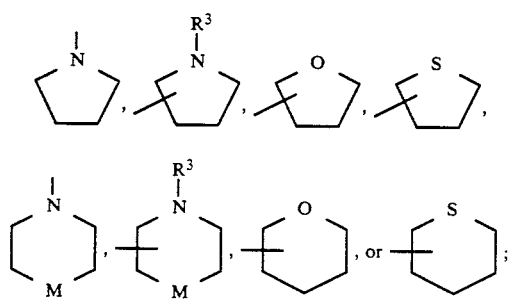

wherein: M is —NR³, —O—, —S— or —CH₂—
X and Y are each independently selected from:
(1) hydrogen;
(2) hydroxy;
(3) halogen;
(4) trifluoromethyl;
(5) $C_{1-10}$alkyl;
(6) aryl substituted with $X^1$ and $Y^1$;
(7) $R^2O$—;
(8) arylcarbonyloxy—, wherein aryl is substituted with $X^1$ and $Y^1$;
(9) $R^3$—C(O)—O—;
(10) —$CO_2R^2$;
(11) —$CO_2H$; and
(12) nitro;
$X^1$ and $Y^1$ are each independently selected from:
(1) hydrogen;
(2) hydroxy;
(3) halogen;
(4) trifluoromethyl;
(5) $C_{1-4}$alkyl;
(6) $R^2O$—;
(7) $R^3$—C(O)—O—;
(8) —$CO_2R^2$;
(10) —$CO_2H$; and
(11) nitro;
n is 0, 1 or 2;
$Z^1$ and $Z^2$ are each independently selected from:
(1) —$OR^6$;
(2) —$SR^6$; and
(3) —$NR^6R^6$;
provided that when $R^5$ and $R^6$ are H, and $R^1$ and $R^4$—(A)$_a$— are both respectively

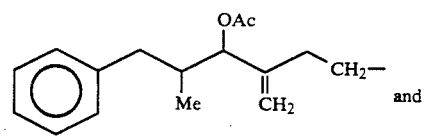

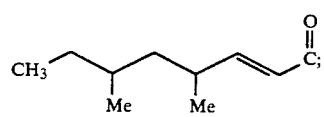

then $Z^1$ and $Z^2$ are not OH or $OCH_3$; and further provided that when $R^5$ and $R^6$ are H, and $R^1$ and $R^4$—(A)$_a$— are both respectively

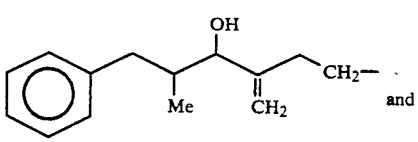

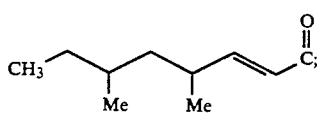

then $Z^1$ and $Z^2$ are not OH;
or a pharmaceutically acceptable salt.

Except where specifically defined to the contrary the terms alkyl, alkenyl, alkynyl, alkoxy and acyl include both the straight-chain and branched chain species of the term. The term cycloalkyl includes both monocyclic and polycyclic species. Where two Markush groups are bonded to the same atom, e.g. $R^3R^3N$, these groups may take on the same value e.g. $(CH_3)_2N$ or different values within the markush group, e.g. $CH_3NH$. Similarly each Markush group, such as $R^3$, within a compound of formula (I) is selected independently, e.g. $R^3R^3N—$ may be $NH_2—$ while $R^3—C(O)—O—$ is $CH_3—C(O)—O—$.

One subclass of this embodiment is the compound of formula I with subgeneric formula (III) and wherein $R^4—(A)_a$, $R^3$ and $R^6$ are selected from the group described in Table 1 below:

TABLE 1

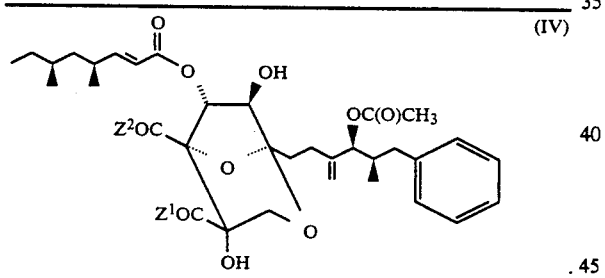

(III)

| Compound # | $R^4—(A)_a—$ | $R^6$ | $R^3$ |
|---|---|---|---|
| 1a | $Ph(CH_2)_3CH(CH_3)CHCH(CH_2)_2C(O)$ | H | $C(O)CH_3$ |
| 1b | $CH_3(CH_2)_{12}C(O)$ | H | $C(O)CH_3$ |
| 1c | $PhO(CH_2)_{10}C(O)$ | H | $C(O)CH_3$ |
| 1d | $CH_3(CH_2)_{11}NHC(O)$ | H | $C(O)CH_3$ |
| 1e | $CH_3(CH_2)_{11}NHC(O)$ | $C(O)NH(CH_2)_{11}CH_3$ | $C(O)CH_3$ |
| 1f | H | H | H |

In a second subclass of this embodiment are the compounds of formula (I), with subgeneric formula (IV) and wherein $Z^1$ and $Z^2$ are selected from the group described in Table 2 below:

TABLE 2

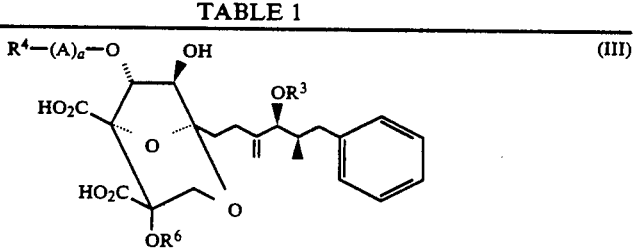

(IV)

| Compound # | $Z^1$ | $Z^2$ |
|---|---|---|
| 2a | $OCH(CH_3)OCO_2CH_2CH_3$ | OH |
| 2b | $OCH(CH_3)OCOC(CH_3)_3$ | OH |

TABLE 2-continued

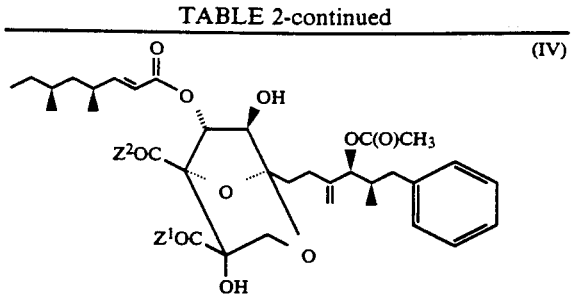

(IV)

| Compound # | $Z^1$ | $Z^2$ |
|---|---|---|
| 2c | (cyclic structure with $CH_3$, O, O, O shown) | OH |
| 2d | $OCH_2OC(O)C(CH_3)_3$ | OH |

In a third subclass of this embodiment are the compounds of formula (I), with subgeneric formula (V) and wherein $R^4—(A)_a$, $Z_1$ and $Z_2$ are selected from the group described in Table 3 below:

TABLE 3

(V)

| Compound # | $R^4—(A)_a—$ | $Z^1$ | $Z^2$ |
|---|---|---|---|
| 3a | $CH_3(CH_2)_{12}C(O)$ | OH | $OCH_2OC(O)C(CH_3)_3$ |
| 3b | $CH_3(CH_2)_{12}C(O)$ | $OCH_2OC(O)C(CH_3)_3$ | $OCH_2OC(O)C(CH_3)_3$ |
| 3c | $CH_3(CH_2)_{12}C(O)$ | $OCH_2OC(O)C(CH_3)_3$ | OH |
| 3d | $PhO(CH_2)_{10}C(O)$ | OH | $OCH_2OC(O)C(CH_3)_3$ |
| 3e | $PhO(CH_2)_{10}C(O)$ | $OCH_2OC(O)C(CH_3)_3$ | OH |
| 3f | $PhO(CH_2)_{10}C(O)$ | $OCH_2OC(O)C(CH_3)_3$ | $OCH_2OC(O)C(CH_3)_3$ |

In a fourth subclass of this embodiment are the compounds of formula (I), with subgeneric formula (VI), and wherein $R^1$ and $Z^1$ are selected from the group described in Table 4 below:

TABLE 4

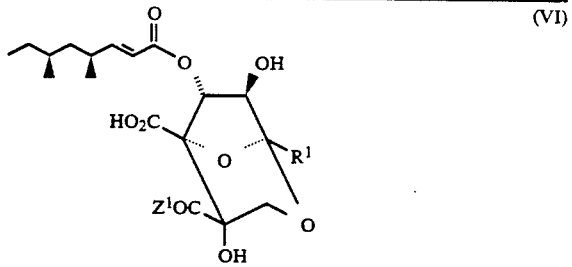

(VI)

| Compound # | R$^1$ | Z$^1$ |
|---|---|---|
| 4a | CH$_2$CH$_2$C(CH$_2$)CH(OH)CH(CH$_3$)CH$_2$Ph | OH |
| 4b | CH$_2$CH$_2$C(CH$_2$)CH(OCOnPr)CH(CH$_3$)CH$_2$Ph | OH |
| 4c | CH$_2$CH$_2$C(CH$_2$)CH(OCOnPr)CH(CH$_3$)CH$_2$Ph | OCH$_2$OC(O)C(CH$_3$)$_3$ |
| 4d | CH$_2$CH$_2$C(CH$_2$)CH(OCOPh)CH(CH$_3$)CH$_2$Ph | OH |
| 4e | CH$_2$CH$_2$C(CH$_2$)CH(OCOPh)CH(CH$_3$)CH$_2$Ph | OCH$_2$OC(O)C(CH$_3$)$_3$ |

The compounds of formula I can be prepared from (1S,3S,4S,5R,6R,7R)-1-[(4S)-acetoxy-3-methylene-5-methyl-6-phenyl]hexyl-4,6,7-trihydroxy-6-O-(4,6-dimethyl-2-octenoyl)-2,8-dioxabicyclo[3.2.1]octane-3,4,5-tricarboxylic acid (IA), (1S,3S,4S,5R,6R,7R-)-1-[(4-)-hydroxy-3,5-dimethyl-8-phenyl]oct-7-enyl-4,6,7-trihydroxy-6-O-(tetradeca-6,12-dienoyl)-2,8-dioxabicyclo[3.2.1]octane-3,4,5-tricarboxylic acid (IB), or (1S,3S,4S,5R,6R,7R)-1-[(4)-acetoxy-5-methyl-6-phenyl]hexyl-4,6,7-trihydroxy-6-O-(6-methyl-9-phenyl-4-nonenoyl)-2,8-dioxabicyclo[3.2.1]octane-3,4,5-tricarboxylic acid (IC) by first removing the 3-carboxy moiety of IA, IB or IC, and then following the sequences described in Schemes A-I. The preparation of the starting materials, IA, IB and IC, are described in U.S. Pat. Nos. 5,096,923; 5,055,487; and 5,102,907; respectively.

To remove the 3-carboxy moiety of IA, the methodology of Scheme 1 is followed. The 3-carboxy group of IA is selectively esterified to form, for example, the benzyl ester followed by blocking the 4 and 5 carboxyl groups using O-t-butyl-N,N'-diisopropyl urea followed by selective removal of the 3-benzyl ester to yield the 4,5-di-t-butyl ester of IA. This is followed by formation of the 3-phenylseleno ester and then removal of the seleno ester moiety employing tributyl tin hydide, to yield the 3-descarboxy compound. The 4,5-t-butyl blocking groups are then removed under standard conditions to yield IIA.

The 3-descarboxy compounds of IB and IC can be similarly prepared utilizing the same methodology. The 3-descarboxy compounds of IA, IB and IC will hereafter be referred to as IIA, IIB and IIC, respectively. Once the 3-descarboxy compounds IIA, IIB and IIC have been formed, the sequences described in Schemes A-I can be followed to produce compounds of formula (I).

One skilled in the art will appreciate that esterification of the C4 and C5 carboxy groups of IIA, IIB or IIC may lead to a mixture of mono and diesters and these may be readily separated, by preparative HPLC using a C-8 reverse phase column and a gradient solvent of H$_2$O/acetonitrile. Similarly, preparation of C4 and 5 amides and thioesters of IIA, IIB and IIC may lead to mixtures of mono C4, mono C5 and disubstituted compounds which can be separated in the same manner.

SCHEME A:

For substitution at position 6 [R$^4$—(A)$_a$—O—] and for the preparation of compounds (4) and (5), compounds IIA, IIB or IIC can be converted to diester (1) by stirring with a R$^2$O—N,N'-dialkylisourea in a solution such as toluene, benzene, acetonitrile, tetrahydrofuran (THF) and/or dimethoxyethane (DME). [Mathias, L. J., Synthesis, 561–576 (1979)]. R$^2$ may be t-butyl, benzyl, 4-methoxybenzyl, trimethylsilyl ethyl or any other ester group that is normally selected as an ester protecting group. The rate of bis-esterification utilizing this methodology can be accelerated with gentle heating. An alternative method for the preparation of diiester analogs of II(A-C) is to react II(A-C) and a diazoorgano reagent (R$^2$N$_2$) such as diazomethane or diazoethane in an organic solvent normally used for this reaction such as methanol, THF or diethylether. A third method involves stirring a solution of II(A-C) with excess R$^2$-halide (chloride, bromide or iodide) in a standard organic solvent in the presence of a base such as triethylamine (Et$_3$N), pyridine or DBU. It may be reasonable at this point to modify or to protect the C-7 hydroxyl group as compound (2). This position may be modified or protected with any number of the commonly utilized protecting groups (i.e., R$^5$) including the t-butyldimethylsilyl, triethylsilyl, trimethylsilyl, 2-(trialkylsilyl)ethyl, methoxymethyl, and 1-methyl-1-methoxyethyl (MME) ethers. These may be easily appended by methods commonly reported in the literature. Removal of the existing natural product R$^4$—(A)$_a$— acyl group to provide compound (3) can be selectively achieved in the presence of other acyl substituents or esters contained in (2) by use of an alkali metal hydroxide such as lithium hydroxide in the presence of 30% hydrogen peroxide. Employment of titanium (IV)alkoxide reagents in the alcohol corresponding to the diester will also selectively de-acylate at position 6, provided that the R$^1$ moiety does not contain an ester grouping; however, when the R$^1$ moiety contains an acetoxy group as in (2), this method provides compound (3'). A third mode of selective deacylation can be achieved with hydroxylamine hydrochloride. Alternatively, the deacylated IIB and IIC analogues may be prepared according to the procedures in Schemes H and I, respectively.

Derivatization of compound (3) or (3') at the 6 position with R$^4$—(A)$_a$— as an ester, carbamate, carbonate or ether can be accomplished in high yield utilizing a number of procedures. For esterification, employment of an acid chloride or anhydride (symmetrical or mixed) in a dried aprotic solvent such as dichloromethane, THF, DME, diethyl ether with a base such as Et$_3$N, dimethylaminopyridine (DMAP) or pyridine are two normally used methods. Another method utilizes the requisite carboxylic acid in an aprotic solvent with any of the standard carbodiimide coupling reagents, such as dicyclohexyl carbodiimide (DCC), 2-ethoxy-1-ethoxycarbonyl-1,2-dihydroquinolone (EEDQ), benzotriazol-1-yloxytris(dimethylamino)phosphoniumhexafluorophosphate (BOP reagent). Carbamate derivatives can be prepared by reacting (3) with an isocyanate, that is commercially available or that can be prepared, in an aprotic solvent such as toluene, pyridine, benzene, acetonitrile, tetrahydrofuran (THF) and/or dimethoxyethane (DME). An alternate method involves first reacting alcohol (3) with carbonyldiimidazole in an anhydrous aprotic solvent such as toluene, benzene, acetonitrile, tetrahydrofuran (THF) and/or dimethoxyethane (DME) followed by the addition of the appropriate amine. Normally, the intermediate 1-imidazocarbonyl analog (4) can be isolated and purified by standard chromatographic methods. Carbonate analogs can be prepared by the second procedure described for the preparation of carbamates, with an alcohol being used in place of the amine. Ether analogs can be prepared by standard alkylation reactions with the appropriate organohalide (Cl, Br, I) in an anhydrous solvent such as toluene, benzene, acetonitrile, tetrahydrofuran (THF), dimethoxyethane (DME), or dimethylformamide (DMF) and a base such as sodium or potassium hydride. If an organoiodide is not employed, the reaction rate can be accelerated with a catalytic amount of tetra-n-butylammonium iodide. Any of these derivatives (4) can be purified by standard chromatographic methods using silica gel as the solid phase.

Deprotection of the bis ester of (4) or (4') to provide analogs (5) and (5') of II can be achieved in high yield by commonly used methods. t-Butyl esters are removed in an aprotic solvent with trifluoro-acetic acid (TFA), trialkylethylsilyl esters can be removed with standard fluoride reagents such as tri-n-butyl-ammonium fluoride, and benzyl or substituted benzyl esters can be selectively removed by standard methodology including hydrogenation or more selectively via transfer hydrogenation.

SCHEME B:

Where the starting material is compound (IIA) that is (1S,4S,5R,6R,7R)-1-[(4S)-acetoxy-3-methylene-(5R)-methyl-6-phenyl]hexyl-4,6,7-trihydroxy-6-O-((4S),(6S)-dimethyl-2-octenoyl)-2,8-dioxabicyclo-[3.2.1]octane-4,5-dicarboxylic acid, the 4'-[S]-acetoxy group at $R^1$ can be modified in a variety of ways. In the case where compound (2) is the bis-t-butylester-7-(1-methyl-1-methoxyethyl) ether, the C1 acetyl group can be selectively removed by a reagent composed of cerium (III) chloride and a Grignard reagent such as methyl or ethyl magnesium chloride in THF to yield (4'). The alcohol product (4') can be derivatized as an ester, carbamate, carbonate or ether (6) utilizing procedures similar to those used for the preparation of analogs (4). Deprotection of compounds (6) is carried out in a manner similar to that for preparation of compounds (5) to produce derivatives (7).

Any of the carboxyl groups C4 and/or C5 of compounds II(A-C), (5) and (7) may be derivatized by procedures described in the following Schemes B and C. The C4 and C5 carboxyl groups of (7) can be differentially esterified by use of $R^2O$—N,N'—dialkyl-isoureas to produce differentially bis-esterified analog (8). The resultant compound (8) can then be selectively deprotected at C4 and C5 by methods that have been previously described to give compound (7).

SCHEME C:

The diacid compound (7) can also be esterified at C5 by stirring compound (7) in an anhydrous aprotic solvent such as benzene, toluene, THF, or DME with an isourea reagent such as O-t-butyl-N,N'-diisopropylisourea to give compound (9). This may also be accomplished by stirring compound (7) with trifluoroacetic acid anhydride (TFAA) followed by addition of an alcohol. C5 mercaptoesters or amides can be prepared if a mercaptan or amine is used in place of an alcohol.

In the case where (10) is the 5-benzyl ester, one can selectively derivatize the C4-carboxyl group as an ester, amide or mercaptoester (11). Compound (10) can be derivatized as $COZ^1$ by any number of methods. Conversion of (10) to an intermediate mixed anhydride is accomplished by stirring (10) in an anhydrous aprotic solvent such as diethylether, THF, DME or dichloromethane with an alkyl chloroformate such as isobutyl, isopropyl, methyl or ethyl chloroformate and a base such as N-methylmorpholine pyridine, DBU, DMAP or $Et_3N$. To this mixed anhydride is then added an amine for making amides, an alcohol for making esters or a mercaptan for making thioesters. The resultant compound (11) can then be selectively deprotected at C5 to give compound (14). C4 esters of the diacid compound (7) can be similarly prepared. Moreover, when (12) is a 4-benzyl ester, the C5 position may be similarly derivatized to produce (13). Both (11) or (13) may be selectively deprotected by hydrogenolysis to provide monoacids (14) or (15).

Differentially esterified (9) can be derivatized at C4 by procedures previously described to produce (16). Deprotection at C5 produces compound (17).

Diesters of II(A-C) could be prepared by several procedures. Stirring II(A-C) with $R^2O$—N,N'-dialkylurea in a solvent such as methylene chloride, toluene, benzene, acetonitrile, dioxane, tetrahydrofuran, and/or dimethoxyethane gives II-diesters in good yield. Also, stirring II(A-C) with a diazoorgano reagent ($R^2N_2$) such as diazomethane in organic solvents such as tetrahydrofuran, diethyl ether or methanol gives the diesters in excellent yield. An alternative procedure to prepare diesters of II(A-C) is to stir II(A-C) with 1,8-diazabicyclo[5.4.0]undec-7-ene (DBU) and alkyl halide in solvents such as acetonitrile, THF and dimethoxyethane.

SCHEME D:

Compounds (4) or (6) can be further derivatized by hydrogenation/hydrogenolysis. For example, when (4) or (6) is stirred in ethyl acetate with a catalytic amount of Pd/C or rhodium-aluminate in an atmosphere of hydrogen gas, a mixture of compounds (18) and (19) can be produced. Further hydrogenation can produce compound (20). When (4) or (6) is a derivative of IIA, the [S]-hydroxyl group at position 4 of C1 can be inverted to compound (21) by the Mitsunobu reaction [O. Mitsunobu, Bull. Chem. Soc. Japan, 44, 3427 (1971)]. Compound (21) can be further derivatized to Compound (22) by procedures analogous to those employed to produce compounds (6) as described in Scheme B.

SCHEME E:

The C1 side chain of compound (4') can be selectively degraded to intermediates (24), (26) and (27) which can be synthetic starting points for broad synthetic modification. One procedure involves the selective osmylation of (4') to produce penta-ol compound (23). Selective oxidative cleavage of (23) with periodate provides a mixture of hydroxyketones (25a) and (25b). Compound (25a) can also be produced by reacting the appropriate compound (4') with ozone. Reduction followed by oxidative cleavage of hydroxy-ketones (25) gives aldehyde (26) which can be reduced to alcohol (27) by several standard procedures which may include sodium borohydride, in an appropriate solvent. Exhaustive periodate cleavage of (23) produces carboxylic acid analog (24). Acid (24) can be reduced to (27).

SCHEME F:

Transformations of intermediates (24), (26) and (27) for derivatization of the Cl-side chain are of standard procedures. Ester derivatives of (24) can be prepared by stirring with a $R^2O$—N,N'-dialkylisourea in a solution such as toluene, benzene, acetonitrile, tetrahydrofuran (THF) and/or dimethoxyethane (DME). [Mathias, L. J., Synthesis, 561–576 (1979)]. Ester derivatives may also be prepared by stirring a solution of (24) with excess $R^2$-halide (chloride, bromide or iodide) in a standard organic solvent in the presence of a base such as triethylamine ($Et_3N$), pyridine or DBU. For ester or amide derivatives, employment of an acid chloride or anhydride (symmetrical or mixed) of (24) in a dried aprotic solvent such as dichloromethane, THF, DME, diethyl ether with a base such as $Et_3N$, dimethylaminopyridine (DMAP) or pyridine are two normally used methods. Another method utilizes the reaction of (24) and the requisite alcohol or amine in an aprotic solvent with any of the standard carbodiimide coupling reagents, such as dicyclohexylcarbodiimide (DCC), 2-ethoxy-1-ethoxycarbonyl-1,2-dihydroquinolone (EEDQ), benzotriazol-1-yloxytris-(dimethylamino)phosphoniumhexafluorophosphate (BOP reagent). Ketone derivatives (28) can be prepared by reacting (24) with an alkyl chloroformate such as methyl chloroformate to form the intermediate mixed anhydride. Subsequent reaction of the mixed anhydride with an alkyl lithium reagent or Grignard reagent provides ketone derivatives (28). Ketone derivatives (28) can be reduced to an alcohol group by stirring the ketone in a solvent such as methanol or ethanol with sodium borohydride. Any of the above derivatives can be deprotected to the diacid or selectively esterified or amidated analogs using procedures previously described.

Aldehyde analog (26) can be converted to olefinic derivatives (29) utilizing well known reactions such as the Wittig or Peterson olefinations. By these methods, both cis and trans olefins can be prepared. These olefinic derivatives can be converted to saturated derivatives (29) by hydrogenation. Alcohol derivatives of (26) can be prepared by the addition of an organometallic reagent such an alkyl lithium or a Grignard reagent. The alcohol derivative can be further derivatized by conversion to an ether, ester or carbamate by procedures described in Scheme B. Alternatively, alcohol (30) can be oxidized to ketone derivative (31) utilizing any one of a variety of commonly used oxidation reagents.

Hydroxy-derivative (27) can be derivatized as a sulfide, ether, unsubstituted or substituted amine, amide, ester, alkyl, or carbamate derivative. (27) can be derivatized as its p-toluenesulfonate, methanesulfonate, chloride, bromide or iodide by commonly used procedures. With any of these reagents can be reacted a metalalkoxide, metalmercaptide, amine to form ethers, sulfides or amines. Amines can be converted to amides by coupling with carboxylic acids via standard peptide coupling reagents. Alkyl derivatives can be prepared by reacting tosylate, methanesulfonate or halide derivatives with the appropriate organometallic reagent. Carbamate and Ester derivatives of (27) can be prepared by procedures described in Scheme A.

SCHEME G:

The 6-position side chains which contain a heteroatom, Y, such as O, S, SO, $SO_2$, NH or $NR^3$ can be readily prepared. One general synthetic strategy to prepare side chains for the preparation of esters, carbamates, carbonates or ethers containing a heteroatom involves a Williamson-type alkyation of a haloorganoester (35) such as t-butyl-3-bromo-propionate with an alcohol (Patai, "The Chemistry of the Ether Linkage", pp 446–450, 460–468, Interscience, New York, 1967), a mercaptan (Peach, in Patai, "The Chemistry of the Thiol Group", Wiley, N.Y., 1974) or an amine such as n-decylamine (34) in the presence of the appropriate base to give ester (36). Compound (36) may also be prepared in the reverse manner with organohalide (34') and aminoester, hydroxyester or mercaptoester (35'). Esters of type (36) can also be prepared by conjugate addition of (34) to 2,3-unsaturated esters (38) in the presence of an appropriate base. In the case where Y is NH or NR, it is more convenient to prepare compounds (36) by reductive alkylation with amine (34) or (35') with an aldehyde (35) or (34') where in these special cases, X=CHO. (Klyuev and Khidekel, Russ. Chem. Rev., 49, 14–27, 1980, Rylander, "Catalytic Hydrogenation over Platinum Metals", Academic Press, N.Y., 1967, Borch et. al., J. Am. Chem. Soc., 93, 2897, 1971) Ester (36) can be hydrolyzed to carboxylic acid (37), a substrate for acylation at C6 of II (A–C). Alternatively, (36) or (37) can be reduced to the corresponding alcohol (39), which can act as substrates for carbonate preparation. Alcohol (39) may be prepared by reaction of (40) with (41) or (40') with (41') by methods similar to those for (34) and (35) or (34') and (35'). In this case a protected alcohol (41) or (41') reacts to form a protected form of (39) which can then be deprotected. Alcohol (39) can be converted to a leaving group such as a methansulfonate, paratoluenesulfonate, bromide or iodide by standard procedures. Thus, compound (42) would act as a substrate for the preparation of ether derivatives. Alternatively, (42) can be converted to amino analogs (43) which would act as substrates for the preparation of carbamate analogs.

SCHEME H:

Further exemplifying the derivatization of these natural products, in the case of IIB, protection of the two acid functionalities as t-butyl esters (1B) is accomplished using the O-t-butyl-N,N'-diisopropylisourea method described in Scheme A. Selective protection of the C7 alcohol proceeds with 2-methoxypropene giving (2B), also described in Scheme A. The C4' alcohol is protected using 5,6-dihydro-4-methoxy-2H-pyran giving the C4' enol ether product of vinyl ether exchange, (2B'). The ester at C6 is removed using sodium hydroxide to give the C6-hydroxy-7-MME-bis-t-butyl ester (3B'). The 6-hydroxy group can be functionalized using the previously described procedures (Scheme A) to provide 4B' which was deprotected with trifluoroacetic acid in an aprotic solvent to give the C6 analogs of IIB (5B).

SCHEME I:

As an additional means of derivatizing the natural products, in the case of IIC, the 7-MME-bis-t-butyl ester (2C) is synthesized according to the procedures described in Scheme A. The olefin of the C6 ester provides a derivatization site allowing for selective C6 deacylation while maintaining the C4' acetate. Oxidation, for example with osmium tetroxide, provides a mixture of diastereomeric C6-derived diols (2C'). These diol intermediates are unstable to basic conditions such as potassium t-butoxide or DBU in DMF. The resulting C6-hydroxy-7-MME-bis-t-butyl ester (3C) is then functionalized as described in Scheme A to give the protected derivative (4C). All protecting groups are removed using the trifluoroacetic acid method to give the target IIC-C6 analogs (5C).

SCHEME 1

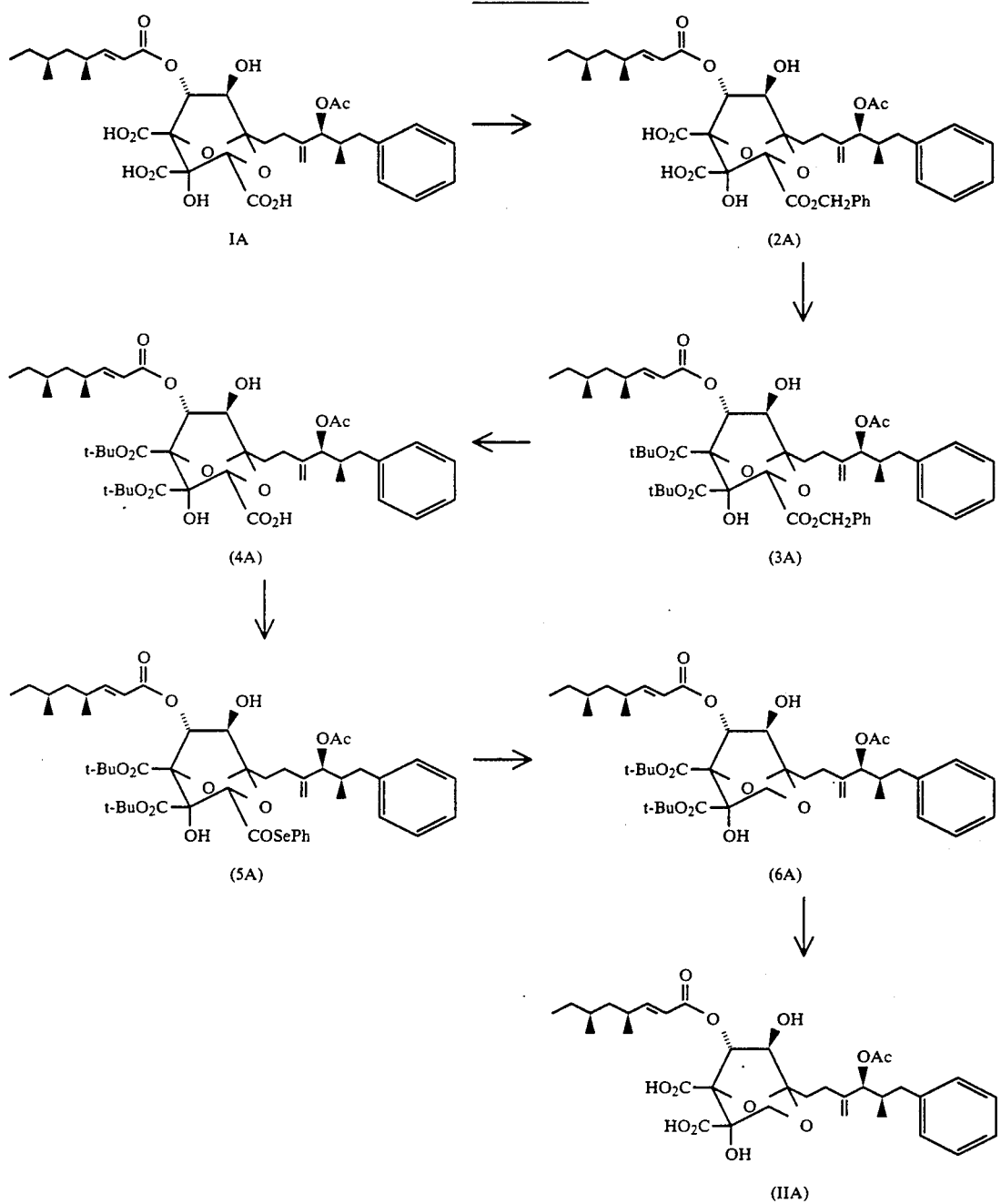

SCHEME A
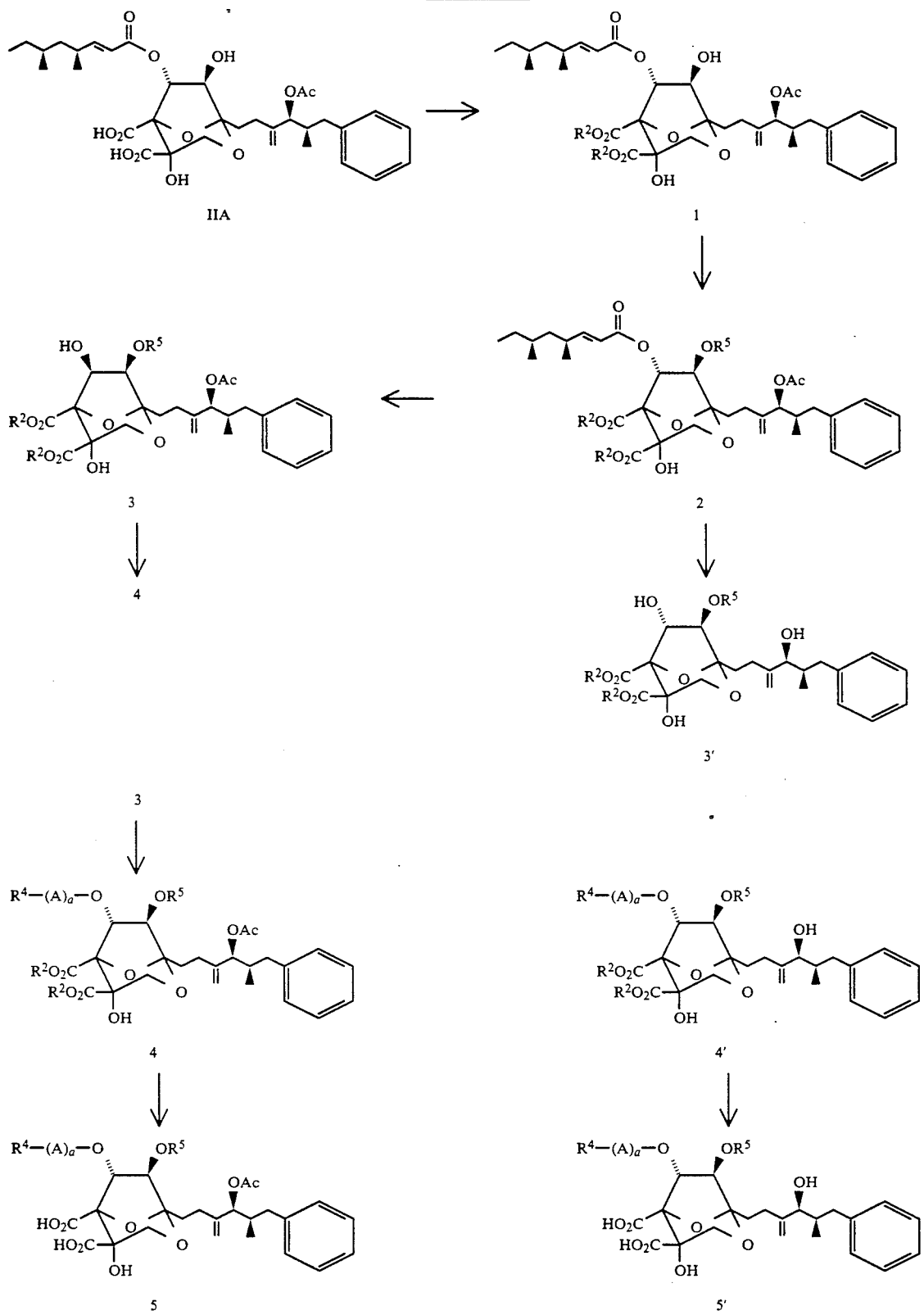

SCHEME B
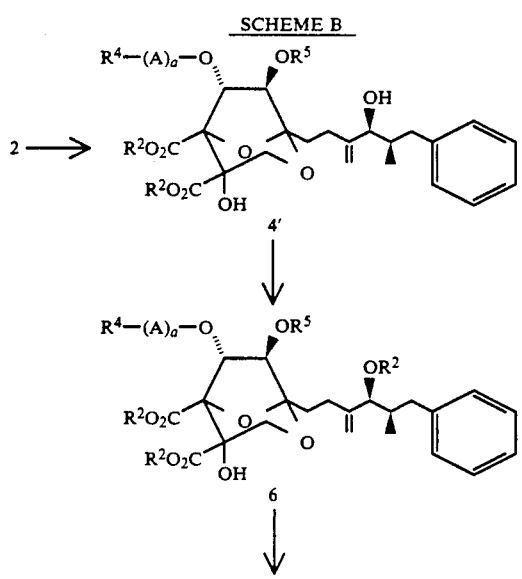
-continued
SCHEME B
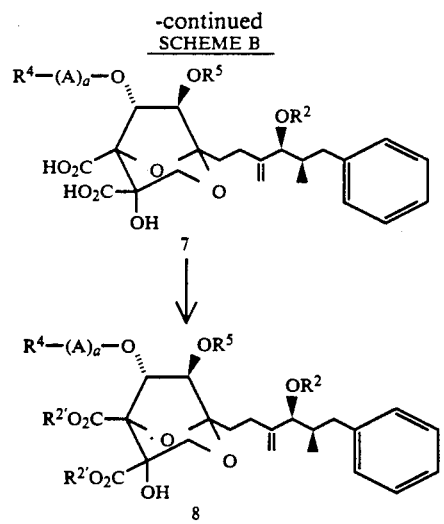
SCHEME C

SCHEME C
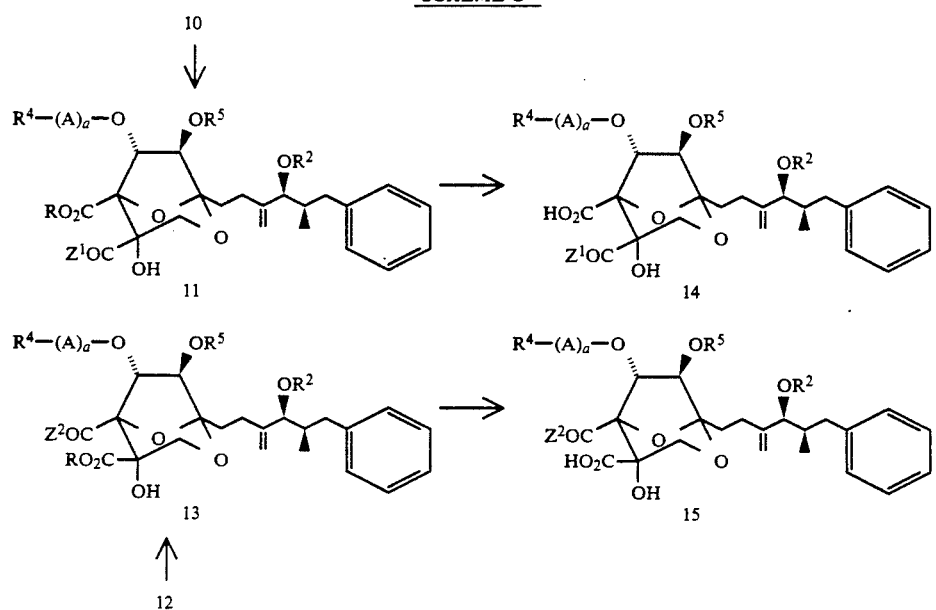
SCHEME D
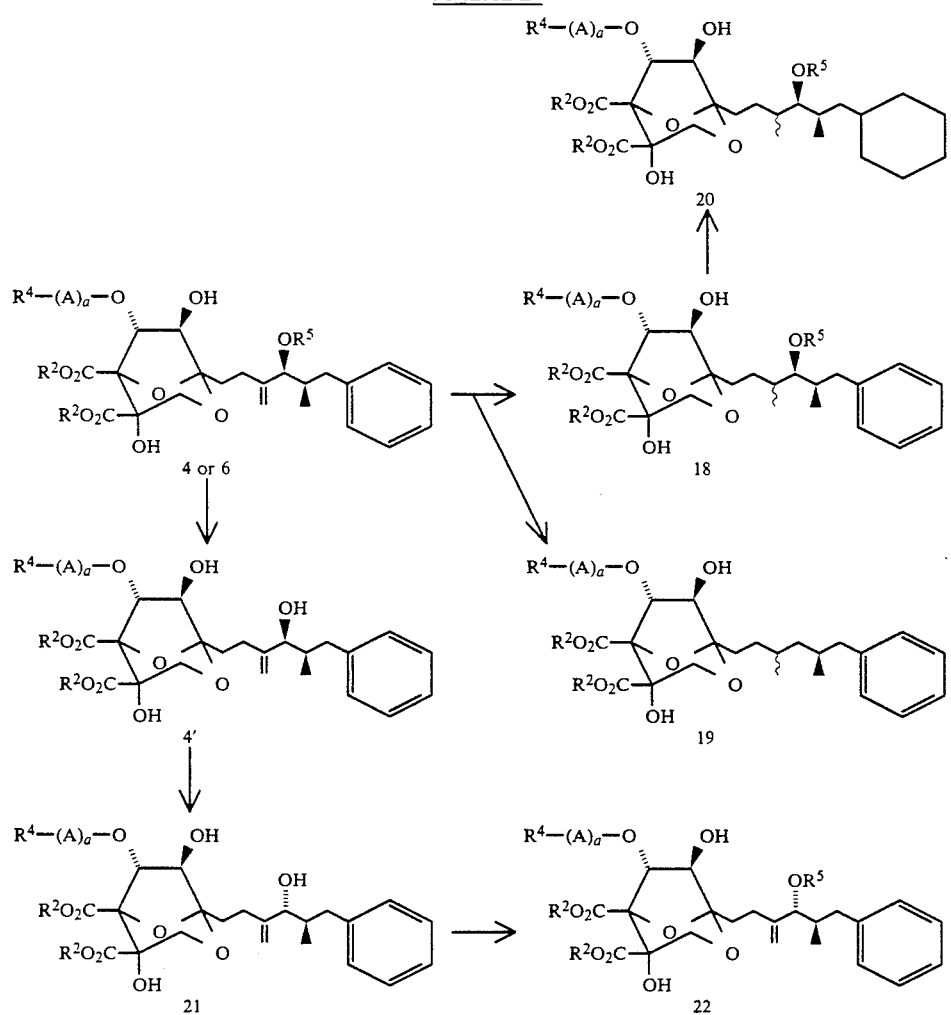

SCHEME E
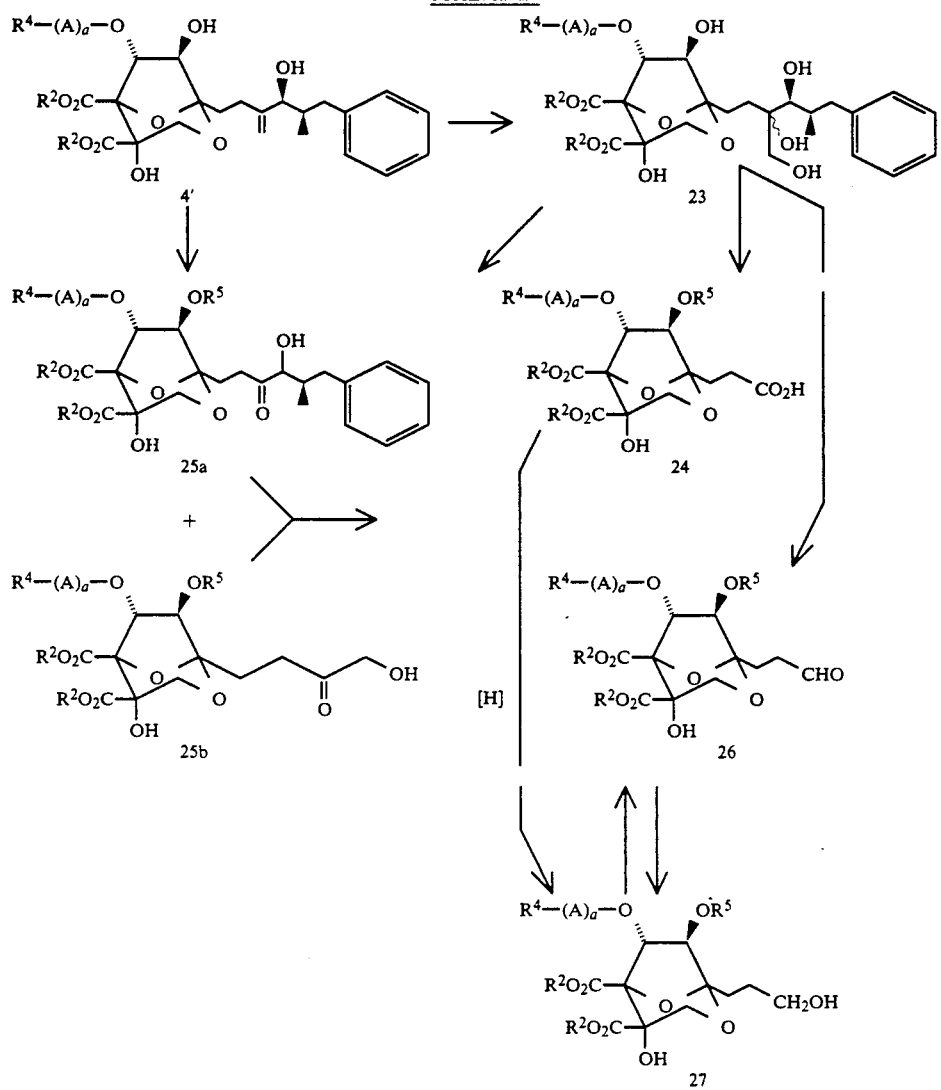

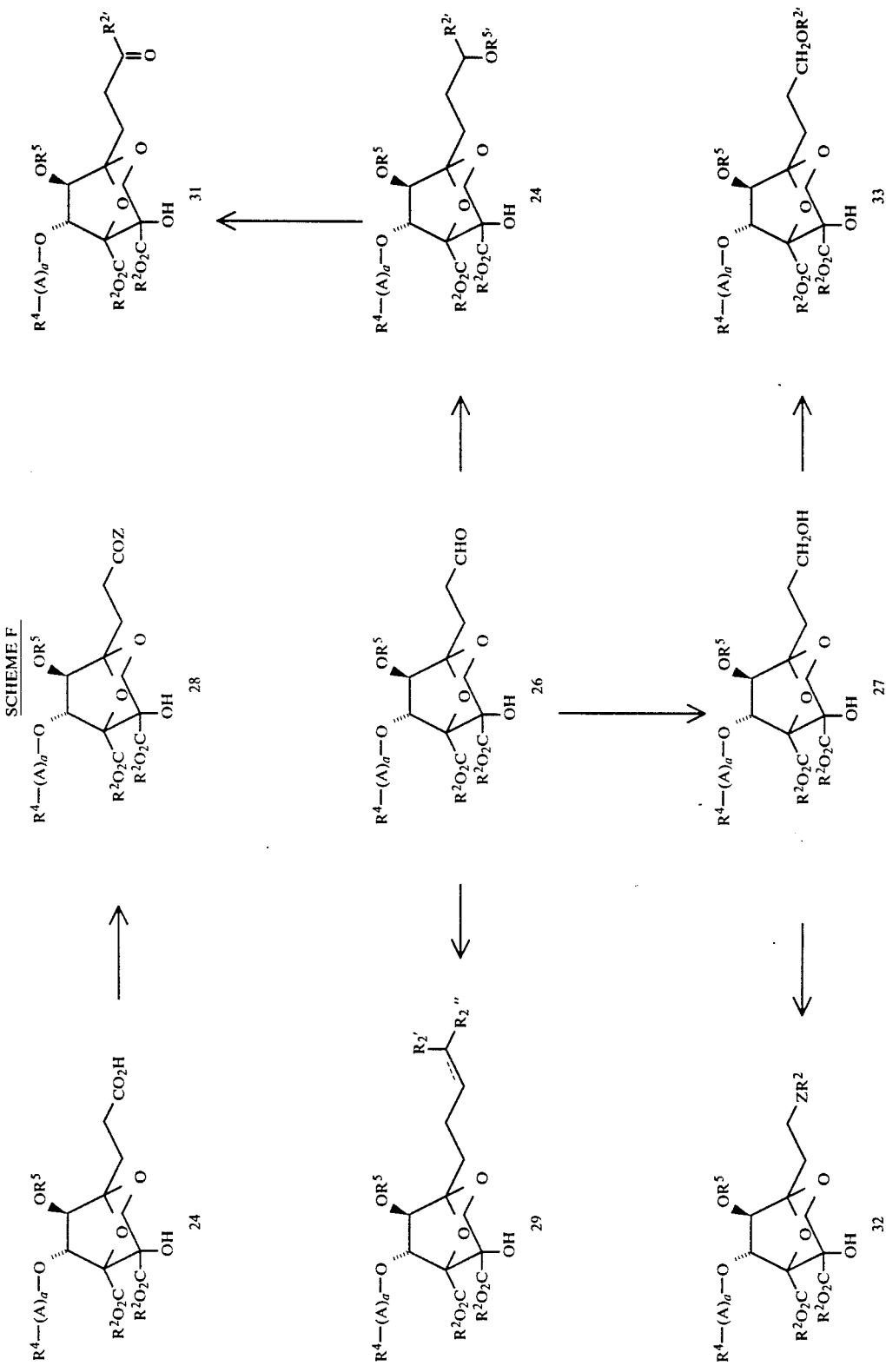

SCHEME G
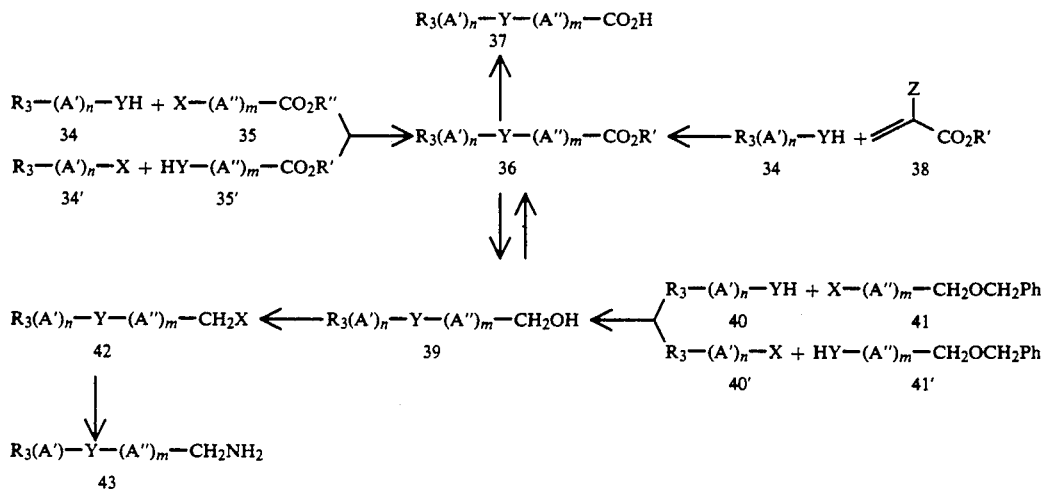
SCHEME H
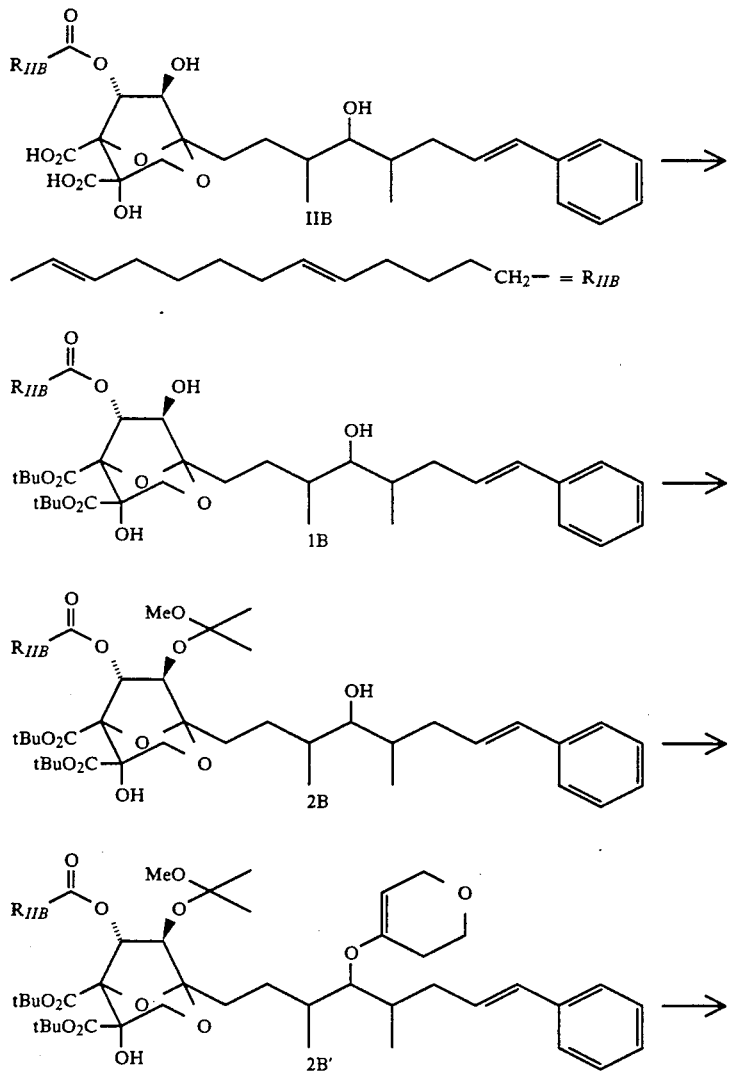

SCHEME H
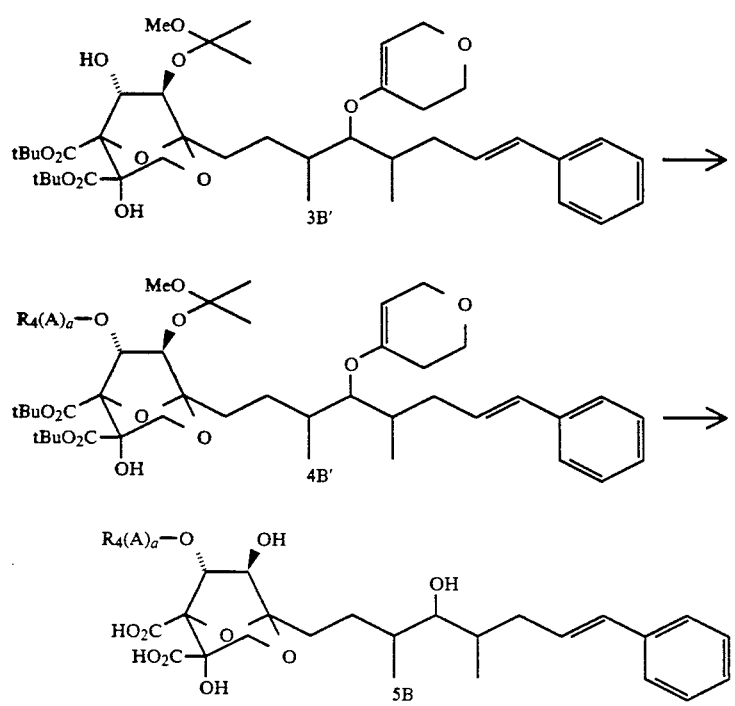
SCHEME I
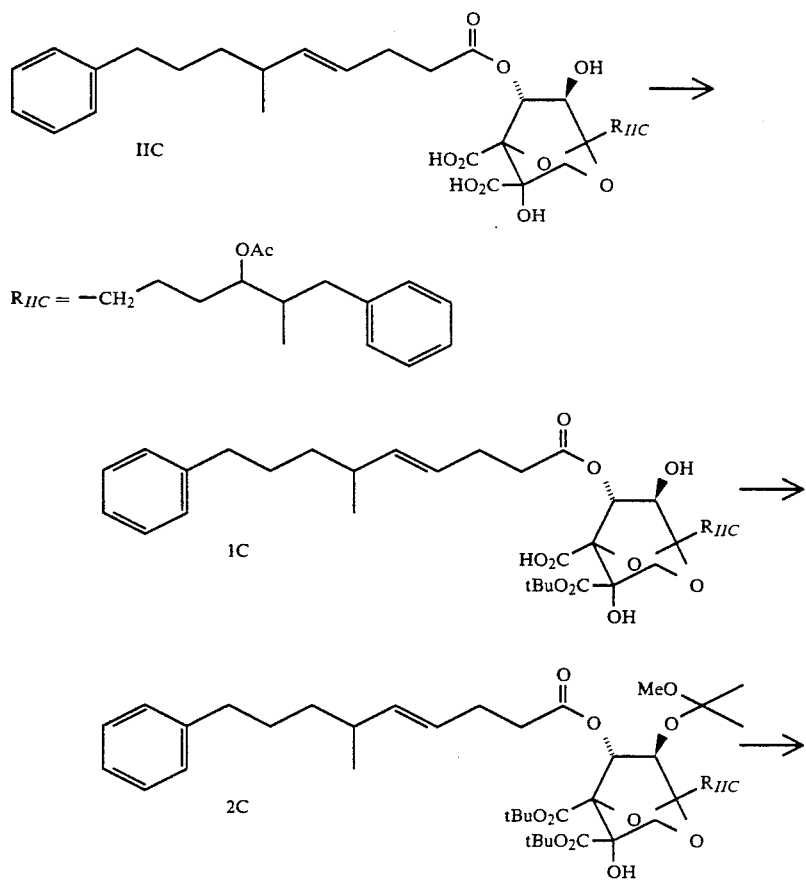

SCHEME I -continued

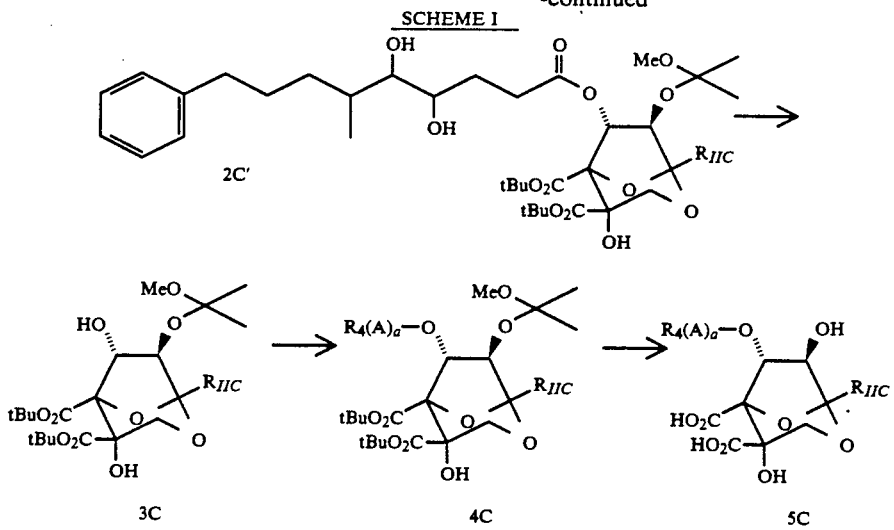

The present invention is also directed to a method of treating hypercholesterolemia which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The present invention is also directed to a method of inhibiting squalene synthase which comprises the administration to a subject in need of such treatment a nontoxic therapeutically effective amount of compound represented by structural formula (I) and pharmaceutically acceptable salts thereof. Specifically, the compounds of this invention are useful in treating disease conditions such as, but not limited to, hypercholesterolemia which result from the action of the enzyme squalene synthase. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N-N'-dibenzylethylendiamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one or two of the carboxyl groups are in the salt form.

The compounds of this invention may also be administered in combination with other cholesterol lowering agents such as those which inhibit an enzymatic pathway in the biosynthesis of cholesterol. Example of such agents would include but are not limited to HMG-CoA reductase inhibitors, HMG-COA synthase inhibitors, and squalene expoxidase inhibitors. Illustrative of such inhibitors are lovastatin, simvastation, pravastatin and fluvastatin. Other cholesterol lowering agents that may be administered include niacin, probucol, and the fibric acids, clofibrate and gemfibrozil. Appropriate daily dosages for adults are niacin (2-8 gm), probucol (up to 1000 mg), clofibrate (up to 2 gm) and gemfibrozil (800-1500 mg).

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic squalene synthase inhibitory activity of representative compounds of this invention was measured by the standard in vitro protocol described below:

Preparation of Microsomes:

Male, Charles River CD rats (120 to 150 g) were fed a diet containing 0.1% lovastatin for 4 days. The livers from these rats were homogenized in 5 volumes (ml/g) of ice cold 50 mM HEPES (4-(2-hydroxy-ethyl)-1-piperazine-ethanesulfonic acid), 5 mM EDTA(ethylenediaminetetraacetic acid) pH 7.5 with a Potter-Elvehjem type tissue grinder. The homogenate was centrifuged twice at 20,000×g for 15 minutes at 4° C., discarding the pellet each time. The supernatant was then centrifuged at 100,000×g for 1 hour at 4° C. The resulting microsomal pellet was resuspended in a volume of the above homogenizing buffer equal to one-fifth the volume of the original homogenate. This microsomal preparation has a protein concentration of about 7 mg/ml. The microsomal suspensions were stored in aliquots at −70° C. Squalene synthase activity in these aliquots is stable for at least several months.

Partial Purification of Prenyl Transferase

Prenyl transferase was purified to use in the enzymatic synthesis of radiolabelled farnesyl pyrophosphate. Prenyl transferase was assayed by the method of Rilling (Methods in Enzymology 110, 125-129 (1985)) and a unit of activity is defined as the amount of enzyme that will produce 1 μmole of farnesyl pyrophosphate per minute at 30° C. in the standard assay.

The livers of 23 forty-day old male rats that had been fed 5% cholestyramine plus 0.1% lovastatin were homogenized in a Waring blender in 1 liter of 10 mM mercaptoethanol, 2 mM EDTA, 25 μM leupeptin, 0.005% phenylmethyl sulfonyl fluoride pH 7.0 containing 0.1 trypsin inhibitor units of aprotinin/ml. The homogenate was centrifuged at 20,000×g for 20 minutes. The supernatant was adjusted to pH 5.5. with 6N HOAc and centrifuged at 100,000×g for 1 hour. This supernatant was adjusted to pH 7.0 with 3N KOH and a 35-60% ammonium sulfate fraction taken. The 60% pellet was redissolved in 60 ml of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm column of DEAE-sepharose 4B equilibrated with Buffer A. The column was washed with 700 ml of Buffer A and a 1 liter gradient from Buffer A to 100 mM potassium phosphate, 10 mM mercaptoethanol, 1 mM EDTA pH 7.0. Fractions having a specific activity greater than 0.20 units/mg were combined, solid ammonium sulfate was added to bring to 60% saturation and pelleted. The pellet was dissolved in 8 ml of 10 mM Tris, 10 mM β-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/ml with a specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for at least 6 months.

Enzymatic Synthesis of [4-$^{14}$C]farnesyl-pyrophosphate

The solvent (ethanol: 0.15N NH$_4$OH, 1:1) was removed from 55 μCi of [4-$^{14}$C]isopentenyl pyrophosphate(47.9 μCi/μmole) by rotary evaporation. Six hundred microliters of 100 mM Tris, 10 mM MgCl$_2$, 4 mM dithiothreitol pH 7.5 was added and the solution was transferred to a 1.5 ml Eppendorf centrifuge tube. Geranyl-pyrophosphate, 250 μl of a 20 mM solution, and 50 μl of the ammonium sulfate suspension of prenyl transferase were added to initiate the reaction. This incubation contained 5 μmoles of geranyl pyrophosphate, 1.15 μmoles of isopentenyl pyrophosphate, 6 μmoles of MgCl$_2$ of 0.18 units of prenyl transferase in a volume of 900 μl. The incubation was conducted at 37° C. During the incubation, the mix turned cloudy white as the newly formed magnesium complex of farnesyl pyrophosphate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 ml of 50 mM HEPES, 5 mM EDTA, pH 7.5. The yield was 50.7 μCi (92%) of [4-$^{14}$C]farnesyl pyrophosphate. The [4-$^{14}$C]farnesyl pyrophosphate was stored in aliquots at −70° C.

Squalene Synthase Assay

Reactions were performed in 16×125 mm screw cap test tubes. A batch assay mix was prepared from the following solution:

| | μl per assay | volume for 50 assays |
|---|---|---|
| 1. 250 mM Hepes pH 7.5 | 20 | 1000 |
| 2. NaF 110 mM | 10 | 500 |
| 3. MgCl$_2$ 55 mM | 10 | 500 |
| 4. Dithiothreitol 30 mM | 10 | 500 |
| 5. NADPH 10 mM (made fresh) | 10 | 500 |
| 6. [4-$^{14}$C]farnesyl-pyrophosphate 47.9 μCi/μmole, and 0.025 μCi/3.0 μl | 3.0 | 150 |
| 7. H$_2$O | 24 | 1200 |

This assay mix was degassed under a vacuum and flushed with N$_2$. Solutions of the squalene synthase inhibitors were prepared either in DMSO or MeOH and a 1:120 dilution of the microsomal protein was made with the original homogenizing buffer. For each reaction, 87 μl of the assay mix was taken with 3 μl of an inhibitor solution (DMSO or MeOH in the controls), warmed to 30° C. in a water bath and then the reaction was initiated by the addition of 10 μl of the 1:120 dilution of microsomal protein (0.6 μg protein total in the assay). The reactions were stopped after 20 minutes by the addition of 100 μl of a 1:1 mix of 40% KOH with 95% EtOH. The stopped mix was heated at 65° C. for 30 minutes, cooled, 10 ml of heptane was added and the mix was vortexed. Two g of activated alumina was then added, the mix vortexed again, the alumina allowed to settle and 5 ml of the heptane layer was removed. Ten ml of scintillation fluid was added to the heptane solution and radioactivity was determined by liquid scintillation counting.

Percent inhibition is calculated by the formula:

$$1 - \frac{[\text{Sample} - \text{Blank}]}{[\text{Control} - \text{Blank}]} \times 100$$

IC$_{50}$ values were determined by plotting the log of the concentration of the test compound versus the percentage inhibition. The IC$_{50}$ is the concentration of inhibitor that gives 50% inhibition as determined from these plots.

Representative compounds of this invention exhibited IC$_{50}$ values which were all <500 μM.

The compounds of the present invention are also useful in inhibiting farnesyl-protein transferase.

The Ras gene is found activated in many human cancers including colorectal carcinoma, exocrine pancreatic carcinoma, and myloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171-286 (1989). Forms of Ras in cancer cells have mutations that distinguish the protein from Ras in normal cells.

At least 3 post-translational modification are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583-586 (1984)). Other proteins having this motif include the Ras-related GTP-binding proteins such as Rho, fungal mating factors, the nuclear lamins; and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093-1098 (1989); Hancock et al., *Cell* 57: 1167-1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1989); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell*, 62: 81-88 (1990); Schaber et al., *J. Biol. Chem.*, 265:14701-14704 (1990); Schafer et al., *Science,* 249: 1133-1139 (1990); Manne et al., *Proc. Natl. Acad. Sci USA,* 87: 7541-7545 (1990).

Inhibition of farnesyl-protein transferase and, thereby, of farnesylation of the Ras protein, blocks the ability of Ras to transform normal cells to cancer cells. The compounds of the present invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no-Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630-6634 (1989)). Cytosollocalized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects such as interference with other metabolic processes which utilize the enzyme.

These compounds are inhibitors of farnesyl-protein transerase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides with the CAAX sequence inhibit Ras farnesylation (Schaber et al., ibid; Reiss et al., ibid; Reiss et al., *PNAS,* 88:732-736 (1991)). However, the reported inhibitors of farnesyl-transferase are metabolically unstable or inactive in cells.

Pharmaceutical compositions containing the compounds of this invention and methods of treatment utilizing these compositions for use in inhibiting farnesyl-protein transferase and farnesylation of the oncogene protein Ras are included within this invention.

The intrinsic farnesyl-protein transferase (FTase) activity of representative compounds of this invention is measured by the assays described below:

RASIT ASSAY I

Farnesyl-protein transferase (Ftase) from bovine brain is chromatographed on DEAE-Sephacel (Pharmacia, 0-0.8M NaCl gradient elution), N-octyl agarose (Sigma, 0.0.6M NaCl gradient elution), and a mono Q HPLC column (Pharmacia, 0.0.3M NaCl gradient). Ras-CVLS at 3.5 $\mu$M, 0.25 $\mu$M [$^3$H]FPP, and the indicated compounds are incubated with this partially purified enzyme preparation.

RASIT ASSAY II

Farnesyl-protein transferase (Ftase) from bovine brain is chromatographed on DEAE-Sephacel (Pharmacia, Q-0.8M NaCl gradient elution), N-octyl agarose (Sigma, 0-0.6M NaCl gradient elution), and a mono Q HPLC column (Pharmacia, 0-0.3M NaCl gradient). Ras-CVLS at 1.0 $\mu$M, 0.5 $\mu$M [$^3$H]FPP, and the indicated compounds are incubated with this partially purified enzyme preparation.

The pharmaceutical compositions containing the compounds of structural formula I inhibit farnesyl-protein transferase and the farnesylation of the encogene protein Ras. These compounds are useful as pharmaceutical agents for mammals, especially for humans. These compounds may be administered to patients for the use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a method of the treatment of cancer, comprising the administration of a pharmaceutical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight to about 20 mg/kg of body weight of a mammal per day, preferably of between 0.5 mg/kg of body weight to about 10 mg/kg of body weight of a mammal per day.

The present compounds also demonstrate broad spectrum antifungal activity as determined by broth and agar dilution methods. The compounds are particularly active towards filamentous fungi and yeasts including Candida albicans and Cryptococcus neoformans. The sensitivity of filamentous fungi and yeast is determined using inhibitor dilution assays in microtiter format. The compounds are dissolved in DMSO at 2 mg/ml and serially diluted in 0.1M phosphate buffer, pH 7.0 in the microtiter dish from 100 to 0.006 µg/ml. A standardized spore suspension for testing the filamentous fungi is prepared by inoculating Antibiotic Medium #3 containing 1.5% agar with spores such that $1.5 \times 10^3$ colony forming units are added per well. The microtiter wells are filled with 50 µ of buffer containing compound and 50 µl of inoculated medium.

The sensitivity of yeasts is determined by inoculating yeast nitrogen base containing 1% dextrose (YNB/G) with aliquots of an overnight yeast culture grown in Yeast Morphology (YM) media at 35° C. and diluting in YNB/G to yield a final concentration of $1.5-7.5 \times 10^3$ colony forming units/well. To test the sensitivity of yeast, compound is solubilized in 10 percent aqueous DMSO at 2.56 mg/ml. The compound is diluted serially in YNB/G from 128 to 0.06 µg/ml and further diluted 1:10 in YNB/G. The wells are filled with 150 µl of media containing drug. The minimum inhibitory concentration (MIC) is defined as the lowest concentration to prevent growth after an incubation for 42 hours, at 28° C. for the filamentous fungi and 24 to 48 hours, at 35° for the yeasts.

| Zaragozic Acid A-3-Descarboxy Minimum Inhibitory Concentration (mcg/ml) | |
|---|---|
| Candida | |
| MY 1028 | 32 |
| MY 1055 | 64 |
| MY 1750 | 64 |
| MY 1019 | >128 |
| MY 1010 | 64 |
| MY 2099 | >128 |
| MY 1012 | 16 |
| Cryptococcus | — |
| MY 1051 | .25 |
| MY 1146 | 2 |
| MY 2061 | 4 |
| MY 2062 | 1 |
| Sachromyces | — |
| MY 1976 | >128 |
| Aspergillus | |
| MF 0383 | 2 |
| MF 4839 | 8 |
| MF 5669 | 8 |
| MF 5668 | 32 |

| Zaragozic Acid A-3-Descarboxy-4'-methylpivalate ester Minimum Inhibitory Concentration (mcg/ml) | |
|---|---|
| Candida | |
| MY 1028 | >128 |
| MY 1055 | >128 |
| MY 1750 | >128 |
| MY 1019 | >128 |
| MY 1010 | >128 |
| MY 2099 | >128 |
| MY 1012 | 16 |
| Cryptococcus | — |
| MY 1051 | 2 |
| MY 1146 | 8 |
| MY 2061 | 64 |
| MY 2062 | 8 |
| Sachromyces | — |
| MY 1976 | >128 |
| Aspergillus | — |
| MF 0383 | 1 |
| MF 4839 | 32 |
| MF 5669 | 32 |
| MF 5668 | 32 |

Thus the present invention is also directed to a method of treating fungus infections which comprises the administration to an organism in need of such treatment a nontoxic therapeutically effective amount of a compound represented by the structural formula (I) and pharmaceutically acceptable salts thereof. Generally from 2 to about 20 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monosterate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof to inhibit fungal growth.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of Formula I.

The following Examples illustrate the preparation of the compounds of formula (I) and their incorporation into pharmaceutical compositions and as such are not to be considered as limiting the invention set forth in the claims appended hereto.

Zaragozic acid A, IA, is (1S, 3S, 4S, 6R, 7R)-1-[(4S)-acetoxy-3-methylene-5-methyl-6-phenyl]hexyl-4,6,7-trihydroxy-6-0-(4,6-dimethyl-2-octenoyl)-2,8-dioxabicyclo-[3.2.1]octane-3,4,5-tricarboxylic acid.

EXAMPLE 1

Preparation of Zaragozic acid A-3-benzyl ester (2A).

A solution of acetyl chloride (0.4 ml) in benzyl alcohol (10 ml) was stirred at room temperature for 30 min. To this mixture was added Zaragozic acid A (i.e., IA) (1 g) and the reaction mixture was stirred for an additional 6 hr. The mixture was poured into acetonitrile-water (200 mL, 38%) and purified by chromatography (C-8, acetonitrile-water, 3:2) to give the title compound. $^1$H NMR (300 MHz, CD$_3$OD) δ7.46–7.12 (m, 10H), 6.88 (dd, J=8.9, 18 Hz, 1H), 6.38 (brs, 1H), 5.84 (d, J=15 Hz, 1H), 5.42 (s, 1H), 5.23 (dd, J=13, 51 Hz), 2 Hz), 2H), 5.14 (s, 1H), 5.04–5.00 (2s, 2H), 4.06 (br s, 1H), 2.71 (m, 1H), 2.54–2.00 (m, 7H), 2.12 (s, 3H), 1.50–1.1 (m, 6H), 1.07 (d, J=6 Hz, 3H), 0.90 (m, 9H); FAB m/e 793 (M+2Li), 799 (M+3Li).

EXAMPLE 2

Preparation of Zaragozic acid A-3-benzyl-4,5-di-t-butyl ester (3A)

To a solution of (2A) (100 mg) in methylene chloride (2 mL) was added O-t-butyl-N,N'-diisopropylisourea (300 mg) and the solution was stirred at 40° C. for 2 days. The reaction mixture was then cooled to room temperature, concentrated in vacuo and filtered through silica eluting with ethyl acetate:hexane, 1:4 to yield the title compound. 1H NMR (400 MHz, CDCl3) δ7.35–7.08 (m, 10H), 6.89 (dd, J=16, 8.4 Hz, 1H), 5.97 (d, J=1 Hz, 1H), 5.75 (d, J=16 Hz), 1H), 5.24 (s, 1H), 5.16 (dd, J=12 Hz, 64 Hz, 2H), 5.06 (br s, 1H), 4.94 (br s, 2H), 4.00 (br s, 1H), 2.96 (d, J=2 Hz, 1H), 2.66 (m, 1H), 2.5–2.2 (m, 5H), 2.15–2.00 (m, 4H), 2.05 (s, 3H), 1.39 (s, 9H), 1.37 (s, 9H), 1.40–1.05 (m, 6H), 1.02 (d, J=6 Hz, 3H), 0.86–0.76 (m, 9H).

EXAMPLE 3

Preparation of Zaragozic acid A-4,5-di-t-butyl ester (4A)

To a solution of Zaragozic acid A-3-benzyl-4,5-di-t-butyl ester (3A) (100 mg) in methanol (4 mL) was added 1-methyl-1,4-cyclohexadiene (200 uL) and Pd/C (50 mg). The reaction mixture was stirred at 30°–35° C. for 1.5 hr and filtered over celite. The filtrate was evaporated in vacuo to give the title compound. 1NMR (400 MHz, CD3OD) δ7.30–7.10 (m, 5H), 6.89 (dd, J=8.16 Hz, 1H), 6.43 (d, J=1 Hz, 1H), 5.82 (d, J=16 Hz, 1H), 5.06 (d, J=5 Hz, 1H0, 5.04 (s, 1H), 5.01 and 4.96 (each s, each 1H), 4.07 (s, 1H), 2.69 (m, 1H), 2.5–2.20 (m, 6H), 2.10 (s, 3H), 1.60 (s, 9H), 1.42 (s, 9H), 1.65–1.05 (m, 6H), 1.03 (d, J=8.1 Hz, 3H), 0.88 (m, 10H).

EXAMPLE 4

Preparation of Zaragozic acid A-3-phenylseleno ester-4,5-di-t-butyl ester (5A)

To a room temperature solution of Zaragozic acid A-4,5-di-t-butyl ester (4A) (10.42 g, 12.04 mmol) in THF (160 mL) was added triethylamine (3.35 mL, 24.09 mmol) followed by dichlorophenyl phosphate (2.34 mL, 15.65 mmol). The reaction was allowed to stir until TLC indicated complete disappearance of the starting material. Upon complete consumption of the starting material triethylamine (3.35 mL, 24.1 mmol) was added followed by phenyl selenol (1.92 mL, 18.06 mmoL). The reaction was allowed to stir at room temperature overnight whereupon it was diluted with EtOAc washed with water, salt, saturated sodium bicarbonate, brine, dried (MgSO$_4$) and concentrated. Chromatography of the residue (silica gel, 9:1 to 4:1 to 2:1 hexanes-:EtOAc) gave the selenoester: $^1$H NMR (400 MHz, CDCl$_3$) δ7.50–7.06 (m, 10H), 6.89 (dd, J=15.6, 8.4 Hz, 1H), 5.88 (d,J=1.8 Hz, 1H), 5.75 (d, J=15.6 Hz, 1H), 5.14 (d, J=5.1 Hz, 1H), 5.12 (s, 1H), 5.01 (s, 1H), 4.99 (s, 1H), 4.07 (br s, 2H), 2.71 (dd, J=13.1, 4.9 Hz, 1H), 2.61–2.22 (m, 6H), 2.09 (s, 3H), 1.52 (s, 9H), 1.45 (s, 9H), 1.44–1.07 (m, 7H), 1.02 (d, J=6.6 Hz, 3H), 0.84–0.78 (m, 7H).

EXAMPLE 5

Preparation of Zaragozic acid A-3-decarboxy-4,5-di-t-butyl ester (6A)

To an 80° C. solution of n-Bu$_3$Sn-H (0.17 mL, 0.64 mmol) and AIBN (15 mg) in benzene (1.0 mL) was added the seleno ester (5A) (0.20 g, 0.21 mmol) dropwise. The reaction was allowed to stir until TLC indicated complete disappearance of the starting material. Upon complete consumption of the starting material the reaction was concentrated in vacuo and the residue was chromatographed (silica gel, 3:1 hexanes:EtOAc) to give the decarbonylated material as a white foam: $^1$H NMR (400 MHz, CDCl$_3$) δ7.25–7.09 (m, 5H), 6.88 (dd, J=15.7, 8.5 Hz, 1H), 5.88 (d,J=15.7 Hz, 1H) 5.07 (d, J=5.3 Hz, 1H), 4.94 (s, 1H), 4.92 (2, 1H), 4.52 (d, J=12.1 Hz, 1H), 4.01 (m, 1H), 3.92 (s, 1H), 3.75 (d, J=12.3 Hz, 1H), 3.07 (m, 1H), 2.66 (dd, J=13.2, 5.5 Hz, 1H), 2.34–2.28 m, 4H), 2.06 (s, 3H), 1.52 (s, 9H), 1.45 (s, 9H), 1.12–1.06 (m, 2H), 1.01 (d, J=6.7 Hz, 3H).

EXAMPLE 6

Preparation of Zaragozic acid A-3-descarboxy (IIA)

To an ambient solution of Zaragozic acid A-3-decarboxy-4,5-di-t-butyl ester (6A) (1.6 g) in CH$_2$Cl$_2$ (30 mL) was added TFA (10 mL). The reaction was allowed to stir overnight whereupon it was concentrated in vacuo. The residue was azeotropically dried with toluene (3×5 mL) and lyophilized from benzene to yield a white powder: $^1$H NMR (400 MHz, CD$_3$OD) δ7.26–7.12 (m, 5H), 6.84 (dd, J=15.6, 8.5 Hz, 1H), 6.26 (d, J=1.6 Hz, 1H), 5.78 (d, J=15.7 Hz, 1H), 5.05 (d, J=4.6 Hz, 1H), 4.97 (s, 1H), 4.94 (s, 1H), 4.63 (d, J=12.5 Hz, 1H), 3.99 (d, J=1.9 Hz, 1H), 3.75 (d, J=12.4 Hz, 1H), 2.66 (dd, J=13.2, 6.2 Hz, 1H), 2.45–2.18 (m, 5H), 2.09 (s, 3H), 1.93 (m, 2H), 1.41–1.28 (m, 6H), 1.15–1.08 (m, 2H), 1.02 (d, J=6.7 Hz, 3H), 0.96–0.81 (m, 9H): MS (FAB) m/e 645 M-1).

EXAMPLE 7

Preparation of Zaragozic acid A-3-descarboxy-4-methyl pivalate ester (2d)

To a solution of Zaragozic acid A-3-decarboxy (IIA) (197.6 mg, 0.31 mmole) in refluxing acetonitrile (3.0 mL), was added DBU (0.33 mmol, 49.0 μl) followed by chloromethyl pivalate (0.61 mmole, 82.0 μl) and a few crystals of sodium iodide. The reaction was allowed to stir overnight whereupon it was concentrated in vacuo and the residue purified by preparative HPLC, using a C-8 reverse phase column and a gradient solvent mixture 60% H$_2$O/40% acetonitrile to 100% acetonitrile over 40 minutes with a flow rate of 10 ml/min, to yield the C-4 POM ester as a colorless oil: $^1$H NMR (400 MHz, CD$_3$OD): δ7.28–7.10 (m, 5H), 6.85 (dd, J=15.75, 8.67 Hz, 1H), 6.15 (s, 1H), 5.88–5.75 (m, 3H), 5.02 (d, J=4.98 Hz, 1H), 4.97 (s, 1H), 4.93 (s, 1H), 4.57 (d, J=12.22 Hz, 1H), 4.00 (s, 1H), 3.75 (d, J=12.45 Hz, 1H), 2.65 (dd, J=13.44, 6.32 Hz, 1H), 2.46–2.40 (m, 2H), 2.10 (s, 3H), 1.95–1.85 (m, 2H), 1.69–1.60 (m, 1H), 1.40–1.37 (m, 5H), 1.19 (s, 9H), 1.03 (d, J=6.64 Hz, 2H), 0.90–0.81 (m, 8H). MS (FAB) M+ Na 784.

EXAMPLE 8

Preparation of 6A-7-(1-methyl-1-methoxyethyl ether)

To a 0° C. solution of the di-t-butyl ester (4.2 g, 5.6 mmol) in CH$_2$Cl$_2$ (100 mL) was added p-PTS (several crystals) and 2-methoxypropene (2.68 mL, 28.1 mmol). The reaction was allowed to stir until complete consumption of the starting material was observed by TLC. The reaction was then diluted with CH$_2$Cl$_2$ and washed with saturated sodium bicarbonate, brine, dried (Na$_2$SO$_4$) concentrated and the residue chromatographed (silica gel, 4:1 hexanes:EtOAc) to give 3.2 g of the C-7 protected compound: $^1$H NMR (CD$_3$OD, 400 MHz) includes 7.28–7.16 (m, 5H), 6.88 (dd, J=15.6, 7.1 Hz, 1H), 6.48 (d, J=1.9 Hz, 1H), 5.85 (d, J=15.7 Hz, 1H), 5.07 (d, J=4.6 Hz, 1H), 4.97 (br s, s), 4.95 (br s, 1H) 4.64 (d, J=12.4 Hz, 1H), 3.67 (d, J=12.4 Hz, 1H), 3.18 (s, 3H), 2.09 (s,3H), 1.60 (s, 9H), 1.39 (s, 9H).

EXAMPLE 9

Preparation of 6A-6-hydroxy-7-(1-methyl-1-methoxyethyl ether)

To a solution of 6A-7-(1-methyl-1-methoxyethyl ether) (3.00 g, 3.65 mmol) was added sodium acetate (10.95 g, 80.84 mmol) followed by hydroxylamine hydrochloride (2.53 g, 36.5 mmol). The reaction was stirred overnight then concentrated to ⅓ its volume, diluted with ethyl acetate, washed with saturated sodium bicarbonate, brine, dried (Na$_2$SO$_4$) concentrated and the residue chromatographed (silica gel, 1:1 hexanes:EtOAc) to yield 2.38 g of the deacylated material: $^1$H NMR (CDCl$_3$, 400 MHz) includes 7.26–7.10 (m, 5H), 5.08 (d, J=5.1 Hz, 1H), 4.96 (br s, 1H), 4.92 (br s, 1H), 4.41 (d, J=12.0 Hz, 1H), 4.06 (d, J=2.0 Hz, 1H), 3.78 (br s, 1H), 3.68 (d, J=12.0 Hz, 1H), 3.26 (s, 3H), 2.07 (s, 3H), 1.52 (s, 9H), 1.48 (s, 9H).

EXAMPLE 10

Preparation of 1a-7-(1-methyl-1-methoxyethyl ether)-4,5-bis-t-butyl ester

To a room temperature solution of 6A-6-hydroxy-7-(1-methyl-1-methoxyethyl ether) (200 mg, 0.29 mmol) in CH$_2$Cl$_2$ (5.0 mL) was added several crystals of DMAP followed by DCC (100 mg, 0.46 mmol) and the acid (121.3 mg, 0.58 mmol). The reaction was maintained at room temperature overnight then concentrated in vacuo. Chromatography of the residue (silica gel, 4:1 hexanes:EtOAc) gave 132 mg of the ester. $^1$H NMR (CDCl$_3$, 400 Mz) includes δ7.26–7.12 (m, 5H), 6.30 (d, J=1.9 Hz, 1H), 5.32–5.29 (m, 2H), 5.10 (d, J=5.1 Hz, 1H), 4.96 (br s, 1H), 4.92 (br s, 1H), 4.54 (d, J=12.3 Hz, 1H), 4.18 (d, J=1.9 Hz, 1H), 3.93 (br s, 1H), 3.71 (d, J=12.2 Hz, 1H), 3.19 (s, 3H), 2.07 (s, 3H), 1.58 (s, 9H), 1.42 (s, 9H).

EXAMPLE 11

Preparation of 1a

Deprotection of 1a-7-(1-methyl-1-methoxyethyl ether)-4,5-bis-t-butyl ester (130 mg) in CH$_2$Cl$_2$ (3.0 mL) and TFA (1.0 mL) gave 50.2 mg of 1a after preparative HPLC purification; $^1$H NMR (CD$_3$OD, 400 MHz) includes 7.26–7.09 (m, 5H), 6.20 (d, J=1.7 Hz, 1H), 5.47–5.27 (m, 2H), 5.05 (d, J=4.9 Hz, 1H), 4.96 (br s, 1H), 4.95 (br s, 1H), 4.63 (d, J=12.4 Hz, 1H), 3.98 (d, J=1.71 Hz, 1H), 3.75 (d, J=12.4 Hz, 1H), 2.08 (s, 3H), 0.92 (d, J=6.7 Hz, 3H), 0.84 (d, J=6.7 Hz, 3H); MS (FAB negitive ion), m/e 721 (M−1)

EXAMPLE 12

Preparation of 2a

This compound was synthesized in the manner previously described. $^1$H NMR (CD$_3$OD, 400 MHz, reported as a 1:1 mixture of diastereomers) includes 7.27–7.12 (m, 5H), 6.88–6.81 (dd, J=15.6, 7.1 Hz, 1H), 6.77–6.75 (m, 5H), 6.29 and 6.18 (d, J=2.0 Hz, 1H), 5.80 and 5.77 (two d, J=15.7 and 15.2 Hz respectively, 1H), 5.05 (d, J=2.9 Hz, 1H), 4.97 (brs s, 1H), 4.94 (br s, s), 4.23–4.15 (m, 2H), 2.09 (s, 3H), 1.55 and 1.51 (two doublets, J=6.4 and 5.4 respectively, 3H) 1.02 (d, J=6.6 Hz, 3H).

EXAMPLE 13

Preparation of 2b

To a 40° C. solution of IIA (100 mg, 0.15 mmol) was added DBU (25.5 uL, 0.17 mmol) followed by pivaloyloxyethyl chloride (POE-Cl) (50.7 mg, 0.31 mmol). The reaction was allowed to stir overnight whereupon it was concentrated in vacuo. Preparative HPLC purification of the residue gave 26 mg of the C-3 POE ester; $^1$H NMR (CD$_3$OD, 400 MHz, reported as a 1:1 mixture of diastereomers) includes 7.27–7.14 (m, 5H), 6.89–6.81 (m, 2H), 6.32 and 6.16 (d, J=1.8 and 1.94 Hz, 1H), 5.81 and 5.76 (two d, J=15.8 Hz, 1H), 5.05 (d, J=4.2 Hz, 1H), 4.97 (brs s, 1H), 4.94 (br s, s), 2.08 (s, 3H), 1.54 and 1.50 (two doublets, J=5.4, 3H) 1.21 and 1.16 (s, 9H).

EXAMPLE 14

Preparation of 2c

This compound was synthesized in the manner previously described. $^1$H NMR (CD$_3$OD, 400 MHz) includes 7.27–7.12 (m, 5H), 6.84 (dd, J=15.6, 7.1 Hz, 1H), 6.24 (d, J=2.3 Hz, 1H), 5.76 (d, J=15.7 Hz, 1H), 5.13 (d, J=13.9 Hz, 1H), 5.04 (d, J=4.5 Hz, 1H), 4.97 (br s, 1H), 4.94 (br s, 1H), 4.58 (d, J=12.4 Hz, 1H), 4.01 (d, J=2.1 Hz, 1H), 3.79 (d, J=12.3 Hz, 1H), 2.14 (s, 3H), 2.09 (s, 3H); MS (FAB negitive ion) m/e 757 M-1).

EXAMPLE 15

Preparation of 6A-7-(1-methyl-1-methoxyethyl ether)-Cl(4′)-alcohol

A mixture of anhydrous cerium trichloride (783.1 mg, 3.17 mmol) in THF (11.3 mL) was stirred overnight at room temperature. The following morning the mixture was cooled to −78° C. and ethylmagnesium chloride (1.63 mL, 3.25 mmol) was added. The mixture was allowed to stir at −78° C. for 30 mins. whereupon it was warmed to 0° C. for 1.5 hours then recooled to −78° C. A solution of 6A-7-(1-methyl-1-methoxyethyl ether) (300 mg, 0.36 mmol) in THF (2×5 mL) was then added. The reaction was stirred for ca. 10 mins. then quenched with saturated ammonium chloride. The mixture was allowed to warm to room temperature and diluted with ethyl acetate. The organic layer was washed with water, brine, dried (MgSO$_4$) and concentrated. Chromatography of the residue (silica gel, 3:1 hexanes:ethyl acetate) gave 266 mg of the allylic alcohol: $^1$H NMR (CDCl$_3$, 400 MHz) includes 7.26–7.12 (m, 5H), 6.87 (dd, J=15.6, 6.2 Hz, 1H), 6.35 (d, J=1.9 Hz, 1H), 5.74 (d, J=15.7 Hz, 1H), 5.09 (br s, 1H), 4.95 (br s, 1H), 4.57 (d, J=12.4 Hz, 1H), 4.26 (d, J=1.9 Hz, 1H), 4.05 (d, J=4.9 Hz, 1H), 3.87 (s, 1H), 3.69 (d, J=12.2 Hz, 1H), 3.19 (s, 3H), 1.58 (s, 9H), 1.35 (s, 12H).

EXAMPLE 16

Preparation of 4b-7-(1-methyl-1-methoxyethyl ether)-Cl(4′)-Butyrate-4,5-bis-benzyl ester To a solution of 6A-7-(1-methyl-1-methoxyethyl ether)-Cl(4′)-alcohol (260 mg, 0.32 mmol) in CH$_2$Cl$_2$ (5.0 mL) was added several crystals of DMAP followed by triethyl amine (669.0 uL, 4.8 mmol) and butyric anhydride (523.5 μL, 3.2 mmol). The reaction was allowed to stir overnight whereupon it was diluted with CH$_2$Cl$_2$ washed with water, saturated sodium bicarbonate, brine, dried (Na$_2$SO$_4$) and concentrated. Chromatography of the reside (silica gel, 4:1 hexanes:EtOAc) gave 250 mg of the C4′ butyl ester: $^1$H NMR (CDCl$_3$, 400 MHz) includes 7.26–7.13 (m, 5H), 6.88 (dd, J=15.7, 7.5 Hz, 1H), 6.37 (d, J=1.9 Hz, 1H), 5.80 (d, J=15.7 Hz, 1H), 5.12 (d, J=5.1 Hz, 1H), 4.95 (br s, 1H), 4.92 (br s, 1H), 4.57 (d, J=12.3 Hz, 1H), 4.23 (d, J=1.9 Hz, 1H), 3.92 (br s, 1H), 3.71 (d, J=12.3 Hz, 1H), 3.19 (s, 3H), 1.59 (s, 9H), 1.36 (s, 9H).

EXAMPLE 17

Preparation of 4b

Compound 4b-7-(1-methyl-1-methoxyethyl ether)-Cl(4′)-Butyrate was deprotected in the usual fashion: $^1$H NMR (CD$_3$OD, 400 MHz) includes 7.27–7.12 (m, 5H), 6.84 (dd, J=15.7, 7.51 Hz, 1H), 6.25 (d, J=1.9 Hz, 1H), 5.81 (d, J=15.7 Hz, 1H), 5.07 (d, J=4.5 Hz, 1H), 4.97 (br s, 1H), 4.93 (br s, 1H), 4.63 (d, J=12.4 Hz, 1H), 3.99 (d, J=1.9 Hz, 1H), 3.92, 3.74 (d, J=12.4 Hz, 1H), 0.97 (t, J=7.41 Hz, 2H).

EXAMPLE 18

Preparation of 4c

The C-3 Pivaloyloxymethyl ester (i.e., POM ester) of example 17 (i.e., 4b) was prepared in the usual fashion: $^1$H NMR (CD$_3$OD, 400 MHz) includes 7.26–7.12 (m, 5H), 6.84 (dd, J=15.6, 6.6 Hz, 1H), 6.13 (d, J=2.0 Hz, 1H), 5.87–5.76 (m, 3H), 5.06 (d, J=4.5 Hz, 1H), 4.96 (br s, 1H), 4.93 (br s, 1H), 4.58 (d, J=12.3 Hz, 1H), 3.99 (d, J=2.1 Hz, 1H), 3.75 (d, J=12.3 Hz, 1H), 1.18 (s, 9H), 0.97 (t, J=7.4 Hz, 2H).

EXAMPLE 19

Preparation of 4d-7-(1-methyl-1-methoxyethyl ether)-Cl(4′)-Benzoate-4,5-bis-benzyl ester To a solution of the 6A-7-(1-methyl-1-methoxyethyl ether)-Cl(4′)-alcohol (150 mg, 0.19 mmol) in CH$_2$Cl$_2$ (2.0 mL) was added several crystals of DMAP followed by triethylamine (389.6 μL, 2.79 mmol) and benzoic anhydride (420.8 μL, 1.86 mmol). The reaction was allowed to stir overnight whereupon it was diluted with CH$_2$Cl$_2$ washed with water, saturated sodium bicarbonate, brine, dried (Na$_2$SO$_4$) and concentrated. Chromatography of the reside (silica gel, 4:1 hexanes:EtOAc) gave 113 mg of the C4′ benzoate ester: $^1$H NMR (CDCl$_3$, 400 MHz) includes 8.08 (d, J=7.1 Hz, 2H), 7.55 (t, J=7.5 Hz, 1H), 7.44 (t, J=7.5 Hz, 2H), 7.27–7.15 (m, 5H), 6.88 (dd, J=15.7, 7.6 Hz, 1H), 6.37 (d, J=1.7 Hz, 1H), 5.78 (d, J=15.7 Hz, 1H), 5.35 (d, J=4.6 Hz, 1H), 5.04 (br s, 1H), 4.96 (br s, 1H), 4.75 (d, J=12.1 Hz, 1H), 4.22 (d, J=1.8 Hz, 1H), 3.93 (br s, 1H), 3.71 (d, J=12.2 Hz, 1H), 3.14 (s, 3H), 1.59 (s, 9H), 1.37 (s, 9H).

EXAMPLE 20

Preparation of 4d 4d-7-(1-methyl-1-methoxyethyl ether)-Cl(4')-benzoate-4,5-bis-benzyl ester was deprotected in the usual fashion: $^1$H NMR (CD$_3$OD, 400 MHz) includes 8.06 (d, J=7.1 Hz, 2H), 7.63 (t, J=7.3 Hz, 1H), 7.51 (t, J=7.9 Hz, 2H), 7.27–7.12 (m, 5H), 6.84 (dd, J=15.7, 7.1 Hz, 1H), 6.27 (d, J=1.4 Hz, 1H), 5.79 (d, J=15.7 Hz, 1H), 5.29 (d, J=4.1 Hz, 1H), 4.99 (br s, 1H), 4.64 (d, J=12.1 Hz, 1H), 4.01 (d, J=1.4 Hz, 1H), 3.76 (d, J=12.4 Hz, 1H), 1.02 (d, J=6.6 Hz, 3H), 0.99 (d, J=6.8 Hz, 3H).

EXAMPLE 21

Preparation of 4e

The C-3 POM ester of 4d was prepared in the usual fashion; $^1$H NMR (CD$_3$OD, 400 MHz) includes 8.06 (d, J=7.0 Hz, 2H), 7.61 (t, J=6.3 Hz, 1H), 7.52 (t, J=7.9 Hz, 2H), 7.26–7.12 (m, 5H), 6.84 (dd, J=15.7, 7.1 Hz, 1H), 6.27 (d, J=1.4 Hz, 1H), 5.29 (d, J=4.5 Hz, 1H), 4.59 (d, J=12.2 Hz, 1H), 4.01 (d, J=2.0 Hz, 1H), 3.76 (d, J=12.4 Hz, 1H), 1.18 (s, 9H).

EXAMPLE 22

Preparation of 1-4,5-bis-benzyl ester

A solution of 3% HCl/trimethylsilylethanol (50.8 mL) was added the triacid IA (5.0 g, 7.24 mmol). The reaction was allowed to stir until complete by HPLC. The mixture was then diluted with ether and washed with water, brine, dried (MgSO$_4$) and concentrated. The residue was then vacuum distilled to remove excess trimethylsilylethanol. The residue from this distillation was then dissolved in benzene (200 mL) and benzylisourea (34 g, 74.9 mmol) was then added. The reaction was allowed to stir at 60°–70° C. until TLC indicated the reaction was complete. The reaction was then concentrated, filtered with hexanes, concentrated and chromatographed twice (silica gel, 4:1 hexanes:EtOAc) to give the C-3 trimethylsilyl, C-4,5 dibenzyl ester. To a solution of the preceding triester (2.6 g, 2.5 mmol) in 2:1 THF:DMF (30 mL) was added tetrabutylammonium floride (3.75 mL, 3.75 mmol). The reaction was allowed to stir until complete by TLC whereupon it was diluted with ethyl acetate, washed with saturated ammonium chloride, water, brine, dried (MgSO$_4$), concentrated and the residue chromatographed (silica gel, 6:1 CHCl$_3$:CH$_3$OH) to give 1.8 g of the C-3 acid. To a solution of the C-3 acid in THF (20 mL) was added triethylamine (1.33 mL, 9.55 mmol) and phenyl dichlorophosphate (0.71 mL, 4.77 mmol). The reaction was stirred at room temperature for 30 minutes whereupon triethylamine (0.79 mL, 7.73 mmol) was added followed by benzeneselenol (0.61 mL, 5.73 mmol). The reaction was stirred overnight whereupon it was diluted with ethyl acetate, washed with saturated sodium bicarbonate, water, brine, dried (Na$_2$SO$_4$) concentrated and the residue was chromatographed (silica gel, 8:1 to 4:1 to 2:1 hexanes:EtOAc) to give 1.02 g of the C-3 selenoester. To an 8° C. solution of tri-n-butyltin hydride (0.76 mL, 2.82 mmol) in benzene (14.0 mL) was added several crystals of AIBN followed by the dropwise addition of the C-3 seleno ester (1.02 g, 0.94 mmol) in benzene (4.7 mL). The reaction was stirred until TLC indicated the complete disappearance of the starting selenoester whereupon the reaction was concentrated and the residue chromatographed (silica gel, 8:1 to 4:1 to 2:1 hexanes:EtOAc) to yield 330 mg of the decarbonylated material: $^1$H NMR (CDCl$_3$, 400 MHz) includes 7.29–7.11 (m, 15H), 6.77 (dd, J=15.7, 7.0 Hz, 1H), 5.73 (d, J=2.2 Hz, 1H), 5.36 (d, J=15.7 Hz, 1H), 4.95 (br s, 1H), 4.91 (br s, 1H), 4.54 (d, J=12.4 Hz, 1H), 3.23 (d, J=2.6 Hz, 1H), 2.06 (s, 3H).

EXAMPLE 23

Preparation of 4a 1-4,5-bis-benzyl ester (100 mg, 0.12 mmol) was dissolved in a solution of 3% HCl/methanol (4.2 mL) and allowed to stir until TLC indicated the complete consumption of the starting material. The reaction was then diluted with CH$_2$Cl$_2$ and washed with saturated sodium bicarbonate, brine, dried (MgSO$_4$), concentrated and the residue chromatographed (silica gel 2:1 hexane:EtOAc) to yield 50.7 mg of the 1-Cl(4')-alcohol-4,5-bis-benzyl ester. To a solution of 1-Cl(4')-alcohol-4,5-bis-benzyl ester (50.7 mg, 0.06 mmol) in methanol (2.0 mL) was added dihydrotoluene (0.15 mL) and 10% Pd/C (20 mg). The reaction was then heated to 40° C. until TLC indicated the complete consumption of the starting material. The reaction was then filtered thru celite with methanol, concentrated and the residue lyophilized from benzene to give 33 mg of 4a as a white solid: $^1$H NMR (CD$_3$OD, 400 MHz) includes 7.26–7.10 (m, 5H), 6.83 (dd, J=15.6, 8.5 Hz, 1H), 6.23 (d, J=1.9 Hz, 1H), 5.77 (d, J=15.6 Hz, 1H), 5.07 (br s, 1H), 4.97 (br s, 1H), 4.63 (d, J=12.3 Hz, 1H), 4.03 (d, J=1.9 Hz, 1H), 3.89 (d, J=5.1 Hz, 1H), 3.74 (d, J=12.4 Hz, 1H): MS FAB (negitive ion) m/e 603 (M-1).

EXAMPLE 24

Preparation of 1f-4,5-bis-benzyl ester

To a 0° C. solution of 1-Cl(4')-alcohol-4,5-bis-benzyl ester (115.1 mg, 0.15 mmol) in methanol (3.0 mL) was added sodium acetate (483.2 mg, 3.22 mmol) and hydroxylamine hydrochloride 101.5 mg, 1.46 mmol). The reaction was allowed to warm to room temperature and stir until TLC indicated the complete consumption of the starting ester. The reaction was then concentrated and the residue was chromatographed (1:1 hexanes:EtOAc) to yield 71.2 mg of the deacylated material: $^1$H NMR (CDCl$_3$, 400 MHz) includes 7.34–7.1 (m, 15H), 5.19 (d, J=12.1 Hz, 1H), 5.05–4.92 (m, 5H), 4.46 (d, J=12.2 Hz, 1H), 3.75 (d, J=12.2 Hz, 1H), 0.81 (d, J=6.5 Hz, 3H).

EXAMPLE 25

Preparation of 1f

To a solution of 1f-4,5-bis-benzyl ester (71.2 mg, 0.11 mmol) in methanol (2.0 mL) was added dihydrotoluene (0.10 mL) and 10% Pd/C (50 mg). The reaction was then heated to 40° C. until TLC indicates the complete consumption of the starting material. The reaction was then filtered thru celite with methanol, concentrated and the residue lyophilized from benzene to give 49 mg of 3' as a white solid; $^1$H NMR (CD$_3$OD, 400 MHz) includes 7.26–7.12 (m, 5H), 5.09 (d, J=2.1 Hz, 1H), 4.95 (br s, 1H), 4.52 (d, J=12.1 Hz, 1H), 4.05 (d, J=2.3 Hz, 1H), 3.90 (d, J=5.4 Hz, 1H), 3.68 (d, J=12.2 Hz, 1H), 0.79 (d, J=6.7 Hz, 3H): MS FAB (negative ion) m/e 451 (M-1).

EXAMPLE 26

Preparation of 6A-4,6-bis-carbonyl-imidazolate-7-(1-methyl-1-methoxyethyl ether)-4,5-bis-t-butyl ester To a room temperature solution 6A-6-hydroxy-7-(1-methyl-1-methoxyethyl ether) (224 mg, 0.33 mmol) in $CH_2Cl_2$ (5 mL) was added carbonyl diimidazole (107 mg, 0.66 mmol). The reaction was maintained for 24 h whereupon it was concentrated in vacuo. Purification of the residue by flash chromatography (silica gel, 15–50% EtOAc/hexanes) gave 158 mg of the biscarbonylimidazolate. The $^1$H NMR ($CDCl_3$, 400 MHz) includes δ8.15 (d, J=12.2 Hz, 1H), 7.43 (dd, J=11.8, 1.4 Hz, 2H), 7.02–7.28 (m, 7H), 6.30 (d, J=2.3 Hz, 1H), 5.07 (d, J=5.2 Hz, 1H), 4.94 (d, J=18.5 Hz, 1H), 4.87 (d, J=14.2 Hz, 1H), 4.72 (d, J=14.2 Hz, 1H), 4.33 (d, J=2.3 Hz, 1H), 4.10 (d, J=7.1 Hz, 1H), 3.29 (s, 3H), 2.06 (s, 3H), 0.79 (d, J=6.8 Hz, 3H) ppm.

EXAMPLE 27

Preparation of 1e-7-(1-methyl-1-methoxyethyl ether)-4,5-bis-t-butyl ester

To a room temperature solution of the bis-carbonylimidazolate (140 mg, 0.16 mmol) in $CH_2Cl_2$ (6 mL) was added lauryl amine (119 mg, 0.65 mmol). The reaction mixture was maintained for 24 h whereupon it was concentrated in vacuo. Purification of the residue by flash chromatography (silica gel, 15–40% EtOAc/hexanes) gave 81 mg of the bis-carbamate. The $^1$H NMR ($CDCl_3$, 400 MHz) includes δ7.10–7.29 (m, 5H), 6.02 (d, J=1.7 Hz, 1H), 5.07–5.16 (m, 3H), 4.95 (d, J=16.8 Hz, 1H), 4.86 (d, J=13.6 Hz, 1H), 4.62–4.71 (m, 3H), 4.19 (d, J=1.7 Hz, 1H), 3.21 (s, 3H), 3.07–3.15 (m, 4H), 2.06 (s, 3H), 0.85 (t, J=6.5 Hz, 6H), 0.78 (d, J=6.7 Hz, 3H) ppm.

EXAMPLE 28

Preparation of 1e

Deprotection of the above bis-carbamate in the usual fashion gave the diacid. $^1$H NMR ($CD_3OD$, 400 MHz) includes δ7.13–7.31 (m, 5H), 5.76 (d, J=2.2 Hz, 1H), 5.04 (d, J=4.6 Hz, 1H), 4.57 (d, J=13.6 Hz, 1H), 4.40 (d, J=13.7 Hz, 1H), 4.11 (d, J=2.2 Hz, 1H), 2.90 (t, J=7.7 Hz, 4H), 2.09 (s, 3H), 0.81–0.93 (m, 9H) ppm.

EXAMPLE 29

Preparation of 1d-7-(1-methyl-1-methoxyethyl ether)-4,5-bis-t-butyl ester

In addition 57 mg of the C-6 monocarbamate was isolated from the column of Example 27. The $^1$H NMR ($CDCl_3$, 400 MHz) includes δ7.10–7.29 (m, 5H), 6.17 (d, J=1.8 Hz, 1H), 5.09 (d, J=5.5 Hz, 1H), 4.94 (d, J=15.1 Hz, 1H), 4.68–4.72 (m, 1H), 4.57 (d, J=12.3 Hz, 1H), 4.20 (d, J=1.7 Hz, 1H), 3.68 (d, J=12.3 Hz), 3.21 (s, 3H), 3.03–3.20 (m, 2H), 2.06 (s, 3H), 0.86 (t, J=6.6 Hz, 3H), 0.77 (d, J=6.8 Hz, 3H) ppm.

EXAMPLE 30

Preparation of 1d

Deprotection of the above C-6 carbamate in the usual fashion gave the diacid. $^1$H NMR ($CD_3OD$, 400 MHz) includes δ7.11–7.30 (m, 5H), 6.10 (br. s, 1H), 5.05 (d, J=4.9 Hz, 1H), 4.62 (d, J=12.2 Hz, 1H), 4.01 (d, J=1.9 Hz, 1H), 3.73 (d, J=12.3 Hz, 1H), 3.01–3.12 (m, 2H), 2.09 (s, 3H), 0.89 (t, J=6.6 Hz, 3H), 0.84 (d, J=6.7 Hz, 3H) ppm.

EXAMPLE 31

Preparation of 1c-7-(1-methyl-1-methoxyethyl ether)-4,5-bis-t-butyl ester

To a room temperature solution of 6A-6-hydroxy-7-(1-methyl-1-methoxyethyl ether) (201 mg, 0.33 mmol) in $CH_2Cl_2$ (2 mL) was added DMAP (36 mg, 0.30 mmol), DCC (122 mg, 0.59 mmol) and the phenoxyundecanoic acid (165 mg, 0.59 mmol). The reaction mixture was maintained for 20 h at room temperature whereupon it was diluted with hexanes (5 mL) filtered through Celite and concentrated in vacuo. Purification of the residue by flash chromatography (silica gel, 8–25% EtOAc/hexanes) gave 278 mg of the corresponding ester. The $^1$H NMR ($CDCl_3$, 400 MHz) includes δ7.20–7.30 (m, 5H), 5.78 (d, J=2.2 Hz, 1H), 5.07 (d, J=5.1 Hz, 1H), 4.93 (d, J=8.2 Hz, 2H), 4.48 (d, J=12.1 Hz, 1H), 3.76 (d, J=12.3 Hz, 1H), 3.46 (s, 2H), 2.15 (s, 3H), 1.51 (s, 9H), 1.47 (s, 9H), 0.78 (d, J=6.7 Hz, 3H) ppm.

EXAMPLE 32

Preparation of 1c

Deprotection of the above C-6 ester in the usual fashion gave the diacid. The $^1$H NMR ($CD_3OD$, 400 MHz) includes δ7.11–7.29 (m, 7H), 6.83–6.91 (m, 3H), 6.24 (d, J=2.0 Hz, 1H), 4.63 (d, J=12.3 Hz, 1H), 4.00 (d, J=3.0 Hz, 1H), 3.92 (t, J=6.5 Hz, 2H), 3.75 (d, J=12.4 Hz, 1H), 2.66 (dd, J=13.6, 6.2 Hz, 1H), 2.08 (s, 3H), 0.84 (d, J=6.7 Hz, 3H) ppm.

EXAMPLE 33

Preparation of 1b-7-(1-methyl-1-methoxyethyl ether)-4,5-bis-t-butyl ester

Following the general procedure for formation of the C-6 esters outlined above in Example 31, the C-6 myristyl ester, C-4,5 di-t-butyl ester was prepared. The $^1$H NMR ($CDCl_3$, 400 MHz) includes δ7.09–7.27 (m, 5H), 6.29 (d, J=2.0 Hz, 1H), 5.09 (d, J=5.4 Hz, 1H), 4.93 (d, J=12.4 Hz, 2H), 4.54 (d, J=12.1 Hz, 1H), 4.17 (d, J=2.0 Hz, 1H), 3.69 (d, J=12.2 Hz, 1H), 3.19 (s, 2H), 2.06 (s, 3H), 1.57 (s, 9H), 1.42 (s, 9H), 0.85 (t, J=6.7 Hz, 3H), 0.78 (d, J=6.7 Hz, 3H) ppm.

EXAMPLE 34

Preparation of 1b

Deprotection of the above C-6 ester in the usual fashion gave the diacid. The $^1$H NMR ($CD_3OD$, 400 MHz) includes δ7.10–7.29 (m, 5H), 6.24 (d, J=2.0 Hz, 1H), 5.05 (d, J=4.6 Hz, 1H), 4.63 (d, J=12.3 Hz, 1H), 3.99 (d, J=2.0 Hz, 1H), 3.75 (d, J=12.4 Hz, 1H), 2.09 (s, 3H), 0.89 (t, J=6.7 Hz, 3H), 0.84 (d, J=6.7 Hz, 3H) ppm.

EXAMPLE 35

Preparation of 3e

The following compounds were prepared according to previously described procedures and were separated and purified by reverse phase HPLC as previously. The $^1$H NMR ($CD_3OD$, 400 MHz) includes δ7.12–7.29 (m, 7H), 6.85–6.92 (m, 3H), 6.12 (d, J=2.0 Hz, 1H), 5.81 (dd, J=10.3, 5.5 Hz, 2H), 5.05 (d, J=5.0 Hz, 1H), 4.96 (d, J=7.9 Hz, 2H), 4.57 (d, J= 12.3 Hz, 1H), 3.99 (d, J=2.0 Hz, 1H), 3.93 (t, J=6.4 Hz, 2H), 3.75 (d, J=12.3

Hz, 1H), 2.66 (dd, J=13.3, 6.0 Hz, 1H), 1.91-1.96 (m, 2H), 1.70-1.78 (m, 2H), 1.55-1.63 (m, 2H), 0.84 (d, J=6.7 Hz, 3H) ppm.

EXAMPLE 36

Preparation of 3d

The $^1$H NMR (CD$_3$OD, 400 MHz) includes δ7.11-7.28 (m, 7H), 6.84-6.92 (m, 3H), 6.23 (br. s, 1H), 5.84 (d, J=5.4 Hz, 1H), 5.74 (d, J=5.5 Hz, 1H), 5.04 (d, J=4.6 Hz, 1H), 4.95 (d, J=7.8 Hz, 2H), 4.64 (d, J=12.4 Hz, 1H), 3.89-3.97 (m, 3H), 3.73 (d, J=12.2 Hz, 1H), 2.65 (dd, J=13.3, 6.5 Hz, 1H), 1.68-1.79 (m, 2H), 1.53-1.66 (m, 2H), 1.40-1.50 (m, 2H), 0.84 (d, J=6.7 Hz, 3H) ppm.

EXAMPLE 37

Preparation of 3f

The $^1$H NMR (CD$_3$OD, 400 MHz) includes δ7.11-7.29 (m, 7H), 6.83-6.92 (m, 3H), 6.09 (d, J=2.0 Hz, 1H), 5.75-5.86 (m, 4H), 5.03 (d, J=4.6 Hz, 1H), 4.95 (d, J=6.8 Hz, 2H), 4.56 (d, J=12.4 Hz, 1H), 4.21 (dd, J=5.6, 2.2 Hz, 2H), 3.97 (d, J=2.0 Hz, 1H), 3.93 (t, J=6.5 Hz, 2H), 3.74 (d, J=12.4 Hz, 1H), 2.65 (dd, J=13.3, 6.0 Hz, 1H), 0.84 (d, J=6.7 Hz, 3H) ppm.

EXAMPLE 38

Preparation of 3c

The following compounds were prepared according to previously described procedures and purified by reverse phase HPLC. The $^1$H NMR (CD$_3$OD, 400 MHz) includes δ7.11-7.29 (m, 5H), 6.12 (d, J=2.1 Hz, 1H), 5.82 (dd, J=10.0, 5.5 Hz, 2H), 5.05 (d, J=4.9 Hz, 1H), 4.96 (d, J=7.9 Hz, 2H), 4.57 (d, J=12.3 Hz, 1H), 3.99 (d, J=2.1 Hz, 1H), 3.75 (t, J=12.4 Hz, 1H), 2.67 (dd, J=13.4, 6.2 Hz, 1H), 1.91-1.97 (m, 2H), 1.55-1.63 (m, 2H), 0.89 (t, J=6.7 Hz, 3H), 0.84 (d, J=6.7 Hz, 3H) ppm.

EXAMPLE 39

Preparation of 3a

The $^1$H NMR (CD$_3$OD, 400 MHz) includes δ7.11-7.29 (m, 5H), 6.20 (d, J=1.9 Hz, 1H), 5.84 (d, J=5.5 Hz, 1H), 5.74 (d, J=5.5 Hz, 1H), 5.04 (d, J=4.9 Hz, 1H), 4.95 (d, J=8.0 Hz, 2H), 4.63 (d, J=12.4 Hz, 1H), 3.94 (d, J=1.9 Hz, 1H), 3.74 (d, J=12.4 Hz, 1H), 2.66 (dd, J=13.5, 6.4 Hz, 1H), 1.88-1.96 (m, 2H), 1.55-1.66 (m, 2H), 0.86 (t, J=6.7 Hz, 3H), 0.83 (d, J=6.7 Hz, 3H) ppm.

EXAMPLE 40

Preparation of 3b

The $^1$H NMR (CD$_3$OD, 400 MHz) includes δ7.11-7.29 (m, 5H), 6.09 (d, J=2.0 Hz, 1H), 5.76-5.88 (m, 4H), 5.04 (d, J=4.5 Hz, 1H), 4.95 (d, J=7.0 Hz, 2H), 4.56 (d, J=12.4 Hz, 1H), 3.96 (d, J=2.0 Hz, 1H), 3.74 (d, J=12.4 Hz, 1H), 2.65 (dd, J=13.6, 6.6 Hz, 1H), 0.89 (t, J=6.7 Hz, 3H), 0.84 (d, J=6.7 Hz, 3H) ppm.

EXAMPLE 41

As a specific embodiment of an oral composition of a compound of this invention, 20 mg of the compound from Example 6 is formulated with sufficient finely divided lactose to provide a total amount of 580 to 590 mg to fill a size 0 hard gelatin capsule.

EXAMPLE 42

Preparation of an Ammonium Salt

A 0.1 mmol sample of the free acid of Compound (I) is dissolved in 10 ml of ethyl acetate. The resulting solution is saturated with gaseous ammonia, upon which the ammonium salt precipitates from solution.

EXAMPLE 43

Preparation of Potassium Salt

A solution of 0.1 mmol of the free acid of Compound (I) in 10 ml of methanol is treated with an aqueous or methanolic solution containing 0.2 mmol of potassium hydroxide. Evaporation of the solvent affords the dipotassium salt. Addition of between 0.1 and 0.2 mmol of potassium hydroxide yields analogously mixtures of the mono-potassium and di-potassium salts whose composition depends upon the exact amount of potassium hydroxide added.

In a similar fashion, the sodium and lithium salts of Compound (I) can be formed.

EXAMPLE 44

Preparation of a Calcium Salt

A solution of 0.1 mmol of the free acid of a compound of formula (I) in 20 ml of 6:4 methanol/water is treated with an aqueous solution of 0.1 mmol of calcium hydroxide. The solvents are evaporated to give the corresponding calcium salt.

EXAMPLE 45

Preparation of an ethylenediamine Salt

A solution of 0.1 mmol of the free acid of a compound of formula (I) in 10 ml of methanol is treated with 0.1 mmol of ethylenediamine. Evaporation of the solvent affords the ethylenediamine salt.

The procedure can also be applied to the preparation of the N,N'-dibenzylethylenediamine salt.

EXAMPLE 46

Preparation of a Tris(hydroxymethyl)aminomethane salt

To a solution of 0.1 mmol of the free acid of a Compound of formula (I) in 10 ml of methanol is added from 0.1 to 0.2 mmol of tris(hydroxymethyl)aminomethane dissolved in 10 ml of methanol. Evaporation of the solvent gives a corresponding salt form of Compound (I) exact composition of which is determined by the molar ratio of amine added.

The method can also be applied to other amines such as, but not limited to: diethanolamine and diethylamine.

EXAMPLE 47

The preparation of a L-arginine salt

To a solution of 0.1 mmol of the free acid of a compound of formula (I) in 10 ml of 6:4 methanol/water is treated with an aqueous solution of 0.1-0.2 mmol of L-arginine. Evaporation of the solvent affords the title salt, the exact composition of which is determined by the molar ratio of amino acid to the free acid of Compound (I).

Similarly prepared are the salts of L-ornithine, L-lysine, and N-methylglucamine.

What is claimed is:

1. A compound of structural formula (I):

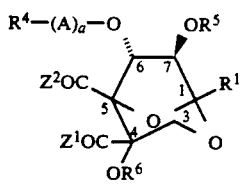 (I)

wherein
a is 0 or 1;
A is —C(O)—, —NR³—C(O)—, or —OC(O)—;
R¹ is selected from the group consisting of:
(1) $C_{1-20}$alkyl,
(2) substituted $C_{1-20}$alkyl in which one or more substituents is selected from:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$, wherein aryl is substituted with X and Y,
 (m) $R^3$—C(O)—NR³—,
 (n) $R^3R^3N$—C(O)—,
 (o) —CO₂H,
 (p) -vinylidene,
 (q) $R^3$—C(O)—,
 (r) $R^2O$—C(O)—O—,
 (s) $R^3R^3N$—C(O)—O—, and
 (t) $R^2O$—C(O)—NR³—;
(3) $C_{1-20}$alkyl wherein one or more of the carbons is replaced by —NR³—, —O—, or —S(O)$_n$—;
(4) substituted $C_{1-20}$alkyl wherein one or more of the carbons is replaced by —NR³—, —O— or —S(O)$_n$— and wherein one or more carbon substituents is selected from:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl-,
 (i) aryl substituted with X and Y,
 (j) heteroaryl substituted with X and Y,
 (k) heterocycloalkyl,
 (l) arylS(O)$_n$—, wherein aryl is substituted with X and Y,
 (m) $R^3$—C(O)—NR³—,
 (n) $R^3R^3N$—C(O)—,
 (o) —CO₂H,
 (p) -vinylidene,
 (q) $R^3$—C(O)—,
 (r) $R^2O$—C(O)—O—,
 (s) $R^3R^3N$—C(O)—O—, and
 (t) $R^2O$—C(O)—NR³—;
(5) aryl substituted with X and Y;
(6) heteroaryl substituted with X and Y;
(7) $C_{2-20}$alkenyl wherein alkenyl contains one or more double bonds;
(8) substituted $C_{2-20}$alkenyl wherein alkenyl contains one or more double bonds and wherein one or more of the carbons is substituted with:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$—, wherein aryl is substituted with X and Y,
 (m) $R^3$C(O)—NR³—,
 (n) $R^3R^3N$—C(O)—,
 (o) —CO₂H,
 (p) -vinylidene,
 (q) $R^3$—C(O)—,
 (r) $R^2O$—C(O)—O—,
 (s) $R^3R^3N$—C(O)—O—, and
 (t) $R^2O$—C(O)—NR³—;
(9) $C_{2-20}$alkenyl wherein alkenyl contains one or more double bonds and one or more of the nonolefinic carbons is replaced by —NR³—, —O— or —S(O)$_n$—;
(10) substituted $C_{2-20}$alkenyl wherein alkenyl contains one or more double bonds and one or more of the nonolefinic carbons is replaced by —NR³—, —O— or —S(O)$_n$— and wherein one or more carbon substituents is selected from:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl-,
 (i) aryl substituted with X and Y,
 (j) heteroaryl substituted with X and Y,
 (k) heterocycloalkyl,
 (l) arylS(O)$_n$—, wherein aryl is substituted with X and Y,
 (m) $R^3$—C(O)—NR³—,
 (n) $R^3R^3N$—C(O)—,
 (o) —CO₂H,
 (p) -vinylidene,
 (q) $R^3$—C(O)—,
 (r) $R^2O$—C(O)—O—,
 (s) $R^3R^3N$—C(O)—O—, and
 (t) $R^2O$—C(O)—NR³—;
(11) $C_{3-10}$cycloalkyl; and
(12) substituted $C_{3-10}$cycloalkyl in which one or more of the substituents is selected from:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl,
 (i) aryl substituted with X and Y, (j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—,
(o) $C_{1-10}$alkylS(O)$_n$—,
(p) $C_{1-10}$alkyl,
(q) —CO$_2$H,
(r) -vinylidene,
(s) $R^3$—C(O)—,
(t) $R^2O$—C(O)—O—,
(u) $R^3R^3N$—C(O)—O—, and
(v) $R^2O$—C(O)—$NR^3$—;

each $R^2$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y; and
(9) $C_{3-10}$alkynyl;

each $R^3$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y;
(9) $C_{3-10}$alkynyl;
(10) hydrogen; and
(11) $C_{1-5}$alkyl substituted with $X^1$;

$R^4$ is selected from the group consisting of:
(1) $C_{1-20}$alkyl;
(2) substituted $C_{1-20}$alkyl in which one or more substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—,
(o) —CO$_2$H,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(3) $C_{1-20}$alkyl wherein one or more of the carbons is replaced by —$NR_3$—, —O—, or —S(O)$_n$—;
(4) substituted $C_{1-20}$alkyl wherein one or more of the carbons is replaced by —$NR^3$—, —O— or —S(O)$_n$— and wherein one or more carbon substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl-,
(i) aryl substituted with X and Y,
(j) heteroaryl substituted with X and Y,
(k) heterocycloalkyl,
(l) arylS(O)$_n$—, wherein aryl is substituted with X and Y,
(m) $R^3$—C(O)—$NR^3$—,
(n) $R^3R^3N$—C(O)—,
(o) —CO$_2$H,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(5) aryl substituted with X and Y;
(6) heteroaryl substituted with X and Y;
(7) $C_{2-20}$alkenyl wherein alkenyl contains one or more double bonds;
(8) substituted $C_{2-20}$alkenyl wherein alkenyl contains one or more double bonds and wherein one or more of the carbons is substituted with:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$—, wherein aryl is substituted with X and Y,
(m) $R^3$—C(O)—$NR^3$—,
(n) $R^3R^3N$—C(O)—,
(o) —CO$_2$H,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(9) $C_{2-20}$alkenyl wherein alkenyl contains one or more double bonds and one or more of the nonolefinic carbons is replaced by —$NR^3$—, —O— or —S(O)$_n$—;
(10) substituted $C_{2-20}$alkenyl wherein alkenyl contains one or more double bonds and one or more of the nonolefinic carbons is replaced by —$NR^3$—, —O— or —S(O)$_n$— and wherein one or more carbon substituents is selected from:
(a) halogen,
(b) hydroxy,
(c) $R^3R^3N$—, (d) $R^2O-$,
(e) $R^2O-C(O)-$,
(f) $R^3-C(O)-O-$,
(g) oxo,
(h) $C_{3-10}$cycloalkyl—,
(i) aryl substituted with X and Y,
(j) heteroaryl substituted with X and Y,
(k) heterocycloalkyl,
(l) arylS(O)$_n$—, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$; and
(11) $C_{3-10}$cycloalkyl;
(12) substituted $C_{3-10}$cycloalkyl in which one or more of the substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$—, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(13) hydrogen;
$R^5$ is selected from the group consisting of:
(1) hydrogen;
(2) $C_{1-10}$alkyl;
(3) aryl substituted with X and Y;
(4) aryl$C_{1-4}$alkyl, wherein aryl is substituted with X and Y;
(5) $R^2O-C(O)-$;
(6) $C_{3-10}$cycloalkyl;
(7) $R^3-C(O)-$; and
(8) $R^3R^3N-C(O)-$;
$R^6$ and $R^{6a}$ are each independently selected from the group consisting of:
(1) $C_{1-20}$alkyl;
(2) substituted $C_{1-20}$alkyl in which one or more substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) aryl S(O)$_n$—, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3NOC(O)-O-$, and
(t) $R^2O-C(O)-NR^3-$;
(3) $C_{1-20}$alkyl wherein one or more of the carbons is replaced by $-NR^3-$, $-O-$, or $-S(O)_n-$;
(4) substituted $C_{1-20}$alkyl wherein one or more of the carbons is replaced by $-NR^3-$, $-O-$ or $-S(O)_n-$ and wherein one or more carbon substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) aryl S(O)$_n$—, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(5) $C_{2-20}$alkenyl wherein alkenyl contains one or more double bonds;
(6) substituted $C_{2-20}$alkenyl wherein alkenyl contains one or more double bonds and wherein one or more of the carbons is substituted with:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) aryl S(O)$_n$—, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(u) OC(O)O, which forms a five membered ring:

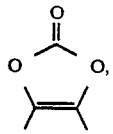

with adjacent olefinic carbons;
(7) $C_{2-20}$alkenyl wherein alkenyl contains one or more double bonds and one or more of the nonolefinic carbons is replaced by —$NR^3$—, —O— or —$S(O)_n$—;
(8) substituted $C_{2-20}$alkenyl wherein alkenyl contains one or more double bonds and one or more of the nonolefinic carbons is replaced by —$NR^3$—, —O— or —$S(O)_n$— and wherein one or more carbon substituents is selected from:
(a) halogen
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) aryl $S(O)_n$—, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(u) OC(O)O, which forms a five membered ring:

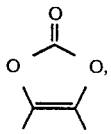

with adjacent olefinic carbons;
(9) $C_{2-20}$alkynyl wherein alkynyl contains one or more triple bonds;
(10) substituted $C_{2-20}$alkynyl wherein alkynyl contains one or more triple bonds and wherein one or more of the carbons is substituted with:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) aryl$S(O)_n$—, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(11) $C_{2-20}$alkynyl wherein alkynyl contains one or more triple bonds and one or more of the saturated carbons is replaced by —$NR^3$—, —O— or —$S(O)_n$—;
(12) substituted $C_{2-20}$alkynyl wherein alkynyl contains one or more triple bonds and one or more of the saturated carbons is replaced by —$NR^3$—, —O— or —$S(O)_n$— and wherein one or more carbon substitutents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl-,
(i) aryl substituted with X and Y,
(j) heteroaryl substituted with X and Y,
(k) heterocycloalkyl,
(l) aryl$S(O)_n$—, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(13) aryl substituted with X and Y;
(14) Heteroaryl substituted with X and Y;
(15) $C_{3-5}$ cycloalkyl;
(16) substituted $C_{3-5}$ cycloalkyl in which one or more of the substituents is selected from:
(a) $R^3O$—, and
(b) $R^3R^3N$—; and
(17) hydrogen;
aryl including X, Y substitution is:

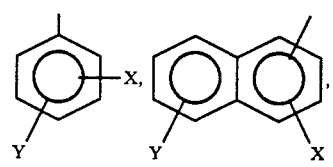

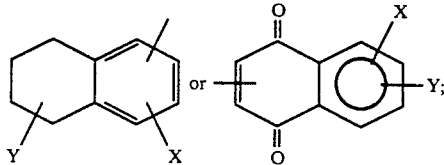

heteroaryl including X, Y substitution is selected from:

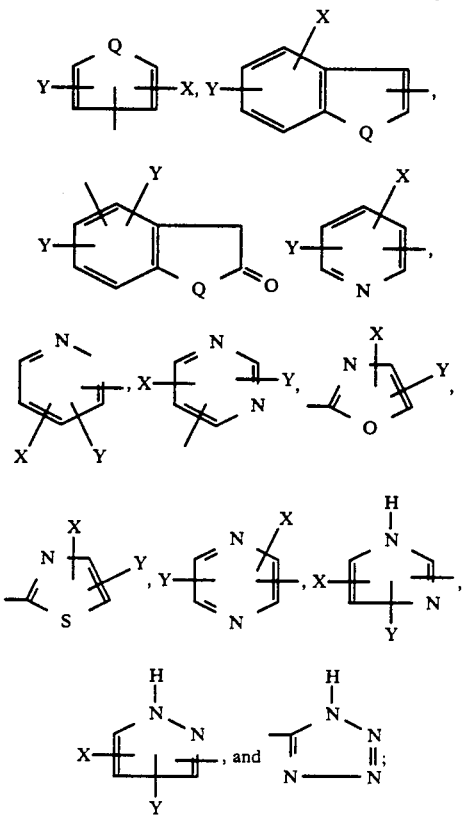

wherein:
Q is —NR³, —O— or —S—;
heterocycloalkyl is:

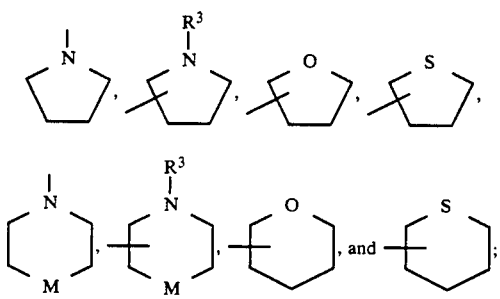

wherein:
M is —NR³, —O—, —S— or —CH₂—
X and Y are each independently selected from:
(1) hydrogen;
(2) hydroxy;
(3) halogen;
(4) trifluoromethyl;
(5) $C_{1-10}$alkyl;
(6) aryl substituted with $X^1$ and $Y^1$;
(7) $R^2O$—;
(8) arylcarbonyloxy-, wherein aryl is substituted with $X^1$ and $Y^1$;
(9) $R^3$—C(O)—O—;
(10) —CO₂R²;
(11) —CO₂H;
(12) nitro; and
(13) —NR³R³;
$X^1$ and $Y^1$ are each independently selected from:
(1) hydrogen;
(2) hydroxy;
(3) halogen;
(4) trifluoromethyl;
(5) $C_{1-4}$alkyl;
(6) $R^2O$—;
(7) $R^3$—C(O)—O—;
(8) —CO₂R²;
(9) —CO₂H; and
(10) nitro;
n is 0, 1 or 2;
$Z^1$, and $Z^2$ are each independently selected from:
(1) —OR$^{6a}$;
(2) —SR$^{6a}$; and
(3) —NR$^{6a}$R$^{6a}$;
or a pharmaceutically acceptable salt of formula (I);
provided that when $Z^1$ is —OH or —OCH₃, $Z^2$ is not —OH or —OCH₃.
2. The compound of claim 1 wherein:
$R^1$ is selected from the group consisting of:
(1) $C_{1-20}$alkyl;
(2) substituted $C_{1-20}$alkyl in which one or more substituents is selected from:
(a) halogen,
(b) hydroxy,
(c) R³R³N—,
(d) R²O—,
(e) R²O—C(O)—,
(f) R³—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) R³—C(O)—NR³—,
(n) R³R³N—C(O)—,
(o) —CO₂H,
(p) -vinylidene,
(q) R³—C(O)—,
(r) R²O—C(O)—O—,
(s) R³R³N—C(O)—O—, and
(t) R²O—C(O)—NR³—;
(3) $C_{1-20}$alkyl wherein one or more of the carbons is replaced by —NR³—, —O—, or —S(O)$_n$—;
(4) substituted $C_{1-20}$alkyl wherein one or more of the carbons is replaced by —NR³—, —O— or —S(O)$_n$— and wherein one or more carbon substituents is selected from:
(a) halogen,
(b) hydroxy,
(c) R³R³N—,
(d) R²O—,
(e) R²O—C(O)—,
(f) R³—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) R³—C(O)—NR³—,
(n) R³R³N—C(O)—,
(o) —CO₂H,
(p) -vinylidene,
(q) R³—C(O)—, (r) $R^2O-C(O)-O-$,
(s) $R^3R^3N-C(O)-O-$, and
(t) $R^2O-C(O)-NR^3-$;
(5) aryl substituted with X and Y;
(6) heteroaryl substituted with X and Y;
(7) $C_{2-20}$alkenyl wherein alkenyl contains one, two or three double bonds;
(8) substituted $C_{2-20}$alkenyl wherein alkenyl contains one, two or three double bonds and wherein one or more of the carbons is substituted with:
 (a) halogen,
 (b) hydroxy,
 (c) $R^3R^3N-$,
 (d) $R^2O-$,
 (e) $R^2O-C(O)-$,
 (f) $R^3-C(O)-O-$,
 (g) oxo,
 (h) $C_{3-10}$cycloalkyl,
 (i) aryl substituted with X and Y,
 (j) heteroaryl substituted with X and Y,
 (k) heterocycloalkyl,
 (l) aryl$S(O)_n$, wherein aryl is substituted with X and Y,
 (m) $R^3-C(O)-NR^3-$,
 (n) $R^3R^3N-C(O)-$,
 (o) $-CO_2H$,
 (p) -vinylidene,
 (q) $R^3-C(O)-$,
 (r) $R^2O-C(O)-O-$,
 (s) $R^3R^3N-C(O)-O-$, and
 (t) $R^2O-C(O)-NR^3-$;
(9) $C_{2-20}$alkenyl wherein alkenyl contains one, two or three double bonds and one or more of the nonolefinic carbons is replaced by $-NR^3-$, $-O-$ or $-S(O)_n-$; and
(10) substituted $C_{2-20}$alkenyl wherein alkenyl contains one, two or three double bonds and one or more of the nonolefinic carbons is replaced by $-NR^3$, $-O-$ or $-S(O)_n-$ and wherein one or more carbons substituents is selected from:
 (a) halogen,
 (b) hydroxy,
 (c) $R^3R^3N-$,
 (d) $R^2O-$,
 (e) $R^2O-C(O)-$,
 (f) $R^3-C(O)-O-$,
 (g) oxo,
 (h) $C_{3-10}$cycloalkyl,
 (i) aryl substituted with X and Y,
 (j) heteroaryl substituted with X and Y,
 (k) heterocycloalkyl,
 (l) aryl$S(O)_n$, wherein aryl is substituted with X and Y,
 (m) $R^3-C(O)-NR^3-$,
 (n) $R^3R^3N-C(O)-$,
 (o) $-CO_2H$,
 (p) -vinylidene,
 (q) $R^3-C(O)-$,
 (r) $R^2O-C(O)-O-$,
 (s) $R^3R^3N-C(O)-O-$, and
 (t) $R^2O-C(O)-NR^3-$;

each $R^2$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y; and
(9) $C_{3-10}$alkynyl;

each $R^3$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y;
(9) $C_{3-10}$alkynyl;
(10) hydrogen; and
(11) $C_{1-5}$alkyl substituted with $X^1$;

$R^4$ is selected from the group consisting of:
(1) $C_{1-20}$alkyl;
(2) substituted $C_{1-20}$alkyl in which one or more substituents is selected from:
 (a) halogen,
 (b) hydroxy,
 (c) $R^3R^3N-$,
 (d) $R^2O-$,
 (e) $R^2O-C(O)-$,
 (f) $R^3-C(O)-O-$,
 (g) oxo,
 (h) $C_{3-10}$cycloalkyl,
 (i) aryl substituted with X and Y,
 (j) heteroaryl substituted with X and Y,
 (k) heterocycloalkyl,
 (l) aryl$S(O)_n$, wherein aryl is substituted with X and Y,
 (m) $R^3-C(O)-NR^3-$,
 (n) $R^3R^3N-C(O)-$;
 (o) $-CO_2H$,
 (p) -vinylidene,
 (q) $R^3-C(O)-$,
 (r) $R^2O-C(O)-O-$,
 (s) $R^3R^3N-C(O)-O-$, and
 (t) $R^2O-C(O)-NR^3-$,
(3) $C_{1-20}$alkyl wherein one or more of the carbons is replaced by $-NR^3-$, $-O-$, or $-S(O)n-$;
(4) substituted $C_{1-20}$alkyl wherein one or more of the carbons is replaced by $-NR^3-$, $-O-$ or $-S(O)_n-$ and wherein one or more carbon substituents is selected from:
 (a) halogen,
 (b) hydroxy,
 (c) $R^3R^3N-$,
 (d) $R^2O-$,
 (e) $R^2O-C(O)-$,
 (f) $R^3-C(O)-O-$,
 (g) oxo,
 (h) $C_{3-10}$cycloalkyl,
 (i) aryl substituted with X and Y,
 (j) heteroaryl substituted with X and Y,
 (k) heterocycloalkyl, (l) arylS(O)$_n$, wherein aryl is substituted with X and Y,
(m) $R^3$—C(O)—$NR^3$—,
(n) $R^3R^3N$—C(O)—,
(o) —CO$_2$H,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(5) aryl substituted with X and Y;
(6) heteroaryl substituted with X and Y;
(7) C$_{2-20}$ alkenyl wherein alkenyl contains one, two or three double bonds;
(8) substituted C$_{2-20}$ alkenyl wherein alkenyl contains one, two or three double bonds and wherein one or more of the carbons is substituted with:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—,
(o) —CO$_2$H,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(9) C$_{2-20}$alkenyl wherein alkenyl contains one, two or three double bonds and one or more of the nonolefinic carbons is replaced by —$NR^3$—, —O— or —S(O)$_n$—;
(10) substituted C$_{2-20}$alkenyl wherein alkenyl contains one, two or three double bonds and one or more of the nonolefinic carbons is replaced by —$NR^3$—, —O— or —S(O)$_n$— and wherein one or more carbon substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—,
(o) —CO$_2$H,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—; and
(11) hydrogen;

$R^5$ is selected from the group consisting of:
(1) hydrogen;
(2) C$_{1-10}$alkyl;
(3) aryl substituted with X and Y;
(4) arylC$_{1-4}$alkyl, wherein aryl is substituted with X and Y;
(5) $R^2O$—C(O)—;
(6) C$_{3-10}$cycloalkyl;
(7) $R^2$—C(O)—; and
(8) $R^3R^3N$—C(O)—;

$R^6$ and $R^{6a}$ are each independently selected from the group consisting of:
(1) C$_{1-20}$alkyl;
(2) substituted C$_{1-20}$alkyl in which one or more substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) aryl S(O)n, wherein aryl is substituted with X and Y,
(m) $R^3$—C(O)—$NR^3$—,
(n) $R^3R^3N$—C(O)—,
(o) —CO$_2$H,
(p) -vinylidene,
(q) $R^3$—C(O)—,
(r) $R^2O$—C(O)—O—,
(s) $R^3R^3NC(O)$—O—, and
(t) $R^2O$—C(O)—$NR^3$—;
(3) C$_{1-20}$alkyl wherein one or more of the carbons is replaced by —$NR^3$—, —O—, or —S(O)$_n$—;
(4) substituted C$_{1-20}$alkyl wherein one or more of the carbons is replaced by —$NR^3$—, —O— or —S(O)$_n$— and wherein one or more carbon substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) aryl S(O)$_n$—, wherein aryl is substituted with X and Y,
(m) $R^3$—C(O)—$NR^3$—,
(n) $R^3R^3N$—C(O)—,
(o) —CO$_2$H,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(5) C$_{2-20}$alkenyl wherein alkenyl contains one, two or three double bonds;

(6) substituted $C_{2-20}$alkenyl wherein alkenyl contains one, two or three double bonds and wherein one or more of the carbons is substituted with:
  (a) halogen
  (b) hydroxy,
  (c) $R^3R^3N$—,
  (d) $R^2O$—,
  (e) $R^2O$—C(O)—,
  (f) $R^3$—C(O)—O—,
  (g) oxo,
  (h) $C_{3-10}$cycloalkyl,
  (i) aryl substituted with X and Y,
  (j) heteroaryl substituted with X and Y,
  (k) heterocycloalkyl,
  (l) aryl S(O)$_n$—, wherein aryl is substituted with X and Y,
  (m) $R^3$—C(O)—$NR^3$—,
  (n) $R^3R^3N$—C(O)—,
  (o) —$CO_2H$,
  (p) -vinylidene,
  (q) $R^3$—C(O)—,
  (r) $R^2O$—C(O)—O—,
  (s) $R^3R^3N$—C(O)—O—, and
  (t) $R^2O$—C(O)—$NR^3$—;
  (u) OC(O)O, which forms a five membered ring:

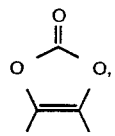

with adjacent olefinic carbons;
(7) $C_{2-20}$alkenyl wherein alkenyl contains one, two or three double bonds and one or more of the nonolefinic carbons is replaced by —$NR^3$—, —O— or —S(O)$_n$—;
(8) substituted $C_{2-20}$alkenyl wherein alkenyl contains one, two or three double bonds and one or more of the nonolefinic carbons is replaced by —$NR^3$—, —O— or —S(O)$_n$— and wherein one or more carbon substituents is selected from:
  (a) halogen
  (b) hydroxy,
  (c) $R^3R^3N$—,
  (d) $R^2O$—,
  (e) $R^2O$—C(O)—,
  (f) $R^3$—C(O)—O—,
  (g) oxo,
  (h) $C_{3-10}$cycloalkyl,
  (i) aryl substituted with X and Y,
  (j) heteroaryl substituted with X and Y,
  (k) heterocycloalkyl,
  (l) aryl S(O)$_n$—, wherein aryl is substituted with X and Y,
  (m) $R^3$—C(O)—$NR^3$—,
  (n) $R^3R^3N$-13 C(O)—,
  (o) —$CO_2H$,
  (p) -vinylidene,
  (q) $R^3$—C(O)—,
  (r) $R^2O$—C(O)—O—,
  (s) $R^3R^3N$—C(O)—O—, and
  (t) $R^2O$—C(O)—$NR^3$—;
  (u) OC(O)O, which forms a five membered ring:

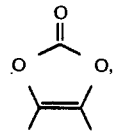

with adjacent olefinic carbons;
(9) $C_{2-20}$alkynyl wherein alkynyl contains one or more triple bonds;
(10) substituted $C_{2-20}$alkynyl wherein alkynyl contains one or more triple bonds and wherein one or more of the carbons is substituted with:
  (a) halogen,
  (b) hydroxy,
  (c) $R^3R^3N$—,
  (d) $R^2O$—,
  (e) $R^2O$—C(O)—,
  (f) $R^3$—C(O)—O—,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$—, wherein aryl is substituted with X and Y,
  (m) $R^3$—C(O)—$NR^3$—,
  (n) $R^3R^3N$—C(O)—,
  (o) —$CO_2H$,
  (p) -vinylidene,
  (q) $R^3$—C(O)—,
  (r) $R^2O$—C(O)—O—,
  (s) $R^3R^3N$—C(O)—O—, and
  (t) $R^2O$—C(O)—$NR^3$—;
(11) $C_{2-20}$alkynyl wherein alkynyl contains one or more triple bonds and one or more of the saturated carbons is replaced by —$NR^3$—, —O— or —S(O)$_n$—;
(12) substituted $C_{2-20}$alkynyl wherein alkynyl contains one or more triple bonds and one or more of the saturated carbons is replaced by —$NR^3$—, —O— or —S(O)$_n$— and wherein one or more carbon substitutents is selected from:
  (a) halogen,
  (b) hydroxy,
  (c) $R^3R^3N$—,
  (d) $R^2O$—,
  (e) $R^2O$—C(O)—,
  (f) $R^3$—C(O)—O—,
  (g) oxo,
  (h) $C_{3-10}$cycloalkyl- ,
  (i) aryl substituted with X and Y,
  (j) heteroaryl substituted with X and Y,
  (k) heterocycloalkyl,
  (l) arylS(O)$_n$—, wherein aryl is substituted with X and Y,
  (m) $R^3$—C(O)—$NR^3$—,
  (n) $R^3R^3N$—C(O)—,
  (o) —$CO_2H$,
  (p) -vinylidene,
  (q) $R^3$—C(O)—,
  (r) $R^2O$—C(O)—O—,
  (s) $R^3R^3N$—C(O)—O—, and
  (t) $R^2O$—C(O)—$NR^3$—;
(13) aryl substituted with X and Y;
(14) Heteroaryl substituted with X and Y;
(15) $C_{3-5}$ cycloalkyl;

(16) substituted C$_{3-5}$ cycloalkyl in which one or more of the substituents is selected from:
(a) R$^3$O—, and
(b) R$^3$R$^3$N—; and
(17) hydrogen;
aryl including X, Y substitution is

[structures]

heteroaryl including X, Y substitution is selected from:

[structures]

wherein: Q is —NR$^3$, —O— or —S—;
heterocycloalkyl is selected from:

[structures]

-continued

[structures]

wherein: M is —NR$^3$, —O—, —S— or —CH$_2$—
X and Y are each independently selected from:
(1) hydrogen;
(2) hydroxy;
(3) halogen;
(4) trifluoromethyl;
(5) C$_{1-10}$alkyl;
(6) aryl substituted with X$^1$ and Y$^1$;
(7) R$^2$O—;
(8) arylcarbonyloxy-, wherein aryl is substituted with X$^1$ and Y$^1$;
(9) R$^3$—C(O)—O—;
(10) —CO$_2$R$^2$;
(11) —CO$_2$H;
(12) nitro; and
(13) —NR$^3$R$^3$;
X$^1$ and Y$^1$ are each independently selected from:
(1) hydrogen;
(2) hydroxy;
(3) halogen;
(4) trifluoromethyl;
(5) C$_{1-4}$alkyl;
(6) R$^2$O—;
(7) R$^3$—C(O)—O—;
(8) —CO$_2$R$^2$;
(9) —CO$_2$H; and
(10) nitro;
n is 0, 1 or 2; and
Z$^1$ and Z$^2$ are each independently selected from:
(1) —OR$^{6a}$;
(2) —SR$^{6a}$; and
(3) —NR$^{6a}$R$^{6a}$.

3. The compound of claim 1 wherein:
R$^1$ is selected from the group consisting of:
(1) C$_{1-20}$alkyl;
(2) substituted C$_{1-20}$alkyl in which one or more substituents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;

(3) $C_{1-20}$alkyl wherein one or more of the carbons is replaced by $-NR^3-$, $-O-$, or $-S(O)_n-$;
(4) substituted $C_{1-20}$alkyl wherein one or more of the carbons is replaced by $-NR^3-$, $-O-$ or $-S(O)_n-$ and wherein one or more carbon substituents is selected from:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3N-C(O)-O-$, and
  (t) $R^2O-C(O)-NR^3-$;
(5) aryl substituted with X and Y;
(6) heteroaryl substituted with X and Y;
(7) $C_{2-20}$alkenyl wherein alkenyl contains one, two or three double bonds;
(8) substituted $C_{2-20}$alkenyl wherein alkenyl contains one, two or three double bonds and wherein one or more of the carbons is substituted with:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3N-C(O)-O-$, and
  (t) $R^2O-C(O)-NR^3-$;
(9) $C_{2-20}$alkenyl wherein alkenyl contains one, two or three double bonds and one or more of the nonolefinic carbons is replaced by $-NR^3-$, $-O-$ or $-S(O)_n-$; and
(10) substituted $C_{2-20}$alkenyl wherein alkenyl contains one, two or three double bonds and one or more of the nonolefinic carbons is replaced by $-NR^3-$, $-O-$ or $-S(O)_n-$ and wherein one or more carbons substituents is selected from:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3N-C(O)-O-$, and
  (t) $R^2O-C(O)-NR^3-$;

each $R^2$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y; and
(9) $C_{3-10}$alkynyl;

each $R^3$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y;
(9) $C_{3-10}$alkynyl;
(10) hydrogen; and
(11) $C_{1-5}$alkyl substituted with $X^1$;

$R^4$ is selected from the group consisting of:
(1) $C_{1-20}$alkyl;
(2) substituted $C_{1-20}$alkyl in which one or more substituents is selected from:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3-C(O)-NR^3-$,
  (n) $R^3R^3N-C(O)-$,
  (o) $-CO_2H$, (p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—,
(3) $C_{1-20}$alkyl wherein one or more of the carbons is replaced by —$NR^3$—, —O—, or —$S(O)_n$—;
(4) substituted $C_{1-20}$alkyl wherein one or more of the carbons is replaced by —$NR^3$—, —O— or —$S(O)_n$— and wherein one or more carbon substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) $arylS(O)_n$, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(5) aryl substituted with X and Y;
(6) heteroaryl substituted with X and Y;
(7) $C_{2-20}$ alkenyl wherein alkenyl contains one, two or three double bonds;
(8) substituted $C_{2-20}$ alkenyl wherein alkenyl contains one, two or three double bonds and wherein one or more of the carbons is substituted with:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) $arylS(O)_n$, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;
(9) $C_{2-20}$alkenyl wherein alkenyl contains one, two or three double bonds and one or more of the nonolefinic carbons is replaced by —$NR^3$—, —O— or —$S(O)_n$—;
(10) substituted $C_{2-20}$alkenyl wherein alkenyl contains one, two or three double bonds and one or more of the nonolefinic carbons is replaced by —$NR^3$—, —O— or —$S(O)_n$— and wherein one or more carbon substitutents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) $arylS(O)_n$, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—; and
(11) hydrogen;
$R^5$ is selected from the group consisting of:
(1) hydrogen;
(2) $C_{1-10}$alkyl;
(3) aryl substituted with X and Y;
(4) $arylC_{1-4}$alkyl, wherein aryl is substituted with X and Y;
(5) $R^2O$—C(O)—;
(6) $C_{3-10}$cycloalkyl;
(7) $R^2$—C(O)—; and
(8) $R^3R^3N$—C(O)—;
$R^6$ and $R^{6a}$ are each independently selected from the group consisting of:
(1) $C_{1-20}$alkyl;
(2) substituted $C_{1-20}$alkyl in which one or more substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) aryl $S(O)n$, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3NOC(O)$—O—, and
(t) $R^2O$—C(O)—$NR^3$—;
(3) $C_{1-20}$alkyl wherein one or more of the carbons is replaced by —$NR^3$—, —O—, or —$S(O)_n$—;
(4) substituted $C_{1-20}$alkyl wherein one or more of the carbons is replaced by —$NR^3$—, —O— or —$S(O)_n$— and wherein one or more carbon substituents is selected from:
(a) halogen,
(b) hydroxy, (c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;

(5) $C_{2-20}$alkenyl wherein alkenyl contains one, two or three double bonds;

(6) substituted $C_{2-20}$alkenyl wherein alkenyl contains one, two or three double bonds and wherein or more of the carbons is substituted with:
(a) halogen
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(u) OC(O)O, which forms a five membered ring:

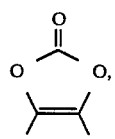

with adjacent olefinic carbons;
(7) $C_{2-20}$alkenyl wherein alkenyl contains one, two or three double bonds and one or more of the nonolefinic carbons is replaced by $-NR^3-$, $-O-$ or $-S(O)_n-$;
(8) substituted $C_{2-20}$alkenyl wherein alkenyl contains one, two or three double bonds and one or more of the nonolefinic carbons is replaced by $-NR^3-$, $-O-$ or $-S(O)_n-$ and wherein one or more carbon substituents is selected from:
(a) halogen
(b) hydroxy, (c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(u) OC(O)O, which forms a five membered ring:

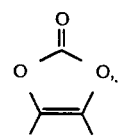

with adjacent olefinic carbons;
(9) $C_{2-20}$alkynyl wherein alkynyl contains one, two or three triple bonds;
(10) substituted $C_{2-20}$alkynyl wherein alkynyl contains one, two or three triple bonds and wherein one or more of the carbons is substituted with:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(11) $C_{2-20}$alkynyl wherein alkynyl contains one, two or three triple bonds and one or more of the saturated carbons is replaced by $-NR^3-$, $-O-$ or $-S(O)_n-$;
(12) substituted $C_{2-20}$alkynyl wherein alkynyl contains one, two or three triple bonds and one or more of the saturated carbons is replaced by $-NR^3-$, $-O-$ or $-S(O)_n-$ and wherein one or more carbon substitutents is selected from:
(a) halogen,
(b) hydroxy,
(c) $R^3R^3N-$, (d) R²O—,
(e) R²O—C(O)—,
(f) R³—C(O)—O—,
(g) oxo,
(h) C₃₋₁₀cycloalkyl-,
(i) aryl substituted with X and Y,
(j) heteroaryl substituted with X and Y,
(k) heterocycloalkyl,
(l) arylS(O)ₙ—, wherein aryl is substituted with X and Y,
(m) R³—C(O)—NR³—,
(n) R³R³N—C(O)—,
(o) —CO₂H,
(p) -vinylidene,
(q) R³—C(O)—,
(r) R²O—C(O)—O—,
(s) R³R³N—C(O)—O—, and
(t) R²O—C(O)—NR³—;
(13) aryl substituted with X and Y;
(14) Heteroaryl substituted with X and Y;
(15) C₃₋₅ cycloalkyl;
(16) substituted C₃₋₅ cycloalkyl in which one or more of the substituents is selected from:
  (a) R³O—, and
  (b) R³R³N—; and
(17) hydrogen;
aryl is phenyl with X and Y substitution

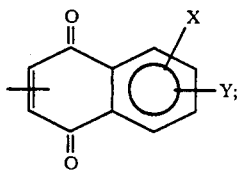

heteroaryl including X, Y substitution is selected from:

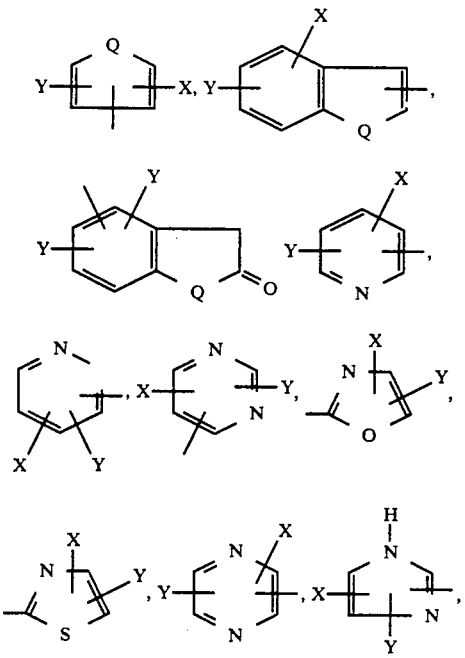

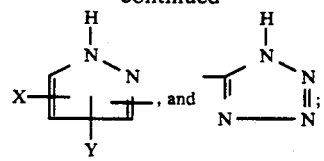

wherein: Q is —NR³, —O— or —S—;
heterocycloalkyl is selected from:

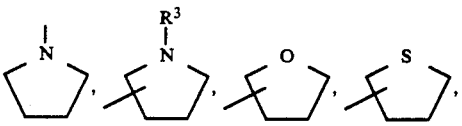

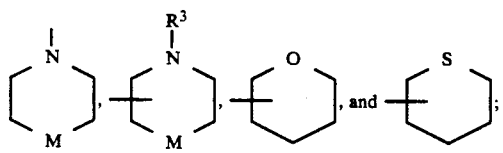

wherein: M is —NR³, —O—, —S— or —CH₂—
X and Y are each independently selected from:
(1) hydrogen;
(2) hydroxy;
(3) halogen;
(4) trifluoromethyl;
(5) C₁₋₁₀alkyl;
(6) aryl substituted with X¹ and Y¹;
(7) R²O—;
(8) arylcarbonyloxy-, wherein aryl is substituted with X¹ and Y¹;
(9) R³—C(O)—O—;
(10) —CO₂R²;
(11) —CO₂H;
(12) nitro; and
(13) —NR³R³;
X¹ and Y¹ are each independently selected from:
(1) hydrogen;
(2) hydroxy;
(3) halogen;
(4) trifluoromethyl;
(5) C₁₋₄alkyl;
(6) R²O—;
(7) R³—C(O)—O—;
(8) —CO₂R²;
(9) —CO₂H; and
(10) nitro;
n is 0, 1 or 2; and
Z¹ and Z² are each independently selected from:
(1) —OR⁶ᵃ;
(2) —SR⁶ᵃ; and
(3) —NR⁶ᵃR⁶ᵃ.
4. The compound of claim 1 wherein:
R¹ is selected from the group consisting of:
(1) C₂₋₁₆alkyl;
(2) substituted C₂₋₁₆alkyl in which one or more substituents is selected from:
  (a) hydroxy,
  (b) R²O—,
  (c) R²O—C(O)—,
  (d) R³—C(O)—O—,
  (e) oxo,
  (f) C₃₋₁₀cycloalkyl,
  (g) aryl substituted with X and Y, (h) $R^3R^3N-C(O)-$,
(i) $-CO_2H$,
(j) -vinylidene,
(k) $R^3-C(O)-$,
(l) $R^2O-C(O)-O-$, and
(m) $R^3R^3N-C(O)-O-$;

(3) $C_{2-16}$alkyl wherein one of the carbons is replaced by $-NR^3-$, $-O-$, or $-S(O)_n-$;

(4) substituted $C_{2-16}$alkyl wherein one of the carbons is replaced by $-NR^3-$, $-O-$ or $-S(O)_n-$ and wherein one or more carbon substituents is selected from:
(a) hydroxy,
(c) $R^2O-$,
(c) $R^2O-C(O)-$,
(d) $R^3-C(O)-O-$,
(e) oxo,
(f) $C_{3-10}$cycloalkyl,
(g) aryl substituted with X and Y,
(h) $R^3R^3N-C(O)-$,
(i) $-CO_2H$,
(j) -vinylidene,
(k) $R^3-C(O)-$,
(l) $R^2O-C(O)-O-$, and
(m) $R^3R^3N-C(O)-O-$;

(5) $C_{2-16}$alkenyl wherein alkenyl contains one, two or three double bonds;

(6) substituted $C_{2-16}$alkenyl wherein alkenyl contains one, two or three double bonds and wherein one or more of the carbons is substituted with:
(a) hydroxy,
(b) $R^2O-$,
(c) $R^2O-C(O)-$,
(d) $R^3-C(O)-O-$,
(e) oxo,
(f) $C_{3-10}$cycloalkyl,
(g) aryl substituted with X and Y,
(h) $R^3R^3N-C(O)-$,
(i) $-CO_2H$,
(j) -vinylidene,
(k) $R^3-C(O)-$,
(l) $R^2O-C(O)-O-$, and
(m) $R^3R^3N-C(O)-O-$;

(7) $C_{2-16}$alkenyl wherein alkenyl contains one, two or three double bonds and one or more of the nonolefinic carbons is replaced by $-NR^3-$, $-O-$ or $-S(O)_n-$; and (8) substituted $C_{2-16}$alkenyl wherein alkenyl contains one, two or three double bonds and one or more of the nonolefinic carbons is replaced by $-NR^3-$, $-O-$ or $-S(O)_n-$ and wherein one or more carbons substituents is selected from:
(a) hydroxy,
(b) $R^2O-$,
(c) $R^2O-C(O)-$,
(d) $R^3-C(O)-O-$,
(e) oxo,
(f) $C_{3-10}$cycloalkyl,
(g) aryl substituted with X and Y,
(h) $R^3R^3N-C(O)-$,
(i) $-CO_2H$,
(j) -vinylidene,
(k) $R^3-C(O)-$,
(l) $R^2O-C(O)-O-$, and
(m) $R^3R^3N-C(O)-O-$;

each $R^2$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl; and
(8) aryl$C_{2-10}$alkenyl wherein aryl is substituted with X and Y;

each $R^3$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y; and
(9) hydrogen;

$R^4$ is selected from the group consisting of:
(1) $C_{1-20}$alkyl;
(2) substituted $C_{1-20}$alkyl in which one or more substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) aryl$S(O)_n$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;

(3) $C_{1-20}$alkyl wherein one or more of the carbons is replaced by $-NR^3-$, $-O-$, or $-S(O)_n-$;

(4) substituted $C_{1-20}$alkyl wherein one or more of the carbons is replaced by $-NR^3-$, $-O-$ or $-S(O)_n-$ and wherein one or more carbon substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl, (l) arylS(O)$_n$, wherein aryl is substituted with X and Y,
(m) $R^3$—C(O)—$NR^3$—,
(n) $R^3R^3N$—C(O)—,
(o) —CO$_2$H,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;

(5) aryl substituted with X and Y;
(6) C$_{2-20}$ alkenyl wherein alkenyl contains one, two or three double bonds;
(7) substituted C$_{2-20}$ alkenyl wherein alkenyl contains one, two or three double bonds and wherein one or more of the carbons is substituted with:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) $R^3$—C(O)—$NR^3$—,
(n) $R^3R^3N$—C(O)—,
(o) —CO$_2$H,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—; and
(8) hydrogen;

$R^5$ is selected from the group consisting of:
(1) hydrogen;
(2) C$_{1-3}$alkyl; and
(3) $R^2$—C(O)—;

$R^6$ is selected from the group consisting of:
(1) C$_{1-20}$alkyl;
(2) substituted C$_{1-20}$alkyl in which one or more substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) $R^3$—C(O)—$NR^3$—,
(m) $R^3R^3N$—C(O)—,
(n) —CO$_2$H, and
(o) $R^2O$—C(O)—$NR^3$—;
(3) C$_{1-20}$alkyl wherein one or more of the carbons is replaced by —$NR^3$—, —O—, or —S(O)$_n$—;
(4) substituted C$_{1-20}$alkyl wherein one or more of the carbons is replaced by —$NR^3$—, —O—, or —S(O)$_n$— and wherein one or more carbon substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) $R^3$—C(O)—$NR^3$—,
(m) $R^3R^3N$—C(O)—,
(n) —CO$_2$H, and
(o) $R^2O$—C(O)—$NR^3$—;
(5) C$_{2-20}$alkenyl wherein alkenyl contains one or more double bonds;
(6) substituted C$_{2-20}$alkenyl wherein alkenyl contains one or more double bonds and wherein one or more of the carbons is substituted with:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) $R^3$—C(O)—$NR^3$—,
(m) $R^3R^3N$—C(O)—,
(n) —CO$_2$H, and
(o) $R^2O$—C(O)—$NR^3$—;
(p) OC(O)O, which forms a five membered ring:

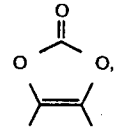

with adjacent olefinic carbons;
(7) C$_{2-20}$alkynyl wherein alkynyl contains one or more triple bonds;
(8) substituted C$_{2-20}$alkynyl wherein alkynyl contains one or more triple bonds and wherein one or more of the carbons is substituted with:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) $R^3$—C(O)—$NR^3$—,
(m) $R^3R^3N$—C(O)—,
(n) —CO$_2$H, and
(o) $R^2O$—C(O)—$NR^3$—;
(9) aryl substituted with X and Y
(10) Heteroaryl substituted with X and Y

(11) C$_{3-5}$ cycloalkyl
(12) substituted C$_{3-5}$ cycloalkyl in which one or more of the substituents is selected from:
 (a) R$^3$O—, and
 (b) R$^3$R$^3$N—; and
(13) hydrogen;
aryl is phenyl with X and Y substitution or;

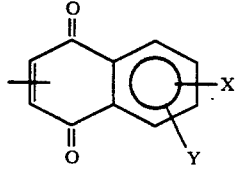

X and Y are each independently selected from:
(1) hydrogen;
(2) hydroxy;
(3) halogen;
(4) trifluoromethyl;
(5) C$_{1-10}$alkyl;
(6) aryl substituted with X$^1$ and Y$^1$;
(7) R$^2$O—;
(8) arylcarbonyloxy-, wherein aryl is substituted with X$^1$ and Y$^1$;
(9) R$^3$—C(O)—O—;
(10) —CO$_2$R$^2$;
(11) —CO$_2$H; and
(12) nitro;
X$^1$ and Y$^1$ are each independently selected from:
(1) hydrogen;
(2) hydroxy;
(3) halogen;
(4) trifluoromethyl;
(5) C$_{1-4}$alkyl;
(6) R$^2$O—;
(7) R$^3$—C(O)—O—;
(8) —CO$_2$R$^2$;
(10) —CO$_2$H; and
(11) nitro;
n is 0, 1 or 2; and
Z$^1$ and Z$^2$ are each independently selected from:
(1) —OR$^6$;
(2) —SR$^6$; and
(3) —NR$^6$R$^6$.

5. The compound of claim 3 wherein Z$^1$ and Z$^2$ are OR$^{6a}$.

6. The compound of claim 5 wherein each R$^{6a}$ is independently selected from the group consisting of:
(i) H;
(ii) C$_{1-5}$ alkyl;
(iii) C$_{1-5}$ alkyl substituted with
 a) C$_{1-5}$ alkylcarbonyloxy;
 b) arylcarbonyloxy;
 c) C$_{1-5}$ alkoxycarbonyloxy;
 d) aryloxycarbonyloxy;

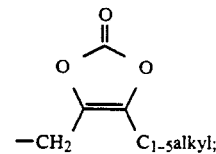   e)

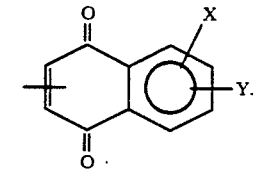   f)

7. The compound of claim 3 of the structural formula (IV)

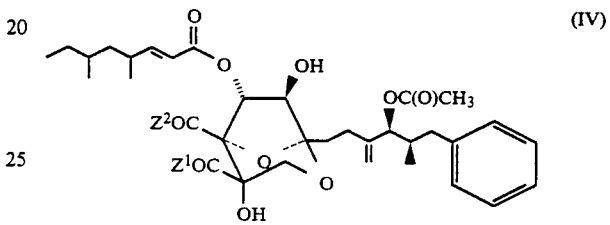   (IV)

wherein:
Z$^1$ and Z$^2$ are selected from the group consisting of:

|  | Z$^1$ | Z$^2$ |
|---|---|---|
| 2a | OCH(CH$_3$)OCOOCH$_2$CH$_3$ | OH |
| 2b | OCH(CH$_3$)OCOC(CH$_3$)$_3$ | OH |
| 2c | (see structure) | OH |
| 2d | OCH$_2$OC(O)C(CH$_3$)$_3$ | OH. |

8. The compound of claim 3 of the structural formula (VI):

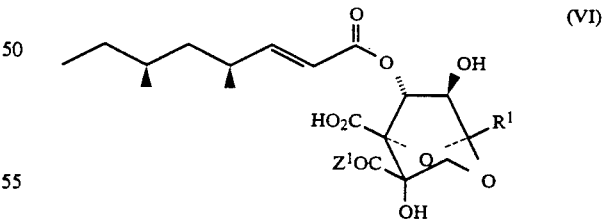   (VI)

wherein
R$^1$ and Z$^1$ are selected from the group consisting of:

|  | R$^1$ | Z$^1$ |
|---|---|---|
| 4c | CH$_2$CH$_2$C(CH$_2$)CH(OCOnPr)CH(CH$_3$)CH$_2$Ph | OCH$_2$OC(O)C(CH$_3$)$_3$ |
| 4e | CH$_2$CH$_2$C(CH$_2$)CH(OCOPh)CH(CH$_3$)CH$_2$Ph | OCH$_2$OC(O)C(CH$_3$)$_3$. |

9. A pharmaceutical composition comprising a nontoxic therapeutically effective amount of a compound of claim 1 and a pharmaceutically acceptable carrier.

10. The compound of claim 3 of the structural formula (V):
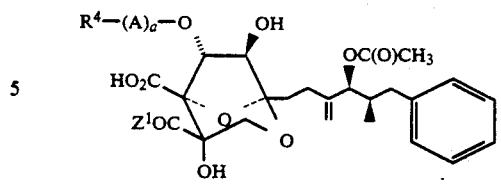
wherein:
$Z^1$, $Z^2$ and $R^4(A)_a-$ are selected from the group consisting of:
| | $R^4-(A)_a-$ | $Z^1$ | $Z^2$ |
|---|---|---|---|
| 3a | $CH_3(CH_2)_{12}C(O)$ | OH | $OCH_2OC(O)C(CH_3)_3$ |
| 3b | $CH_3(CH_2)_{12}C(O)$ | $OCH_2OC(O)C(CH_3)_3$ | $OCH_2OC(O)C(CH_3)_3$ |
| 3c | $CH_3(CH_2)_{12}C(O)$ | $OCH_2OC(O)C(CH_3)_3$ | OH |
| 3d | $PhO(CH_2)_{10}C(O)$ | OH | $OCH_2OC(O)C(CH_3)_3$ |
| 3e | $PhO(CH_2)_{10}C(O)$ | $OCH_2OC(O)C(CH_3)_3$ | OH |
| 3f | $PhO(CH_2)_{10}C(O)$ | $OCH_2OC(O)C(CH_3)_3$ | $OCH_2OC(O)C(CH_3)_3$ |
* * * * *